United States Patent
Nemoto et al.

(10) Patent No.: US 11,510,768 B2
(45) Date of Patent: Nov. 29, 2022

(54) WARP-KNITTED FABRIC AND MEDICAL MATERIAL

(71) Applicants: EDUCATIONAL FOUNDATION OF OSAKA MEDICAL AND PHARMACEUTICAL UNIVERSITY, Takatsuki (JP); TEIJIN LIMITED, Osaka (JP)

(72) Inventors: Shintaro Nemoto, Takatsuki (JP); Hideaki Yamada, Fukui (JP); Jun Sakurai, Fukui (JP); Kazuteru Kohno, Osaka (JP); Masaya Ito, Osaka (JP); Atsuko Onishi, Osaka (JP)

(73) Assignees: EDUCATIONAL FOUNDATION OF OSAKA MEDICAL AND PHARMACEUTICAL UNIVERSITY, Takatsuki (JP); TEIJIN LIMITED, Osaka (JP)

(*) Notice: Subject to any disclaimer, the term of this patent is extended or adjusted under 35 U.S.C. 154(b) by 110 days.

(21) Appl. No.: 16/068,488

(22) PCT Filed: Jan. 13, 2017

(86) PCT No.: PCT/JP2017/001063
§ 371 (c)(1),
(2) Date: Jul. 6, 2018

(87) PCT Pub. No.: WO2017/122795
PCT Pub. Date: Jul. 20, 2017

(65) Prior Publication Data
US 2019/0008623 A1    Jan. 10, 2019

(30) Foreign Application Priority Data

Jan. 14, 2016 (JP) .............................. JP2016-005593
Jun. 9, 2016 (JP) .............................. JP2016-115768

(51) Int. Cl.
*A61F 2/00* (2006.01)
*D04B 21/12* (2006.01)
(Continued)

(52) U.S. Cl.
CPC ............ *A61F 2/0063* (2013.01); *A61L 27/48* (2013.01); *A61L 27/52* (2013.01); *A61L 31/148* (2013.01);
(Continued)

(58) Field of Classification Search
CPC ............ A61F 2/0063; A61F 2250/0031; A61F 2002/0068; D04B 21/16; D04B 21/12;
(Continued)

(56) References Cited

U.S. PATENT DOCUMENTS 5,711,960 A    1/1998  Shikinami
8,414,508 B2   4/2013  Lecuivre et al.
(Continued)

FOREIGN PATENT DOCUMENTS

CN    101035574 A    9/2007
CN    101232908 A    7/2008
(Continued)

OTHER PUBLICATIONS

International Search Report, issued by International Searching Authority in corresponding International Application No. PCT/JP2017/001063, dated Apr. 18, 2017.
(Continued)

*Primary Examiner* — Peter Y Choi
*Assistant Examiner* — Jenna N Chandhok
(74) *Attorney, Agent, or Firm* — Sughrue Mion, PLLC

(57) ABSTRACT

The present invention provides a warp-knitted fabric and a medical material that can be simultaneously extended in all directions by causing thread made of a second bioabsorbable material to be absorbed in a living body over time and in
(Continued)

which the degree of extension can be increased. The present invention provides a warp-knitted fabric 10 in which adjacent loop rows are linked, the warp-knitted fabric 10 including: a plurality of first loop rows including a first thread and composed of continuous loops extending in the warp direction; and one or two or more second loop rows disposed between the first loop rows and composed of continuous loops extending in the warp direction, wherein each second loop row is formed of one or two or more loops solely including a second thread and one or two or more loops including the first thread, which are arranged alternately, at least three first loop rows are linked together by the first thread, and the bioabsorption rate of the first thread is lower than the bioabsorption rate of the second thread.

7 Claims, 44 Drawing Sheets

(51) Int. Cl.
  *D04B 21/16* (2006.01)
  *A61L 27/48* (2006.01)
  *A61L 27/52* (2006.01)
  *A61L 31/14* (2006.01)
(52) U.S. Cl.
  CPC ............ *D04B 21/12* (2013.01); *D04B 21/16* (2013.01); *A61F 2/0036* (2013.01); *A61F 2002/0068* (2013.01); *A61F 2250/0031* (2013.01); *D10B 2401/12* (2013.01); *D10B 2509/08* (2013.01)
(58) Field of Classification Search
  CPC ........ A61L 31/148; A61L 27/58; A61L 27/56; D10B 2401/12
  See application file for complete search history.

(56) References Cited

U.S. PATENT DOCUMENTS

| | | |
|---|---|---|
| 2004/0029478 A1 | 2/2004 | Planck et al. |
| 2007/0032805 A1 | 2/2007 | Therin et al. |
| 2010/0016872 A1 | 1/2010 | Bayon et al. |
| 2013/0267137 A1 | 10/2013 | Peniston et al. |
| 2013/0267972 A1* | 10/2013 | Peniston ............... A61F 2/0063 606/151 |

FOREIGN PATENT DOCUMENTS

| | | |
|---|---|---|
| CN | 104906620 A | 9/2015 |
| JP | 2001-137330 A | 5/2001 |
| JP | 2009-503281 A | 1/2009 |
| JP | 2014-531518 A | 11/2014 |
| JP | 5657249 B2 | 1/2015 |
| WO | 95/08354 A1 | 3/1995 |
| WO | 02/078568 A1 | 10/2002 |
| WO | 03/000305 A2 | 1/2003 |
| WO | 2004/043294 A1 | 5/2004 |
| WO | 2004/078067 A2 | 9/2004 |
| WO | 2005/105172 A1 | 11/2005 |
| WO | 2007/145974 A2 | 12/2007 |
| WO | 2008/069915 A2 | 6/2008 |
| WO | 2009/031035 A2 | 3/2009 |
| WO | 2013/026682 A1 | 2/2013 |
| WO | 2014/055480 A1 | 4/2014 |

OTHER PUBLICATIONS

Supplementary European Search Report dated Sep. 3, 2019 issued by the European Patent Office in counterpart application No. 17738547.3.

* cited by examiner 2 1 2 1 2 1 2 1 2 1 2 1 2

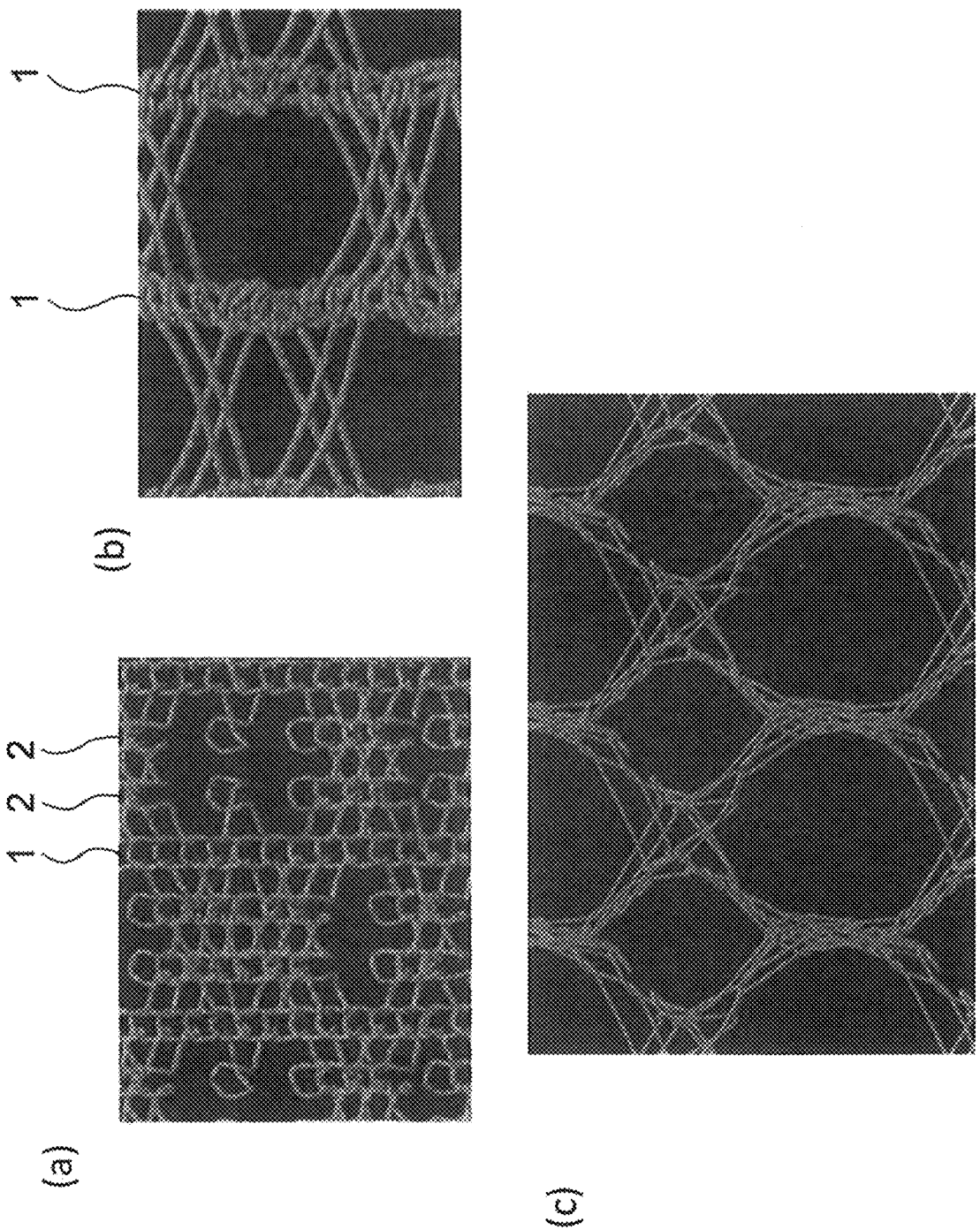

FIG. 24
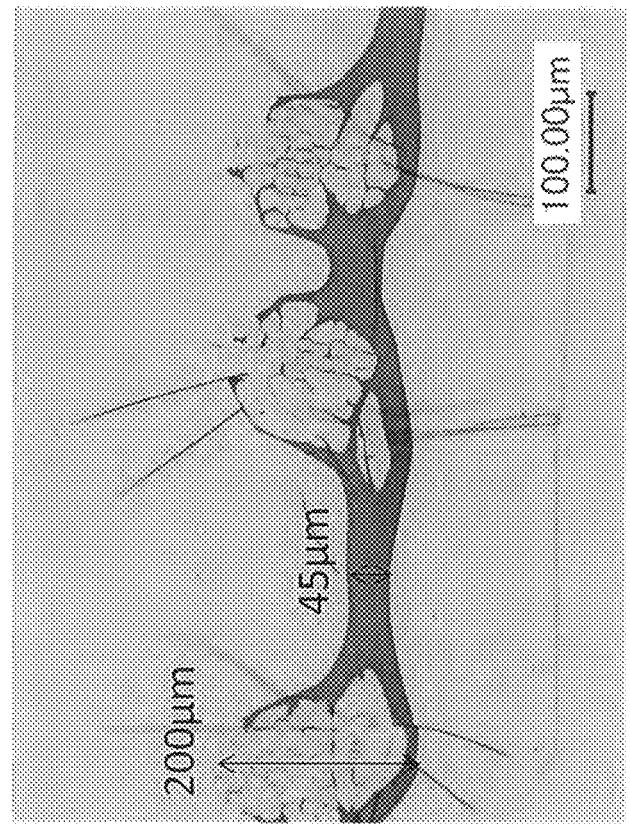
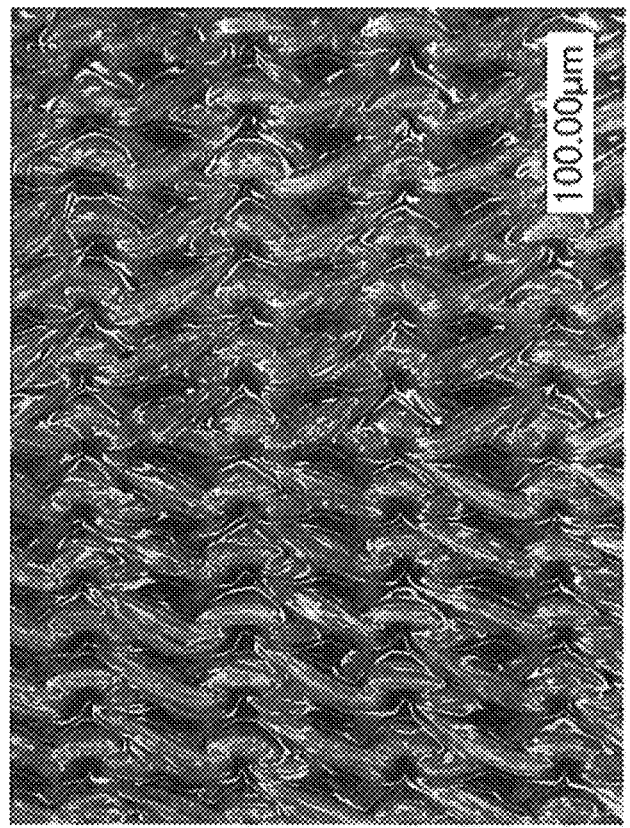

FIG. 25
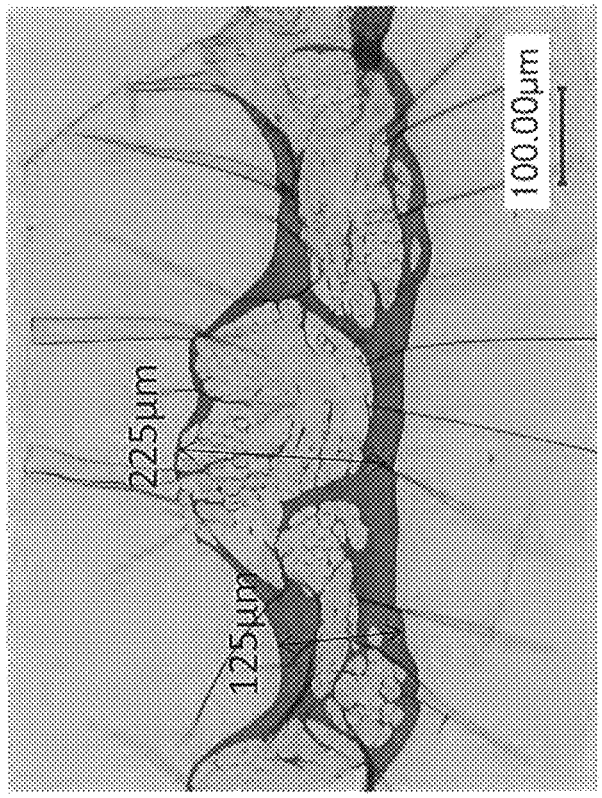
(b)
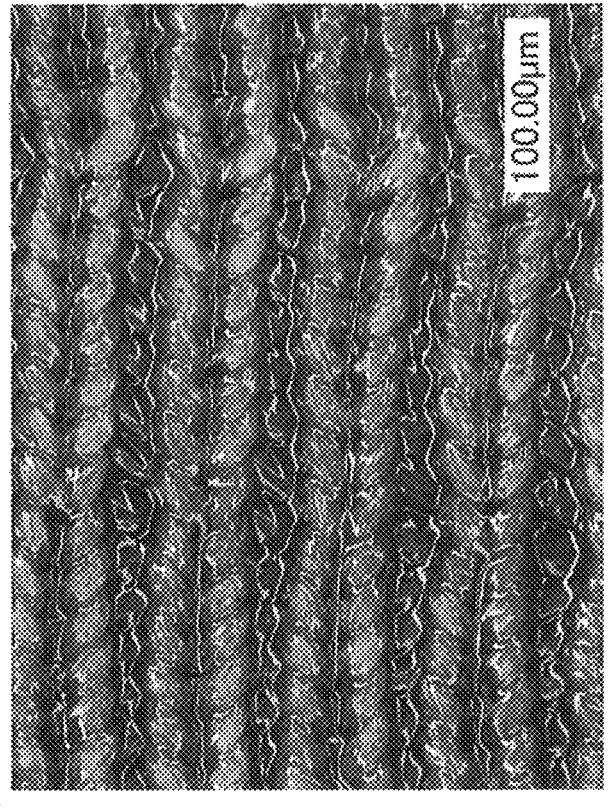
(a)

WARP-KNITTED FABRIC AND MEDICAL MATERIAL

CROSS REFERENCE TO RELATED APPLICATIONS

This application is a National Stage of International Application No. PCT/JP2017/001063, filed Jan. 13, 2017, claiming priority based on Japanese Patent Application No. 2016-005593, filed Jan. 14, 2016, and Japanese Patent Application No. 2016-115768, filed Jun. 9, 2016.

FIELD

The present invention relates to a warp knitted fabric and a medical material. In particular, the present invention relates to a warp knitted fabric for use in a living organism in the medical field, and a medical material comprising the warp knitted fabric. The present invention also relates to a method of sealing a fabric, and a sealed fabric.

BACKGROUND

Some fabrics such as woven and knitted fabrics used in the medical field exhibit biocompatibility, and the fabric is relatively easily processed into the material, and therefore such a biocompatible fabric is used for a medical material.

In particular, highly functional fabrics have recently been developed for medical applications.

For example, PTL 1 discloses a mesh for use in an implantable sling. The mesh includes a plurality of non-biodegradable transverse strands and a plurality of non-biodegradable longitudinal strands arranged in a grid, and a biodegradable fiber incorporated into the strands. Pores/interstitial gaps in the sling enlarge with degradation of the fiber, and this enlargement assists tissue in-growth and scar tissue formation.

PTL 2 discloses a polymeric mesh for use in medical implantation. The polymeric mesh includes an absorbable polymeric fiber and a non-absorbable polymeric fiber knitted together. The polymeric mesh provides an early stiff phase (due to the presence of both the absorbable polymeric fiber and the non-absorbable polymeric fiber) and a later extensible phase (after the degradation of the absorbable polymeric fiber).

CITATION LIST

Patent Literature

PTL 1: Japanese Patent No. 5657249
PTL 2: US Patent Application Publication No. 2013/0267137

SUMMARY

Technical Problem to be Solved by Invention

Unfortunately, the mesh disclosed in PTL 1, which is a woven fabric, insufficiently expands even after complete decomposition of the biodegradable fiber. Thus, if the mesh is used for reinforcing a sutured portion of an organ in surgery, the mesh may fail to follow an increase in size of the organ in association with the gradual growth of the organ in the human body.

In the polymeric mesh disclosed in PTL 2, in the mesh structure after dissolution of the absorbable polymeric fiber, the weft-direction linkage of the absorbable polymeric fiber is eliminated but the warp-direction linkage of the non-absorbable polymeric fiber is maintained. The resultant mesh structure exhibits mere expansion of the original knitted fabric; hence, the knitted fabric cannot be expanded in all directions simultaneously. Thus, even if the absorbable polymeric fiber is dissolved, weft-direction expansion of the fabric leads to warp-direction contraction of the fabric, and vice versa as in the case before dissolution of the absorbable polymeric fiber. Since the polymer mesh cannot be expanded in all directions simultaneously, the polymer mesh may fail to follow an increase in size of an organ in all directions, as in the problems involved in the mesh disclosed in PTL 1.

In view of the foregoing, an object of the present invention is to provide a warp knitted fabric composed of two types of yarns, the fabric being expandable in all directions simultaneously through absorption of a bioabsorbable yarn exhibiting a higher bioabsorption rate in a living organism over time, wherein the degree of expansion can be increased. Another object of the present invention is to provide a medical material comprising the warp knitted fabric. Still another object of the present invention is to provide a method of sealing a fabric with a hydrogel to prevent permeation of a fluid such as blood through the fabric. Yet another object of the present invention is to provide a sealed fabric.

Means for Solving Problem

The present inventors have conducted extensive studies and have found that the aforementioned problems can be solved by a warp knitted fabric comprising a plurality of first loop columns, each including a group of consecutive loops in a warp direction, and the first loops comprising a first yarn, and one or more second loop columns, each including a group of consecutive loops in a warp direction and the second loop columns comprise loops of only a second yarn having a bioabsorption rate higher than that of the first yarn, wherein the first loop columns and the second loop columns being arranged in a predetermined pattern. The present inventors have also found that the aforementioned problems can be solved by sealing of a fabric under specific conditions. The present invention has been accomplished on the basis of these findings. The present invention includes the following aspects.

Aspect (1) of the present invention provides a warp knitted fabric comprising:

a plurality of first loop columns, each comprising a group of consecutive loops in a warp direction, the first loops comprising a first yarn; and one or more second loop columns, each comprising a group of consecutive loops in a warp direction, and being disposed between the first loop columns, wherein, the second loos columns comprising one or more loops of only a second yarn and one or more loops comprising the first yarn, the loops of the second yarn and the loops comprising the first yarn being alternately disposed, any two adjacent loop columns of the first and/or second loop columns are linked together;

at least three first loop columns are linked together with the first yarn; and the first yarn has a bioabsorption rate lower than that of the second yarn.

Aspect (2) of the present invention provides the warp knitted fabric according to Aspect (1), wherein the first yarn is composed of a non-bioabsorbable material and the second yarn is composed of a bioabsorbable material.

Aspect (3) of the present invention provides the warp knitted fabric according to Aspect (1) or (2), wherein one to five of the second loop columns are disposed between the first loop columns.

Aspect (4) of the present invention provides the warp knitted fabric according to any one of Aspects (1) to (3), wherein the first and/or second yarn is a multifilament yarn.

Aspect (5) of the present invention provides the warp knitted fabric according to any one of Aspects (1) to (4), for use in a medical material.

Aspect (6) of the present invention provides a medical material comprising the warp knitted fabric according to any one of Aspects (1) to (4), wherein at least one surface of the warp knitted fabric is coated with a hydrogel, or a space between yarns of the warp knitted fabric is filled with the hydrogel.

Aspect (7) of the present invention provides the medical material according to Aspect (6), wherein the hydrogel is gelatin and/or collagen.

The preset invention also provides a sealed fabric satisfying the following relations:

$$50 \leq X \leq 80, 1.4 \leq Y \leq 6.0, \text{ and } 414 \leq Z \leq 1,028 \quad [F1]$$

where X represents the fabric areal weight (g/m$^2$), Y represents the weight of hydrogel coating per unit area (mg/cm$^2$), and Z represents the swelling (%) of the hydrogel.

The present invention is also to provide a sealed fabric in which the fabric areal weight (g/m$^2$) (X), the weight of hydrogel coating per unit area (mg/cm$^2$) (Y), and the swelling (%) of the hydrogel (Z) in an orthogonal coordinate system (X, Y, Z), are present on edges and in the inner space of a polyhedron having the following vertices: point A (50, 6, 700), point B (50, 6, 800), point C (50, 4, 800), point D (50, 4, 700), point E (70, 6.2, 459), point F (70, 6.2, 965), point G (70, 1.6, 965), point H (70, 1.6, 459), point I (72, 4.9, 826), point J (72, 4.9, 1028), point K (72, 1.7, 1028), and point L (72, 1.7, 826).

Effects of Invention

The warp knitted fabric of the present invention, which has a warp knitting pattern, has a sufficiently dense structure. The warp knitted fabric can be expanded in all directions simultaneously through decomposition and absorption of the yarn having a higher bioabsorption rate, of the two yarns composed of the bioabsorbable material contained in the warp knitted fabric. Thus, the expansion of the fabric in one direction does not cause the contraction of the fabric in the other direction.

In the warp knitted fabric of the present invention, the first yarn has a bioabsorption rate lower than that of the second yarn; each first loop column comprises a group of consecutive loops comprising the first yarn in a warp direction; each second loop column comprises a group of consecutive loops comprising one or more loops of only the second yarn and one or more loops comprising the first yarn, the loops of the second yarn and the loops of the first yarn being alternately disposed in a warp direction; one or more second loop columns are disposed between the first loop columns; and at least three first loop columns are linked together with the first yarn. Thus, the warp knitted fabric exhibits a strength enough to prevent the separation or breakage of the fabric itself in all directions and a high degree of expansion in all directions even after decomposition and absorption of the second yarn.

If the warp knitted fabric of the present invention is used, for example, as a filling material for suture and implantation in surgery, the warp knitted fabric strongly supports a sutured portion at an early stage and exhibits a strength enough not to be broken at the stage of decomposition and absorption of the yarn of the bioabsorbable material. In addition, the warp knitted fabric can follow an increase in size of the sutured organ in association with the gradual growth of the human body.

The warp knitted fabric of the present invention exhibits further improved strength and expansion in all directions after decomposition of the bioabsorbable material if one to five second loop columns are disposed between the first loop columns.

The warp knitted fabric of the present invention exhibits a soft texture if the yarn is a multifilament yarn. The use of a multifilament yarn in a living organism is advantageous in terms of tissue regeneration because cellular tissues or microvessels are allowed to infiltrate tomonofilaments.

The sealing process of the present invention is suitable for use in the production of a medical material because the process requires only a simple operation and can prevent permeation of a fluid such as blood through the fabric.

The warp knitted fabric or sealed fabric of the present invention is suitable for use as a medical material. Specifically, the warp knitted fabric or the sealed fabric is suitable for use as a cardiac-repair patch, i.e., a restorative for a defected or stenotic portion of an infant heart.

The medical material of the present invention can prevent leakage of a fluid such as blood through the warp knitted fabric if at least one surface of the fabric is coated with a hydrogel or a space between yarns of the fabric is filled with the hydrogel. The medical material of the present invention involves successful replacement of the hydrogel with tissue in a living organism. The use of the medical material of the present invention results in successful regeneration of smooth muscle and small vessels through tissue replacement. The medical material also reduces calcification by calcium deposition.

The medical material exhibits superior versatility and biocompatibility if the hydrogel is gelatin and/or collagen.

The warp knitted fabric of the present invention comprises a plurality of first loop columns each comprising a group of consecutive loops in a warp direction and the first loops comprises the first yarn, and a plurality of second loop columns each comprising a group of consecutive loops in a warp direction and the second loop columns comprise loops only the second yarn, which has a bioabsorption rate higher than that of the first yarn, such that first loop columns and second loop columns are knitted in a specific arrangement. In a preferred embodiment, the warp knitted fabric of the present invention is composed of a yarn of a non-bioabsorbable material and a yarn of a bioabsorbable material (hereinafter this embodiment may be referred to as "first embodiment").

The preferred embodiment of the present invention (first embodiment) be mainly described below with reference to the drawings as appropriate.

The same components are denoted by the same reference numerals in the drawings, and redundant description thereof is omitted. Unless otherwise specified, positional relationships such as vertical and horizontal positional relationships are based on those illustrated in the drawings. The dimensional proportions in the drawings do not necessarily correspond to actual dimensional proportions.

BRIEF DESCRIPTION OF DRAWINGS

FIG. 5(a) is a front view of the warp knitted fabric according to the first embodiment after decomposition and absorption of the yarn of the bioabsorbable material, FIG. 5(b) is a partial enlarged view of the state of expansion of the warp knitted fabric in a weft direction, and FIG. 5(c) is a partial enlarged view of the state of expansion of the weft-expanded warp knitted fabric in a warp direction.

FIG. 24(a) is a micrograph of the top surface of a medical material prepared in Example 14, and FIG. 24(b) is a photograph of a cross section of the medical material.

FIG. 25(a) is a micrograph of the top surface of a medical material prepared in Example 15, and FIG. 25(b) is a photograph of a cross section of the medical material.

DESCRIPTION OF EMBODIMENTS

As used herein, the term "bioabsorbable" refers to the property such that a yarn composed of a bioabsorbable material is eliminated through decomposition and absorption by tissues in a living organism over time according to the chemical property, etc., of the material. As used herein, the term "bioabsorption rate" refers to the rate at which a yarn for use in the warp knitted fabric of the present invention is decomposed and absorbed in a living organism, i.e., the period during which a unit amount of yarn is decomposed and absorbed in a living organism.

[Warp Knitted Fabric]

The warp knitted fabric of the present invention will now be described.

As used herein, the "loop column" of the warp knitted fabric refers to a group of consecutive loops disposed in a warp direction.

Figure 1A:
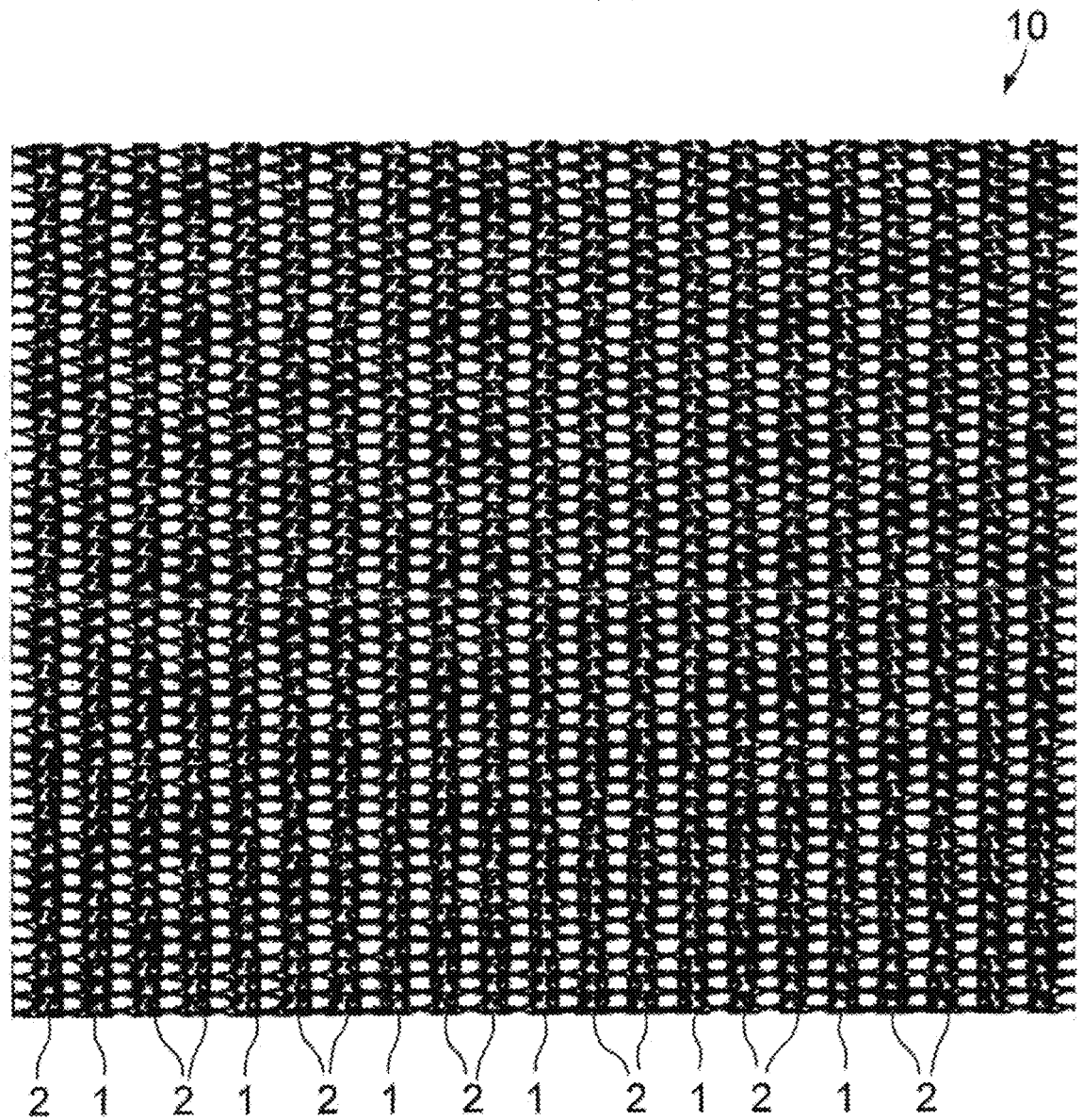
FIG. 1(a) is a front view of a warp knitted fabric according to a first embodiment.
Figure 1B:
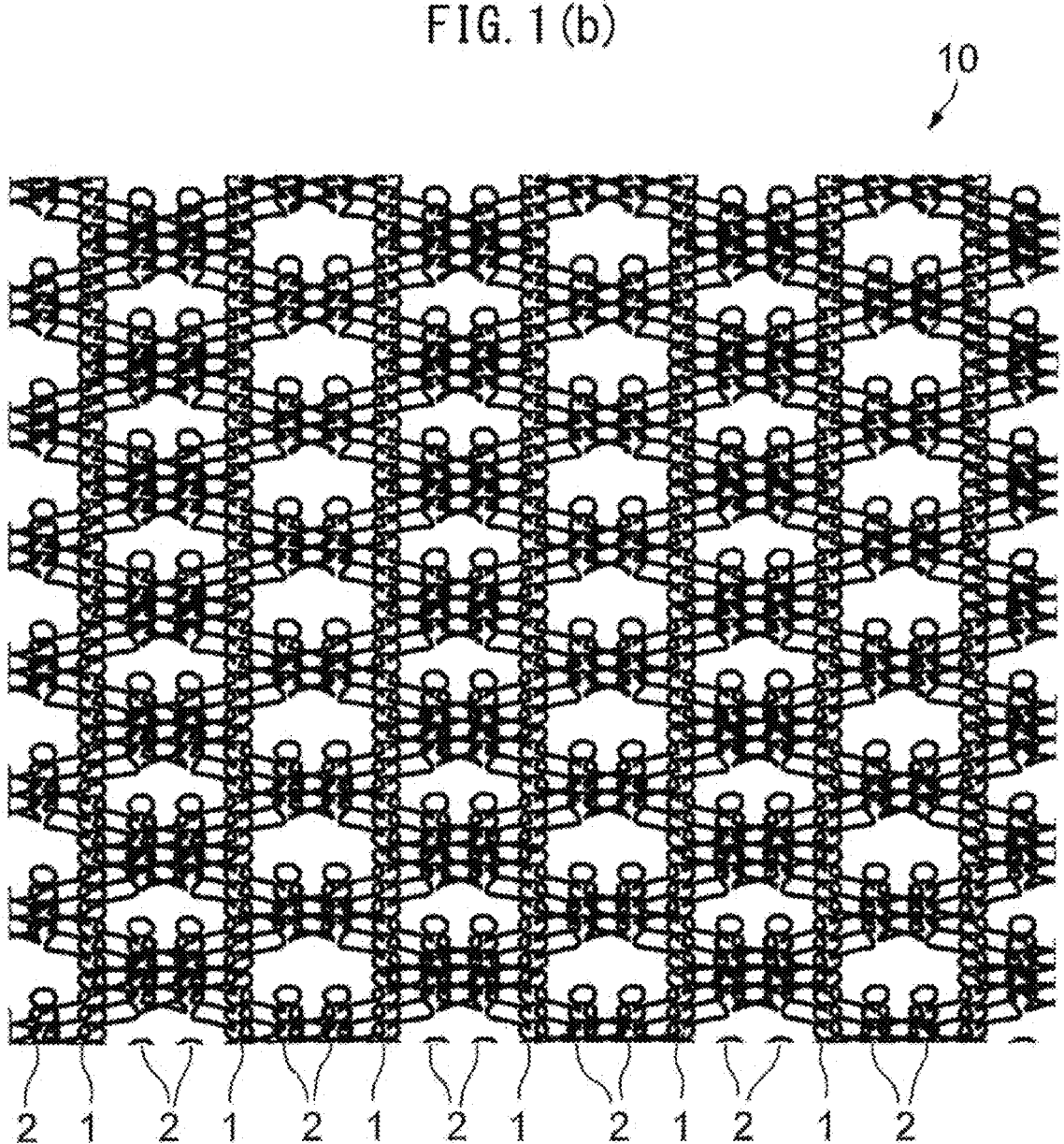
FIG. 1(b) is a front view of the state after decomposition and absorption of a yarn of a bioabsorbable material of the warp knitted fabric illustrated in FIG. 1(a).
Figure 2:
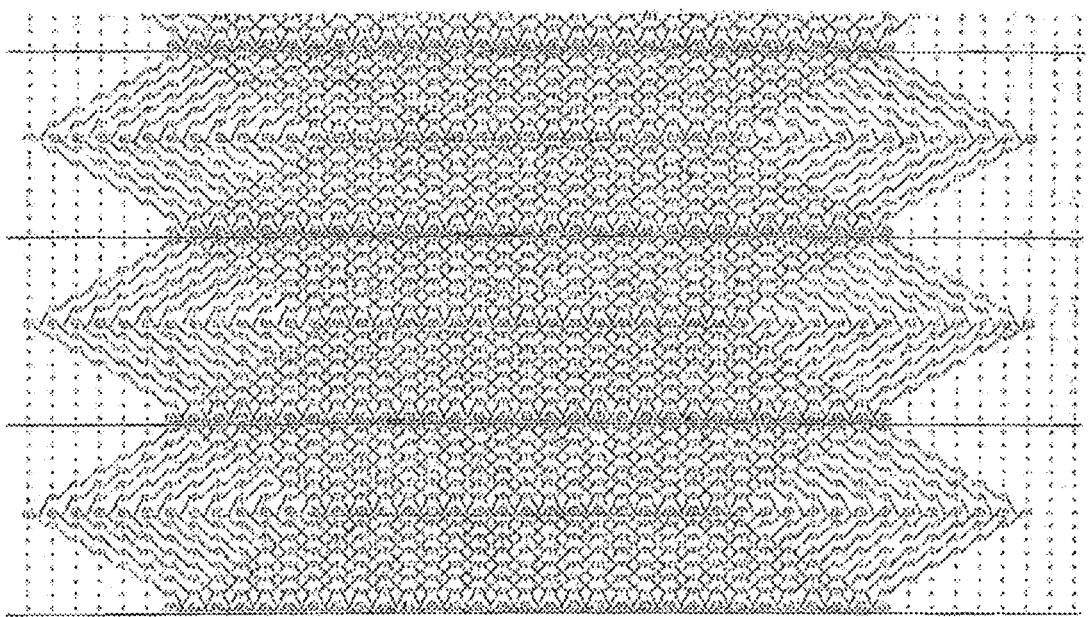
FIG. 2 illustrates a knitting pattern of the warp knitted fabric illustrated in FIG. 1(a).

FIG. 1(a) is a front view of a warp knitted fabric according to a first embodiment. FIG. 1(b) is a front view of the state of the warp knitted fabric illustrated in FIG. 1(a) after decomposition and absorption of a yarn of a bioabsorbable material. FIG. 2 illustrates a knitting pattern of the warp knitted fabric illustrated in FIG. 1(a).

As illustrated in FIG. 1(a), the warp knitted fabric 10 according to the first embodiment includes a plurality of first loop columns 1 disposed at regular intervals and a plurality of second loop columns 2 such that each column is composed of a group of consecutive loops disposed in a warp direction and two second loop columns 2 are disposed between the first loop columns 1.

In the warp knitted fabric 10, which has a warp knitting pattern as illustrated in FIG. 2, adjacent loop columns, i.e., a first loop column 1 and an adjacent second loop column 2, or adjacent second loop columns 2, are linked to each other.

The warp knitted fabric 10, which has a warp knitting pattern, has a sufficiently dense structure. The warp knitted fabric can be expanded in all directions simultaneously through decomposition and absorption of the yarn of the bioabsorbable material described below. As used herein, the term "all directions" refers to all directions of the same plane as the warp knitted fabric.

As illustrated in FIG. 1(b), the yarn of the bioabsorbable material in the warp knitted fabric 10 according to the first embodiment is eliminated through decomposition and absorption in a living organism over time. Specifically, loops consisting of the yarn of the bioabsorbable material are eliminated from the second loop columns 2, and loops consisting of the yarn of the non-bioabsorbable material remain in the first loop columns 1 and the second loop columns 2. The expansion of the fabric through decomposition and absorption of the yarn of the bioabsorbable material will be described below.

Each of the first loop columns 1 includes a plurality of loops that consist of the yarn of the non-bioabsorbable material and that are linked in a warp direction.

Each of the second loop columns 2 includes a plurality of loops consisting of the yarn of the bioabsorbable material and a plurality of loops consisting of the yarn of the non-bioabsorbable material such that these two types of loops are alternately linked in a warp direction.

Figure 3A:
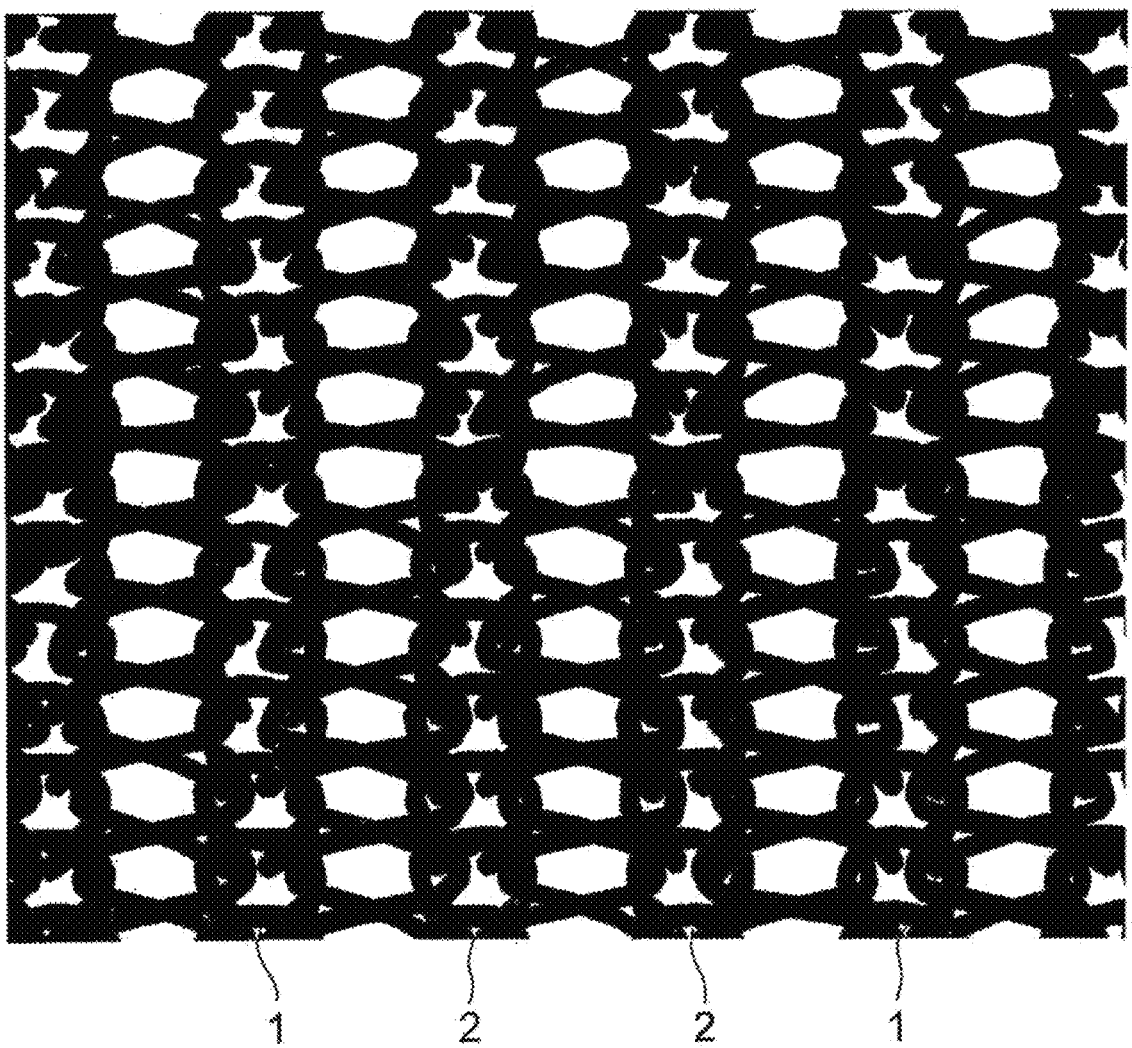
FIG. 3(a) is a partial enlarged view of FIG. 1(a).
Figure 3B:
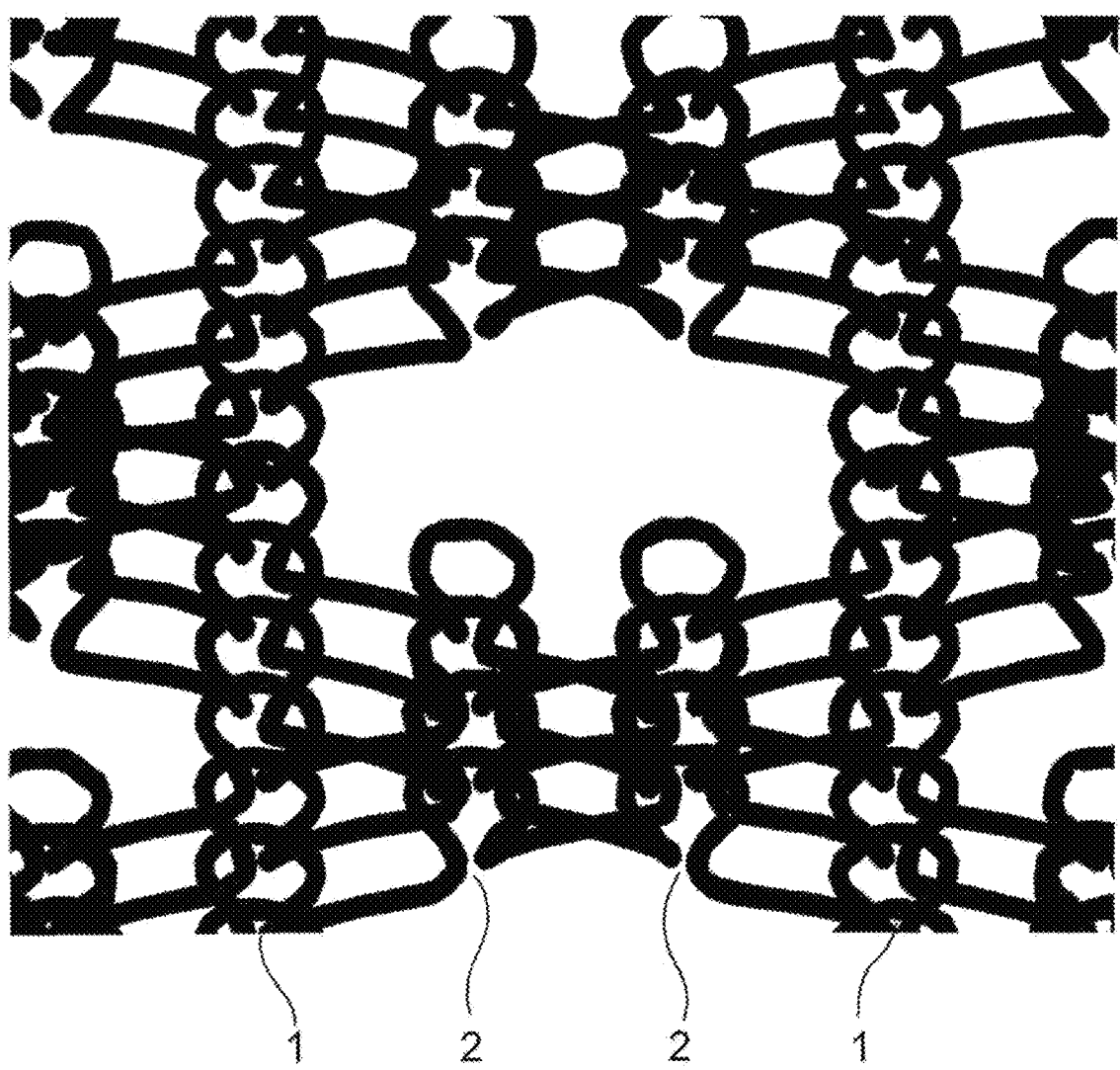
FIG. 3(b) is a partial enlarged view of FIG. 1(b).

FIG. 3(a) is a partial enlarged view of FIG. 1(a), and FIG. 3(b) is a partial enlarged view of FIG. 1(b).

As illustrated in FIGS. 3(a) and 3(b), two second loop columns 2 are disposed between adjacent first loop columns 1. Thus, the warp knitted fabric 10 includes first loop columns 1 and second loop columns 2 in a proportion of 1:2, i.e., the warp knitted fabric 10 is composed of continuously and repeatedly disposed units each including one first loop column 1 and two second loop columns 2. As described below, the proportion of first loop columns 1 and second loop columns 2 in the warp knitted fabric 10 can be modified to vary the shape and expansion of the warp knitted fabric after decomposition and absorption of the yarn of the bioabsorbable material.

First loop columns 1 are disposed at regular intervals and are linked together with the yarn of the non-bioabsorbable material forming some second loop columns. As illustrated in FIG. 3(b), first loop columns 1 are linked together with the yarn of the non-bioabsorbable material, that is not biologically decomposed or absorbed, even after decomposition and absorption of the yarn of the bioabsorbable material in a living organism.

At least three first loop columns need to be linked together from the viewpoint of the strength of the warp knitted fabric. This structure can maintain a sufficient strength without breakage over a long period of time.

Each second loop column 2 includes a plurality of loops consisting of the yarn of the non-bioabsorbable material that links first loop columns 1 together, and a plurality of loops consisting of the yarn of the bioabsorbable material.

Each second loop column 2 may include any number of loops consisting of the yarn of the non-bioabsorbable material and any number of loops consisting of the yarn of the bioabsorbable material.

Loops consisting of the yarn of the non-bioabsorbable material and loops consisting of the yarn of the bioabsorbable material may be alternately disposed in any proportion.

The number and proportion of these two types of loops in a second loop column 2 may be identical to or different from those in the adjacent second loop column 2.

Figure 4A:
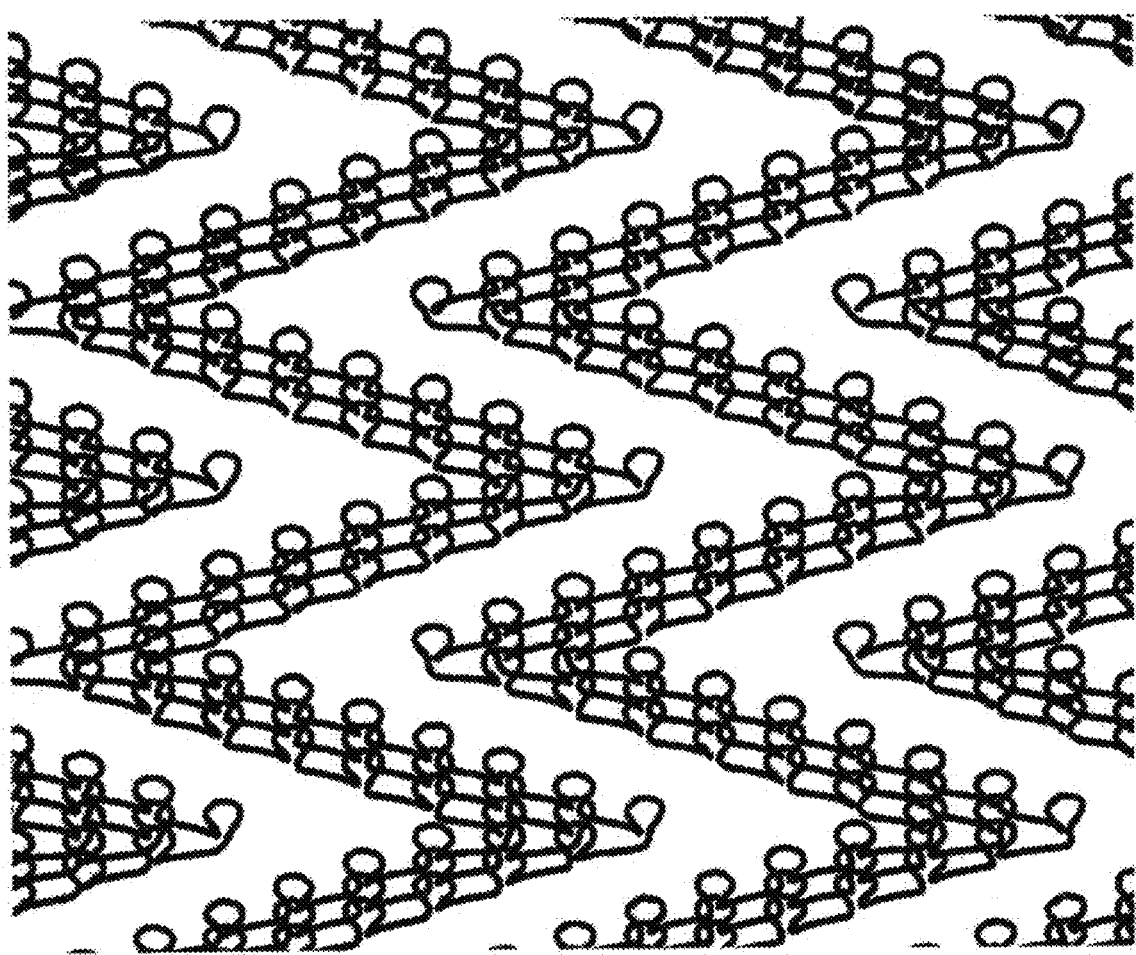
FIG. 4(a) illustrates an open-loop pattern of the warp knitted fabric illustrated in FIG. 1(a) or FIG. 1(b).

FIG. 4(a) illustrates an open loop pattern of the warp knitted fabric illustrated in FIG. 1(a) or FIG. 1(b), and FIG.

4(b) illustrates a closed-loop pattern of the warp knitted fabric illustrated in FIG. 1(a) or FIG. 1(b).

Figure 4B:
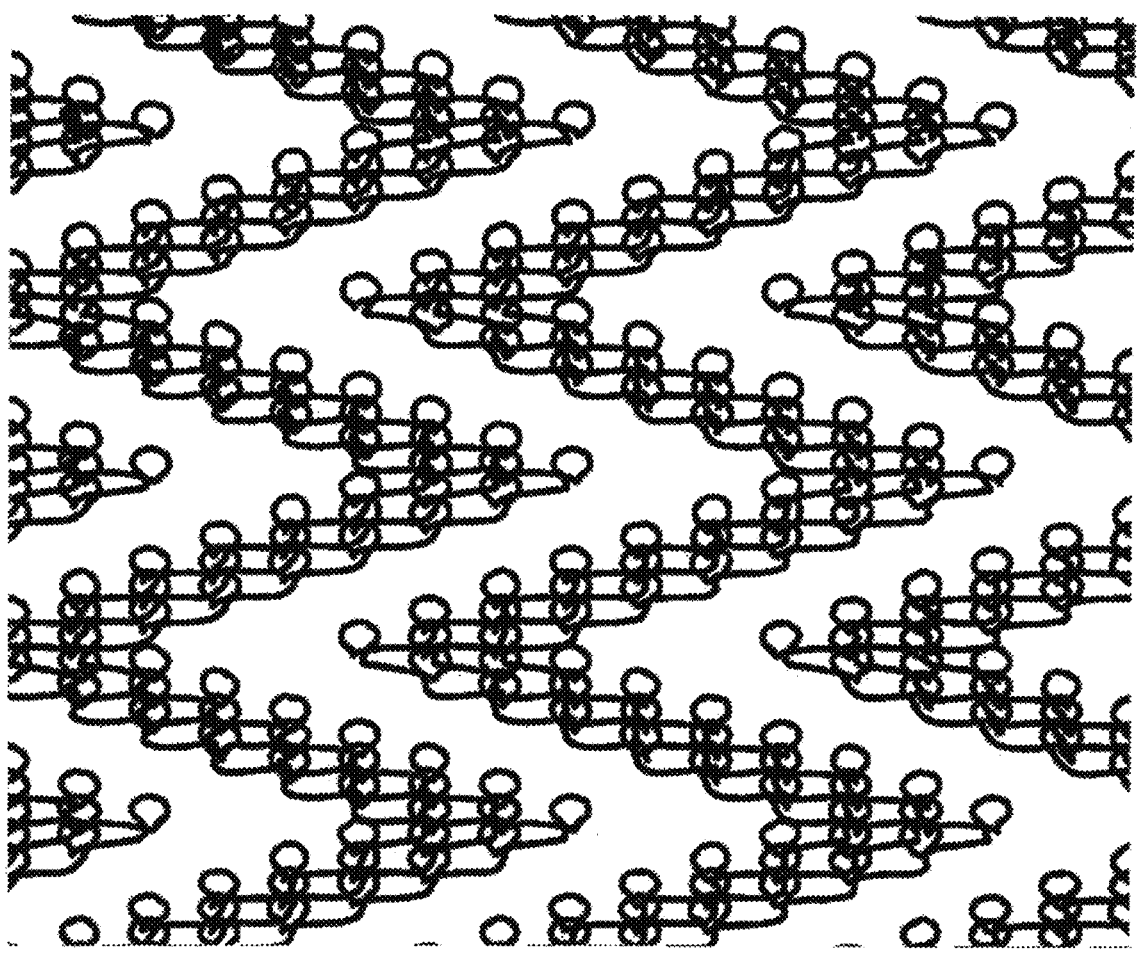
FIG. 4(b) illustrates a closed-loop pattern of the warp knitted fabric illustrated in FIG. 1(a) or FIG. 1(b).

As illustrated in FIGS. 4(a) and 4(b), a yarn of the non-bioabsorbable or bioabsorbable material forms a plurality of loops while zigzagging in the warp knitted fabric 10.

Another yarn of the non-bioabsorbable or bioabsorbable material also forms loops while zigzagging in the warp knitted fabric. These loops are linked together in a weft direction to form the warp knitted fabric.

Thus, the yarn of the non-bioabsorbable material forms first loop columns 1, and loops that link first loop columns 1 together, a portion of second loop columns 2.

The yarn of the bioabsorbable material also forms a portion of second loop columns 2 by linking turned edges of the zigzagged yarn of the non-bioabsorbable material.

In this case, the weave of loops may be in the pattern of open loops (see FIG. 4(a)) or closed loops (see FIG. 4(b)). The warp knitted fabric 10 according to the first embodiment is in the pattern of open loops.

The arrangement of loop columns (described below) and the aforementioned open-loops or closed-loops pattern can be appropriately determined in the warp knitted fabric 10 to vary the shape and expansion of the warp knitted fabric 10 after decomposition and absorption of the yarn of the bioabsorbable material.

As illustrated in FIGS. 3(a) and 3(b), the warp knitted fabric 10 has a structure such that a portion of second loop columns 2 is eliminated through decomposition and absorption of the yarn of the bioabsorbable material in a living organism. Specifically, the yarn of the bioabsorbable material in the warp knitted fabric 10 illustrated in FIG. 3(a) is gradually decomposed and absorbed in a living organism and eventually eliminated to form a weave illustrated in FIG. 3(b), resulting in an increase in the expansion of the warp knitted fabric 10. The elimination of the yarn of the bioabsorbable material may occur in parallel with the expansion of the warp knitted fabric in a living organism.

In the case of elimination of the yarn of the bioabsorbable material, the aforementioned arrangement and linkage of first loop columns 1 and second loop columns 2 can provide the warp knitted fabric with a strength enough to prevent the separation or breakage of the fabric in all directions and can significantly increase the degree of expansion of the fabric in all directions.

FIG. 5(a) is a front view of the warp knitted fabric according to the first embodiment after decomposition of the yarn of the bioabsorbable material. FIG. 5(b) is a partial enlarged view of the state of expansion of the warp knitted fabric in a weft direction. FIG. 5(c) is a partial enlarged view of the state of expansion of the weft-expanded warp knitted fabric in a warp direction.

If the warp knitted fabric 10 is expanded in a weft direction after decomposition and absorption of the yarn of the bioabsorbable material as illustrated in FIGS. 5(a) and 5(b), loops of second loop columns 2 consisting of the yarn of the non-bioabsorbable material are expanded into a straight shape.

If the warp knitted fabric 10 is expanded in a warp direction after decomposition and absorption of the yarn of the bioabsorbable material as illustrated in FIG. 5(c), loops of first loop columns 1 consisting of the yarn of the non-bioabsorbable material are expanded into a straight shape.

Since the warp knitted fabric 10 can be expanded in warp and weft directions independently, the expansion of the fabric in one direction does not cause the contraction of the fabric in the other direction. Thus, the warp knitted fabric can be expanded in all directions simultaneously.

The present invention should not be limited to the preferred embodiment described above.

In the warp knitted fabric 10 according to the first embodiment, each first loop column 1 includes a plurality of loops consisting of the yarn of the non-bioabsorbable material and linked in a warp direction. The loops may contain a yarn other than the yarn of the non-bioabsorbable material so long as the structure of linked first loop columns 1 can be maintained after elimination of the yarn of the bioabsorbable material in a living organism.

In the warp knitted fabric 10 according to the first embodiment, first loop columns 1 are linked together with a plurality of loops of second loop columns 2 consisting of the yarn of the non-bioabsorbable material. First loop columns 1 may be linked together with a yarn composed of another non-bioabsorbable material.

Each second loop column 2, which includes a plurality of loops consisting of the yarn of the bioabsorbable material, may be composed of one loop consisting of the yarn of the bioabsorbable material. Each second loop column 2, which also includes a plurality of loops consisting of the yarn of the non-bioabsorbable material, may be composed of one loop consisting of the yarn of the non-bioabsorbable material. Thus, each second loop column may include one or more loops consisting of the yarn of the bioabsorbable material and one or more loops consisting of the yarn of the non-bioabsorbable material such that these two types of loops are alternately linked.

The warp knitted fabric 10 according to the first embodiment includes first loop columns 1 and second loop columns 2 in a proportion of 1:2; however, first loop columns 1 and second loop columns 2 may be disposed in any proportion.

In the warp knitted fabric 10, two second loop columns 2 are disposed between adjacent first loop columns 1. Any number of second loop columns 2, however, may be disposed between adjacent first loop columns 1.

Preferably, one to five second loop columns 2 are disposed between adjacent first loop columns 1. In this case, the warp knitted fabric exhibits improved strength and expansion in all directions.

Figure 6A:
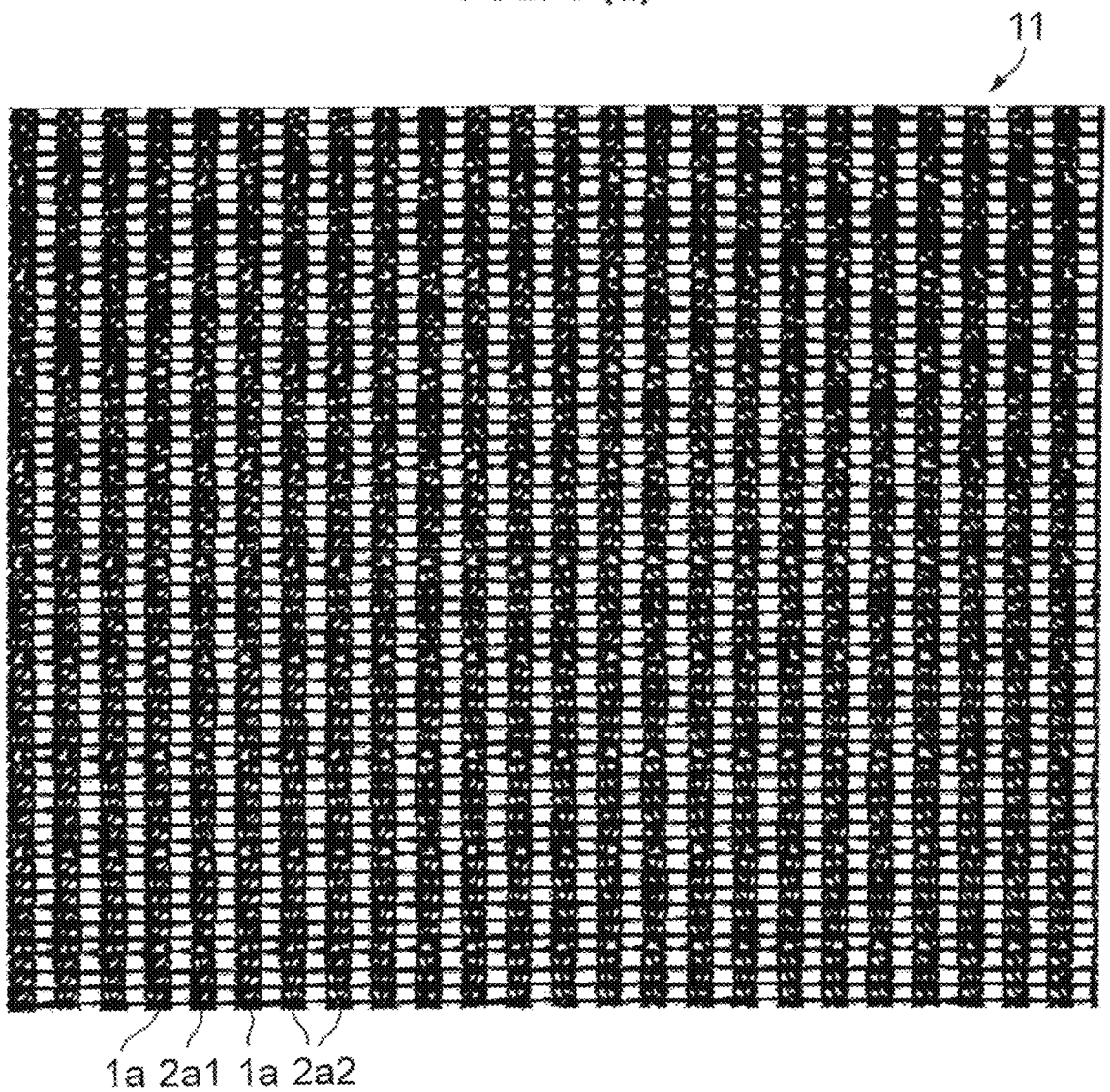
FIG. 6(a) is a front view of another warp knitted fabric according to the first embodiment.
Figure 6B:
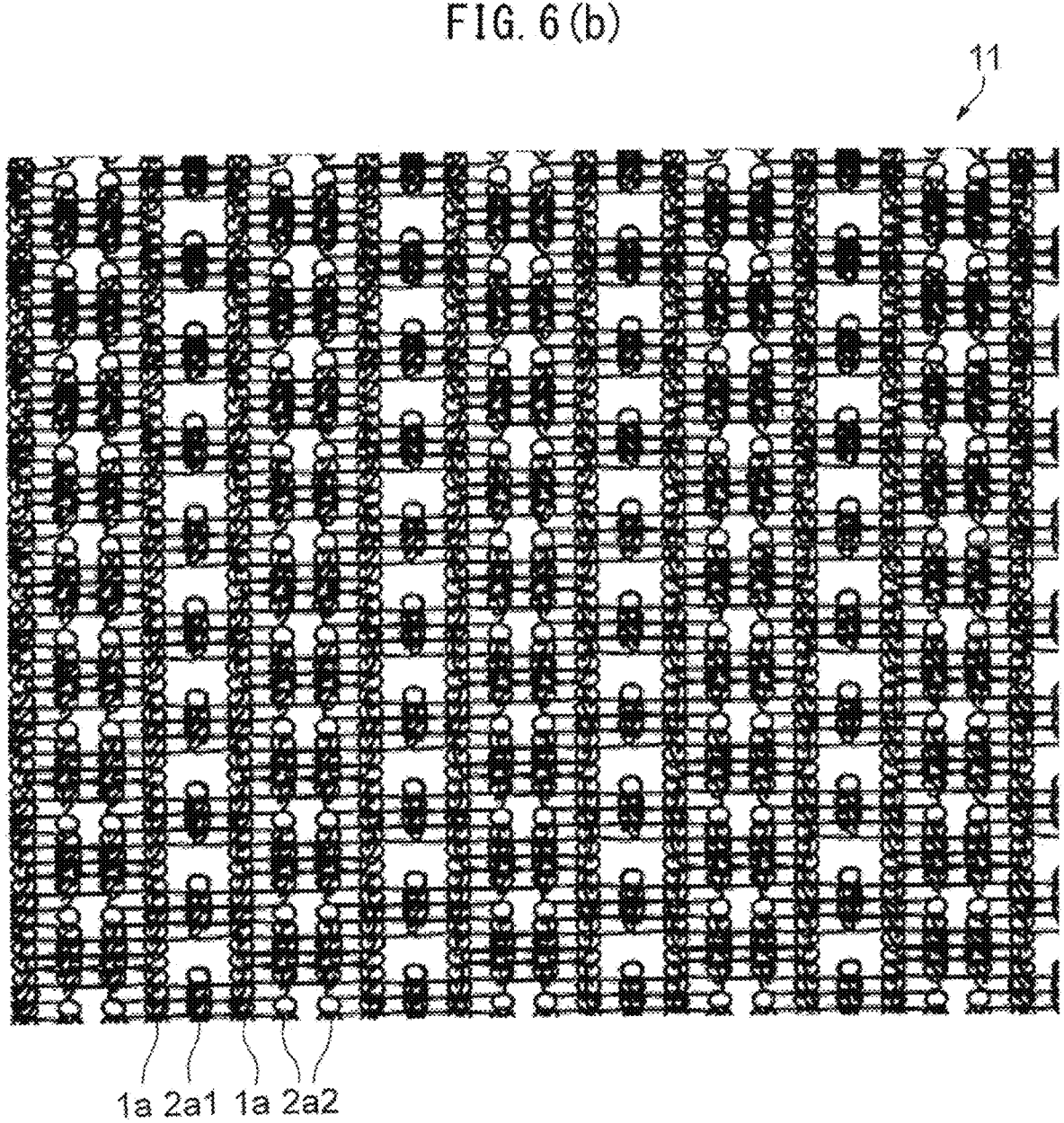
FIG. 6(b) is a front view of the state after decomposition and absorption of a yarn of a bioabsorbable material of the warp knitted fabric illustrated in FIG. 6(a).

FIG. 6(a) is a front view of another warp knitted fabric according to the first embodiment. FIG. 6(b) is a front view of the state after decomposition and absorption of a yarn of a bioabsorbable material of the warp knitted fabric illustrated in FIG. 6(a).

The warp knitted fabric 11 illustrated in FIGS. 6(a) and 6(b) is in the pattern of open loop. The warp knitted fabric 11 is composed of continuously and repeatedly disposed units each including one first loop column 1a, one second loop column 2a1, one first loop column 1a, and two second loop columns 2a2. Thus, the warp knitted fabric 11 includes first loop columns 1a, second loop columns 2a1, first loop columns 1a, and second loop columns 2a2 in a proportion of 1:1:1:2.

Figure 7A:
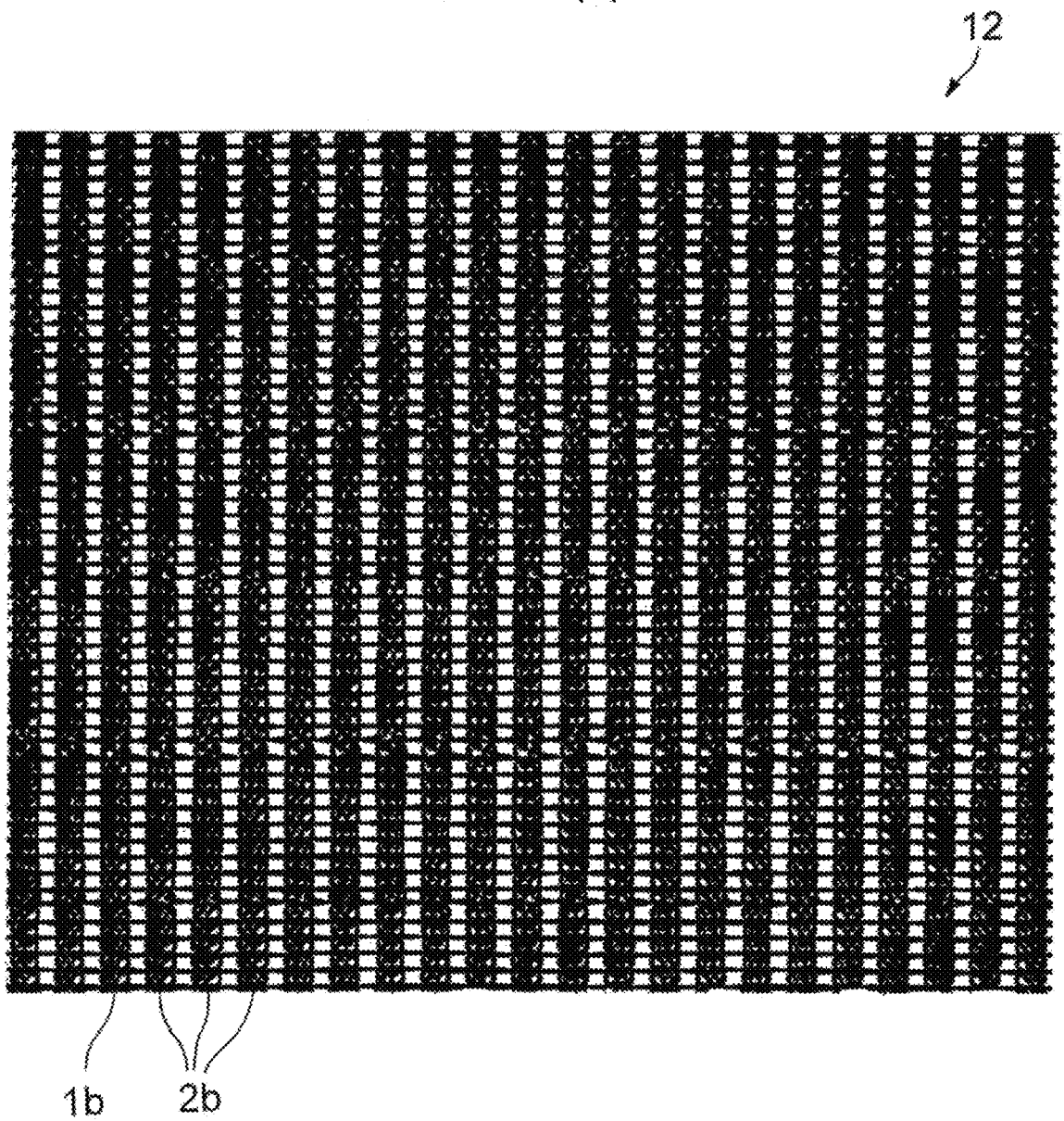
FIG. 7(a) is a front view of a warp knitted fabric according to a second embodiment.
Figure 7B:
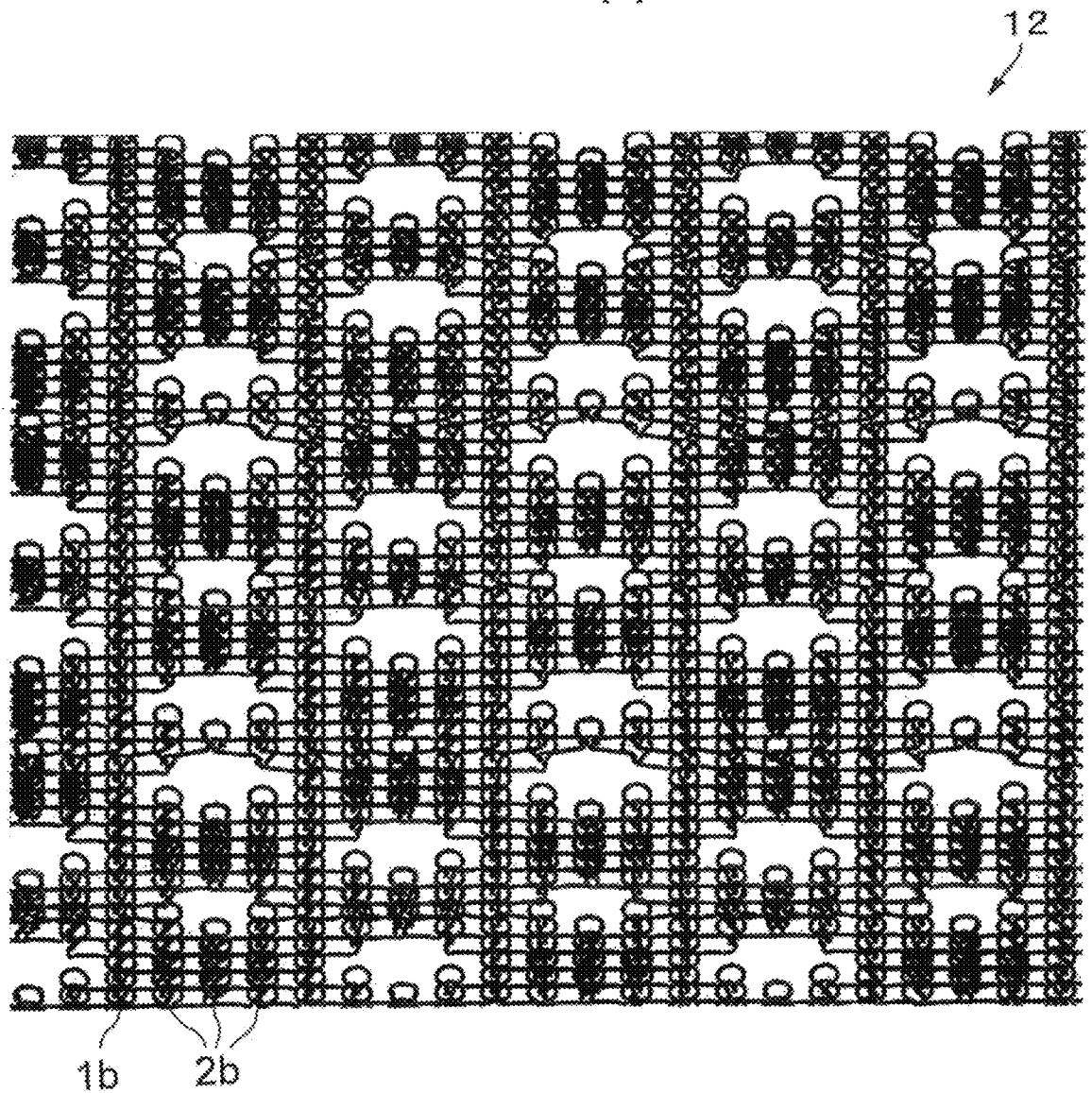
FIG. 7(b) is a front view of the state after decomposition and absorption of a yarn of a bioabsorbable material of the warp knitted fabric illustrated in FIG. 7(a).

FIG. 7(a) is a front view of a warp knitted fabric according to a second embodiment. FIG. 7(b) is a front view of the state after decomposition and absorption of a yarn of a bioabsorbable material of the warp knitted fabric illustrated in FIG. 7(a).

The warp knitted fabric 12 illustrated in FIGS. 7(a) and 7(b) is in the pattern of closed loop. The warp knitted fabric 12 is composed of continuously and repeatedly disposed units each including one first loop row 1b and three second loop columns 2b. Thus, the warp knitted fabric 12 includes first loop columns 1b and second loop columns 2b in a proportion of 1:3.

Figure 8A:
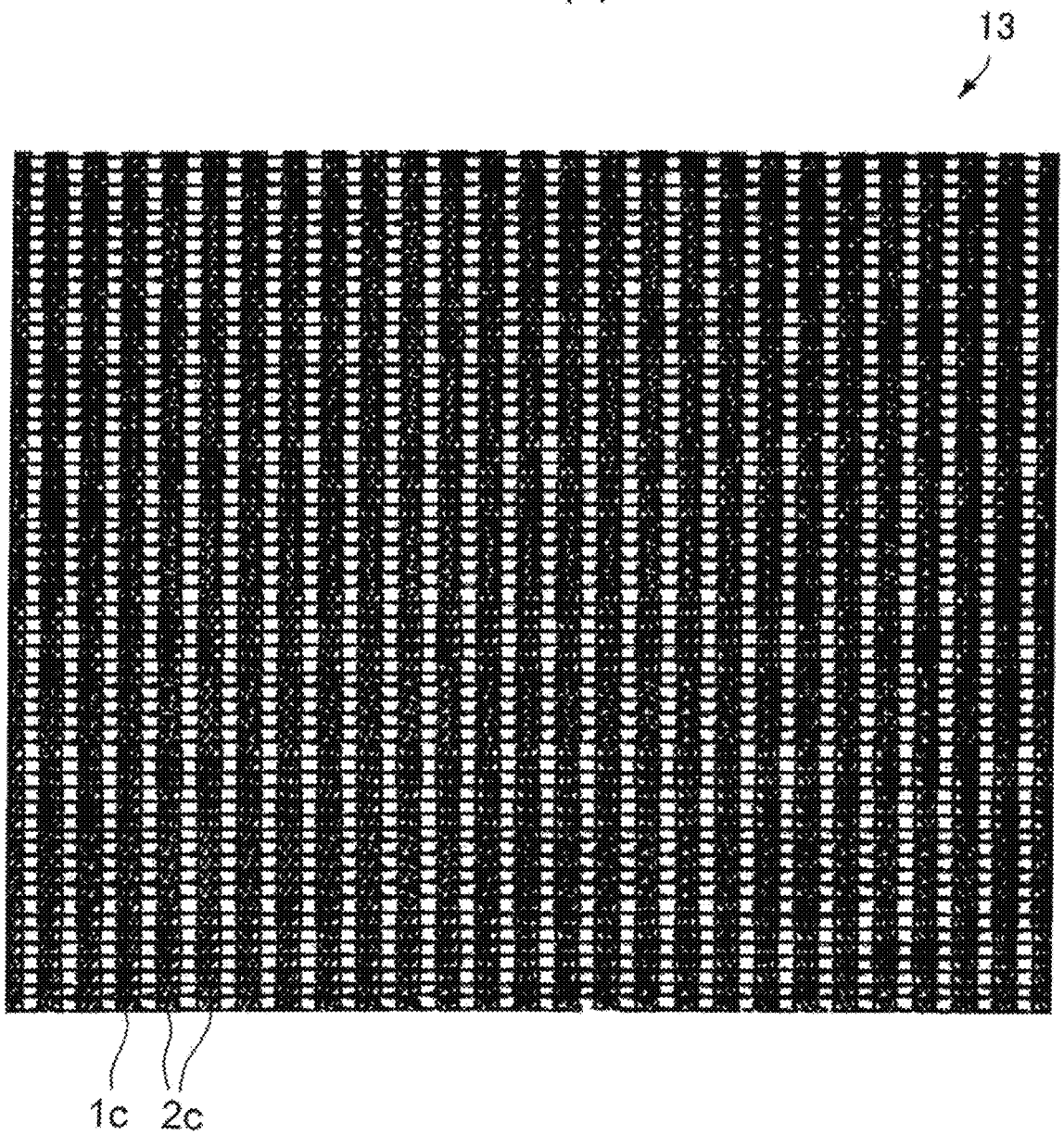
FIG. 8(a) is a front view of a warp knitted fabric according to a third embodiment.
Figure 8B:
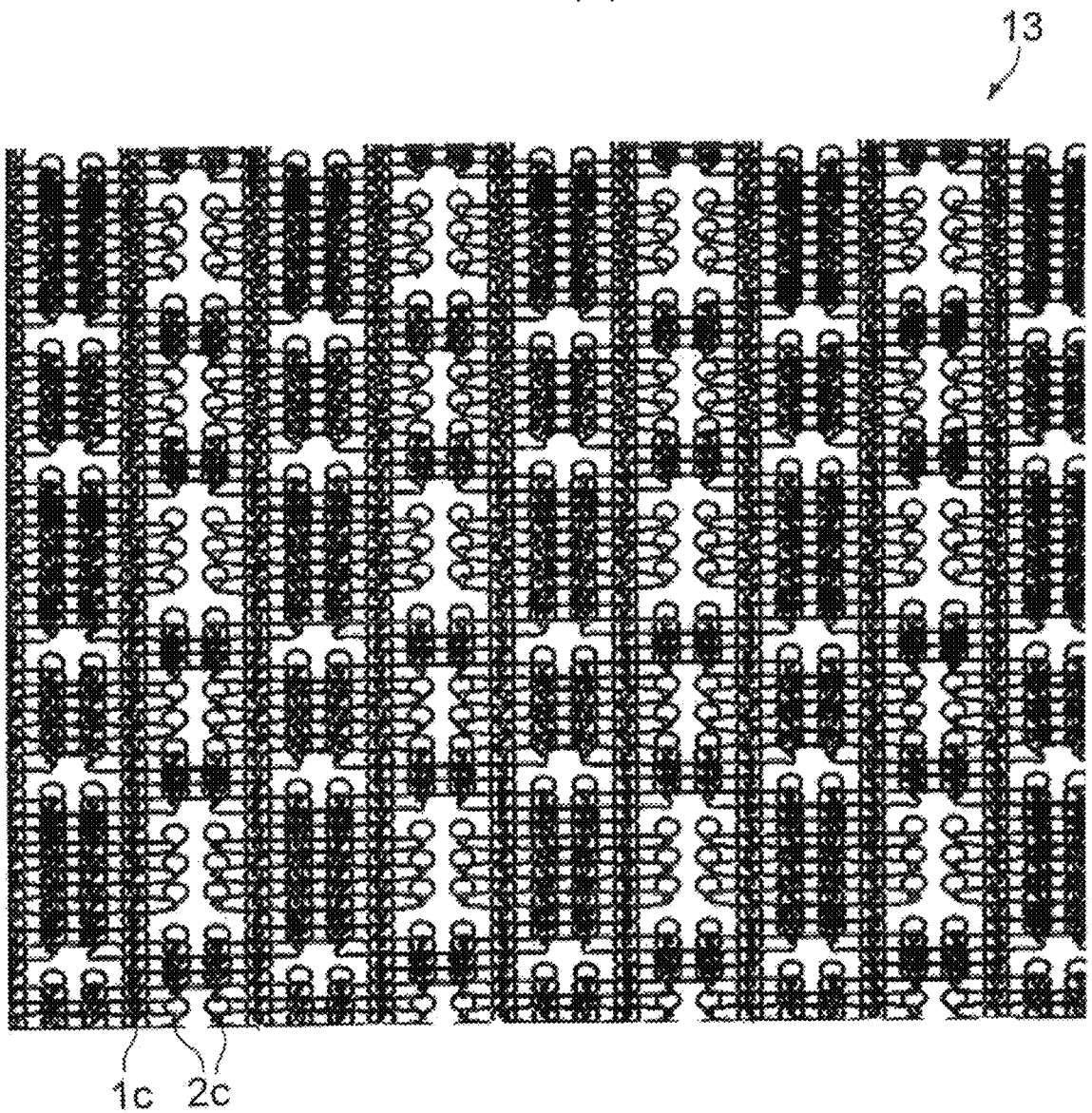
FIG. 8(b) is a front view of the state after decomposition and absorption of a yarn of a bioabsorbable material of the warp knitted fabric illustrated in FIG. 8(a).

FIG. 8(a) is a front view of a warp knitted fabric according to a third embodiment. FIG. 8(b) is a front view of the state after decomposition and absorption of a yarn of a bioabsorbable material of the warp knitted fabric illustrated in FIG. 8(a).

The warp knitted fabric 13 illustrated in FIGS. 8(a) and 8(b) is in the pattern of closed loop. The warp knitted fabric 13 is composed of continuously and repeatedly disposed units each including one first loop column 1c and two second loop columns 2c. Thus, the warp knitted fabric 13 includes first loop columns 1c and second loop columns 2c in a proportion of 1:2.

FIGS. 9(a) to 9(g) are respectively front views of the states of warp knitted fabrics according to fourth to tenth embodiments after decomposition and absorption of a yarn of a bioabsorbable material. Each of the warp knitted fabrics according to the fourth to tenth embodiments includes loop columns composed of a yarn of a bioabsorbable material and a yarn of a non-bioabsorbable material in a predetermined proportion. FIGS. 9(a) to 9(g) each illustrate the state after decomposition and absorption of the yarn of the bioabsorbable material.

Figure 9:
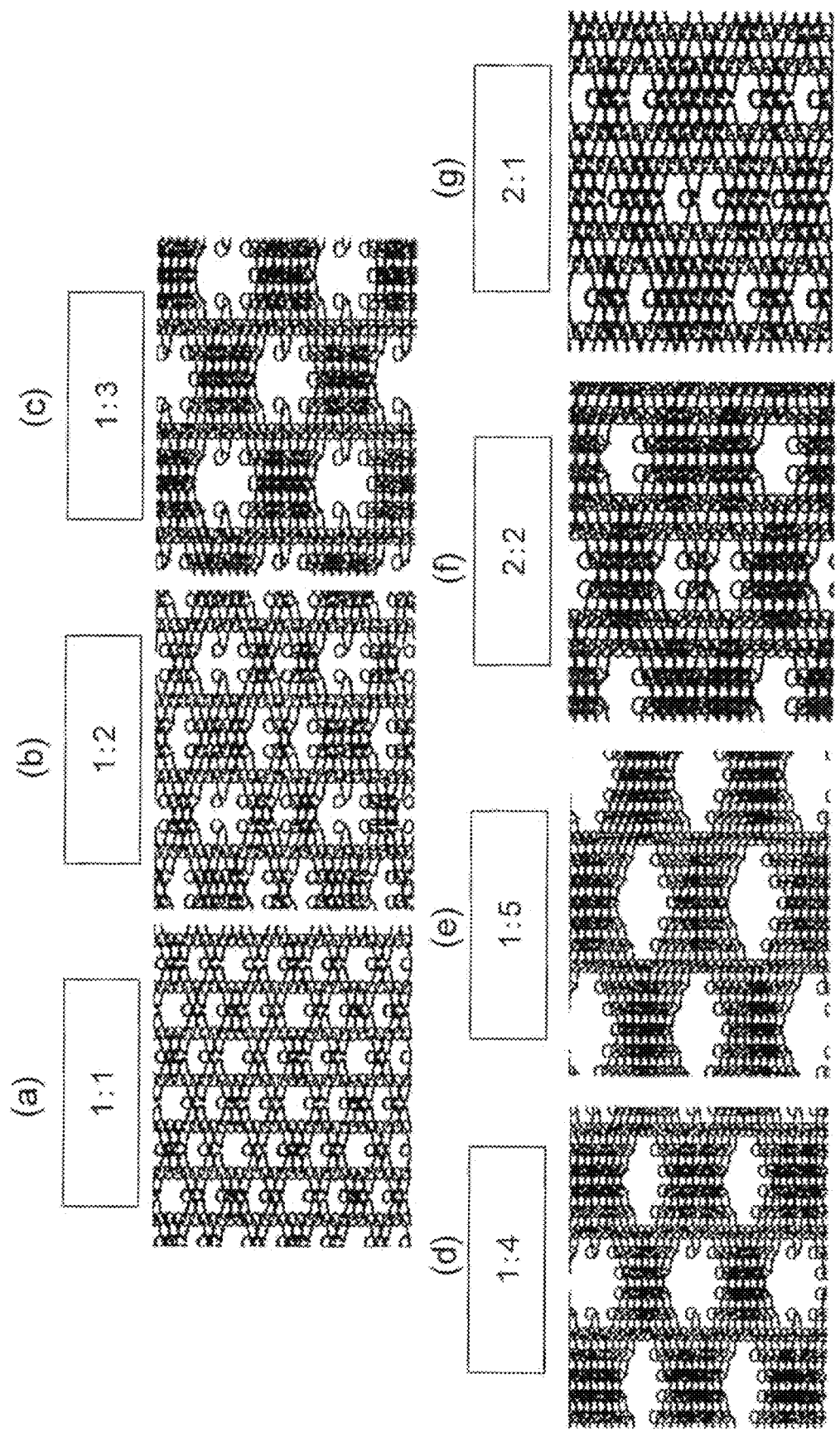
FIGS. 9(a) to 9(g) are respectively front views of the states of warp knitted fabrics according to fourth to tenth embodiments after decomposition and absorption of a yarn of a bioabsorbable material.

These warp knitted fabrics are prepared with a warp knitting machine having guide bars (GB1 to GB4) as illustrated in Table 1. As illustrated in FIG. 9, these fabrics, which have the same texture, include different patterns of first loop columns 1 and second loop columns 2 by varying the arrangement of loop columns.

TABLE 1

| GB1 | 10-12-23-34-45-56-67-78-76-65-54-43-32-21// |
|---|---|
| GB2 | 10-12-23-34-45-56-67-78-76-65-54-43-32-21// |
| GB3 | 78-76-65-54-43-32-21-10-12-23-34-45-56-67// |
| GB4 | 78-76-65-54-43-32-21-10-12-23-34-45-56-67// |

The warp knitted fabric according to the fourth embodiment is composed of continuously and repeatedly disposed units each including one first loop column and one second loop column (FIG. 9(a) illustrates the state after decomposition and absorption of the yarn of the bioabsorbable material). Thus, the warp knitted fabric of the fourth embodiment includes first loop columns and second loop columns in a proportion of 1:1.

The warp knitted fabric according to the fifth embodiment is composed of continuously and repeatedly disposed units each including one first loop column and two second loop columns (FIG. 9(b) illustrates the state after decomposition and absorption of the yarn composed of the bioabsorbable material). Thus, the warp knitted fabric of the fifth embodiment includes first loop columns and second loop columns in a proportion of 1:2.

The warp knitted fabric according to the sixth embodiment is composed of continuously and repeatedly disposed units each including one first loop column and three second loop columns (FIG. 9(c) illustrates the state after decomposition and absorption of the yarn of the bioabsorbable material). Thus, the warp knitted fabric of the sixth embodiment includes first loop columns and second loop columns in a proportion of 1:3.

The warp knitted fabric according to the seventh embodiment is composed of continuously and repeatedly disposed units each including one first loop column and four second loop columns (FIG. 9(d) illustrates the state after decomposition and absorption of the yarn composed of the bioabsorbable material). Thus, the warp knitted fabric of the seventh embodiment includes first loop columns and second loop columns in a proportion of 1:4.

The warp knitted fabric according to the eighth embodiment is composed of continuously and repeatedly disposed units each including one first loop column and five second loop columns (FIG. 9(e) illustrates the state after decomposition and absorption of the yarn composed of the bioabsorbable material). Thus, the warp knitted fabric of the eighth embodiment includes first loop columns and second loop columns in a proportion of 1:5.

The warp knitted fabric according to the ninth embodiment is composed of continuously and repeatedly disposed units each including two first loop columns and two second loop columns (FIG. 9(f) illustrates the state after decomposition and absorption of the yarn composed of the bioabsorbable material). Thus, the warp knitted fabric of the ninth embodiment includes first loop columns and second loop columns in a proportion of 1:1.

The warp knitted fabric according to the tenth embodiment is composed of continuously and repeatedly disposed units each including two first loop columns and one second loop column (FIG. 9(g) illustrates the state after decomposition and absorption of the yarn composed of the bioabsorbable material). Thus, the warp knitted fabric of the tenth embodiment includes first loop columns and second loop columns in a proportion of 2:1.

The warp knitted fabric may include first loop columns and second loop columns in any other proportion. For example, the warp knitted fabric may be composed of repeating units each including one first loop column and two or three second loop columns (i.e., a proportion of first loop columns and second loop columns of 1:2:1:3), repeating units each including one or two first loop columns and two second loop columns (i.e., a proportion of first loop columns and second loop columns of 2:2:1:2), or a combination of these repeating units.

The warp knitted fabric of the present invention includes first loop columns and second loop columns in a proportion of preferably 1:2 or 1:3, more preferably 1:2, from the viewpoint of the stability (i.e., strength) of the knitted fabric after expansion. As illustrated in FIG. 10(c), the expanded fabric exhibits high strength if yarns are evenly disposed in warp and weft directions.

Now will be described the physical properties, materials, and applications of the warp knitted fabric of the present invention.

The warp knitted fabric of the present invention (in the state where the bioabsorbable material is not decomposed or absorbed) preferably has a density of 60 to 120 courses/inch and 28 to 45 wales/inch. The density is more preferably 70 to 110 courses/inch and 30 to 42 wales/inch, still more preferably 80 to 100 courses/inch and 32 to 40 wales/inch, from the viewpoints of ease of application of the fabric to a sutured biological tissue, and the water resistance, needle hole leakage, and anisotropy of the warp knitted fabric.

The warp knitted fabric after elimination of the yarn composed of the bioabsorbable material preferably exhibits an expansion 1.2 to 8.0 times, more preferably 2.0 to 8.0 times that before elimination of the yarn composed of the bioabsorbable material.

If the warp knitted fabric is used as a filling material for a surgically sutured portion in a tissue of a pediatric patient (whose organs grow rapidly) or a restorative for a surgical detect in the tissue, the warp knitted fabric can follow the growth of the tissue.

The bioabsorbable material for use in the warp knitted fabric of the present invention may be of any type that has biocompatibility and is eliminated through decomposition and absorption in a living organism over time.

Examples of the bioabsorbable material include poly(glycolic acid), poly(lactic acid), lactide-glycolide copolymers, poly(malic acid), polydioxanone, polycaprolactone, polyhydroxyalkanoate, modified poly(vinyl alcohol), casein, modified starch, glactin-caprolactone copolymers, glycolic acid-lactic acid copolymers, and derivatives thereof.

Among these materials, preferred is at least one selected from poly(lactic acid), polydioxanone, poly(glycolic acid), glactin-caprolactone copolymers, and glycolic acid-lactic acid copolymers. The use of such a material contributes to improvements in versatility and strength of the warp knitted fabric, and facilitates the decomposition and absorption of the fabric in a living organism.

Any known technique may be used for controlling the bioabsorption rate of the yarn composed of the bioabsorbable material. For example, the bioabsorption rate can be controlled by modification of the proportion of copolymer components, or hydrophilization or hydrophobization of side chains of a polymer. Among the aforementioned bioabsorbable materials, poly(lactic acid), poly(glycolic acid), and polycaprolactone are known to satisfy the following relation in terms of bioabsorption rate: poly(glycolic acid)>poly(lactic acid)>polycaprolactone (i.e., poly(glycolic acid) has the highest bioabsorbability). Thus, the bioabsorption rate of a lactide-glycolide copolymer can be controlled by adjustment of the proportion of a lactide component and a glycolide component.

If the warp knitted fabric of the first embodiment is applied to a tissue of a human, the warp knitted fabric is gradually decomposed a predetermined period after fixation of the fabric to the tissue in accordance with the degree of growth of the human body. In general, a period of three months to three years is required for elimination of the yarn composed of the bioabsorbable material in the warp knitted fabric through decomposition and absorption of the yarn in a living organism. In the warp knitted fabric of the present invention, the bioabsorption rate of the first yarn is preferably lower than that of the second yarn. The first yarn is preferably decomposed six months to several years after decomposition of the second yarn for reliable expansion of the warp knitted fabric.

The non-bioabsorbable material for use in the warp knitted fabric of the present invention may be of any type that has biocompatibility and is not decomposed or absorbed in a living organism over time.

Examples of the non-bioabsorbable material include fluorine fibers, nylon fibers, polyester fibers, acrylic fibers, vinylon fibers, vinylidene fibers, poly(vinyl chloride) fibers, polyethylene fibers, polypropylene fibers, polyurethane fibers, carbon fibers, polystyrene fibers, and poly(methyl methacrylate). Examples of the polyester include poly(ethylene terephthalate), poly(trimethylene terephthalate), poly(butylene terephthalate), poly(lactic acid), stereocomplex poly(lactic acid), and polyesters copolymerized with a third component.

Among these materials, preferred is at least one selected from fluorine fibers, nylon fibers, polyester fibers, and polypropylene fibers. The use of such a material contributes to improvements in versatility and strength of the warp knitted fabric, and maintenance of sufficient strength of the fabric.

The yarn composed of the non-bioabsorbable material for use in the warp knitted fabric of the present invention preferably has a total fineness of 22 to 110 dtex, a single fiber fineness of 0.8 to 5.0 dtex, and 1 to 48 filaments. The yarn composed of the non-bioabsorbable material with, for example, a fineness within the above range has a lightweight and maintains a sufficient strength. More preferably, the yarn composed of the non-bioabsorbable material has a total fineness of 25 to 50 dtex, a single fiber fineness of 1 to 5 dtex, and 5 to 20 filaments.

The yarn composed of the bioabsorbable material for use in the warp knitted fabric of the present invention preferably has a total fineness of 20 to 200 dtex, a single fiber fineness of 1.3 to 44 dtex, and 1 to 24 filaments. The yarn composed of the bioabsorbable material having a fineness within the above range can be decomposed and absorbed in a living organism. More preferably, the yarn composed of the bioabsorbable material has a total fineness of 25 to 50 dtex, a single fiber fineness of 1 to 5 dtex, and 5 to 20 filaments.

The yarn composed of the bioabsorbable material and/or the yarn composed of the non-bioabsorbable material may be a monofilament or multifilament yarn. The use of a multifilament yarn can provide the warp knitted fabric with a soft texture. The use of a multifilament yarn in a living organism is preferred in terms of tissue regeneration because cellular tissues are allowed to infiltrate to monofilaments. A monofilament yarn is washed more efficiently than a multifilament yarn. The multifilament yarn composed of the bioabsorbable material and/or the multifilament yarn composed of the non-bioabsorbable material preferably has 5 to 20 filaments and a total fineness of 25 to 50 dtex.

The warp knitted fabric of the present invention is prepared with a tricot knitting machine in a common zigzag pattern, such as atlas stitch, such that first loop columns (or second loop columns) are linked together and first loop columns are linked with second loop columns. The final form of the warp knitted fabric can be varied to have a desired texture through modification of the type of the yarn or the arrangement and proportion of loop columns. All guide bars can be disposed in a proportion of 1:1, 4:2, or 5:3 for modification of the proportion of loops composed of the yarn composed of the non-bioabsorbable material in second loop columns. A knitting machine having two beams and two bars, or three beams and two bars, may be used for simultaneous knitting of yarns having the same elongation, hardness, and fineness.

The warp knitted fabric of the present invention is used as, for example, a restorative, a filling material, or a reinforcement for the damage, defect, or stenosis of a living body-tissue. Examples of the tissue include blood vessel, cardiac valve, pericardium, dura mater, cartilage, skin, mucosa, ligament, tendon, muscle, trachea, and peritoneum, or the like. Examples of the damage of the living body include surgery, trauma, and congenital defect and stenosis. The warp knitted fabric can be used in the cardiac surgery for, for example, atrial septal defect, ventricular septal defect, atrioventricular septal defect, tetralogy of Fallot, pulmonary artery stenosis, or single ventricles, or the like.

In particular, the warp knitted fabric of the present invention is suitable for use as a cardiac repair patch, i.e., a restorative for a defected or stenotic portion of an infant heart. In such a case, the warp knitted fabric strongly supports a repaired portion at an early stage and significantly expands at the stage of elimination of the yarn composed of the bioabsorbable material. Thus, the warp knitted fabric can follow an increase in size of the repaired organ in association with the growth of the human body.

[Medical Material]

The medical material of the present invention will now be described.

The "coating" of the medical material of the present invention refers to the state where a hydrogel is deposited on the surfaces of yarns of the warp knitted fabric and between yarns of the fabric such that a fluid, such as blood, does not permeate the fabric. As used herein, the term "coating" may be referred to as "sealing."

The expression "space is filled with a hydrogel" in the medical material of the present invention refers to the state where the hydrogel is fixed between yarns of the warp knitted fabric such that a fluid does not permeate the fabric.

In the medical material of the present invention, at least one of both surfaces of the warp knitted fabric is coated with a hydrogel. Thus, the medical material can reduce or prevent leakage of a fluid, such as blood, through the warp knitted fabric. The medical material involves successful replacement of the hydrogel with tissue in a living organism, and the tissue replacement results in regeneration of smooth muscle and small vessels. The medical material also reduces calcification by calcium deposition which may be caused by dead cells. More preferably, both surfaces of the warp knitted fabric are coated with a hydrogel.

As used herein, a medical material comprising a warp knitted fabric coated with a hydrogel may be referred to as "sealed warp knitted fabric," and a medical material comprising a fabric coated with a hydrogel may be referred to as "sealed fabric."

The hydrogel is preferably a biocompatible polymer into which water can be incorporated. Examples of the hydrogel include proteins, such as collagen, gelatin (i.e., a hydrolysate of collagen), proteoglycan, fibronectin, vitronectin, laminin, entactin, tenascin, thrombospondin, von Willebrand factor, osteopontin, and fibrinogen; polysaccharides, such as glycosaminoglycan (e.g., chondroitin sulfate), starch, glycogen, agarose, and pectin; and water-soluble, hydrophilic, and water-absorbable synthetic polymers, such as poly(lactic acid), poly(glycolic acid), poly(γ-glutamic acid), and copolymers thereof. These materials may be used in combination. In particular, the hydrogel is preferably gelatin and/or collagen from the viewpoint of versatility and biocompatibility.

The sealed warp knitted fabric of the present invention is readily handled; i.e., the fabric is easily sutured during surgery. In detail, the sealed warp knitted fabric of the present invention undergoes no or little deformation during implantation, has appropriate flexibility, and comes into close contact with a tissue. In addition, the sealing layer is not removed from the fabric. The sealed warp knitted fabric of the present invention exhibits appropriate anisotropy, i.e., an appropriate difference between the MD elastic modulus and TD elastic modulus. An excessively large anisotropy may generate an undesired force that inhibits the expansion in a certain direction of the warp knitted fabric in a living organism. The sealed warp knitted fabric of the present invention has high water resistance. A needle hole formed by a suture needle during suture of the sealed warp knitted fabric to a tissue is closed to prevent leakage of a fluid (e.g., blood) through the fabric.

[Sealing Process]

The process of sealing a fabric of the present invention will now be described.

The sealing process may involve immersion of the fabric in a hydrogel, or spraying or application of a hydrogel to the fabric. For example, the fabric may be immersed in a solution containing a hydrogel and then cooled or dried at a predetermined temperature, to coat the fabric with the hydrogel. The process temperature is preferably about 0° C. to about 40° C., more preferably about 0° C. to about 30° C. The process period is about 30 minutes to two hours.

The sealing process of the present invention may involve cross-linking of a hydrogel. The process may involve the use of any cross-linking agent common in the art, such as glutaraldehyde or glyoxal. The concentration of the cross-linking agent is generally about 0.1 to about 10 wt %.

The fabric may be a knitted fabric, such a tricot knitted fabric or a double-raschel knitted fabric, or a woven fabric, such as a plain-woven fabric or a twill-woven fabric. The knitted fabric may be a warp or weft knitted fabric.

If the hydrogel is a protein, the amount of the hydrogel for coating of a fabric (solid content (mass) per unit area) is generally 1 to 30 mg/cm$^2$, preferably 1 to 20 mg/cm$^2$, more preferably 1 to 10 mg/cm$^2$, particularly preferably 1.4 to 6.0 mg/cm$^2$. The weight of a fabric per unit area is generally 40 to 100 g/m$^2$, preferably 50 to 80 g/m$^2$, more preferably 50 to 80 g/m$^2$. The swelling (%) of the hydrogel determined by Formula (I) described below is generally 400 to 1,200%, preferably 400 to 1,100%, more preferably 414 to 1,028%.

The high water resistance, reduced needle hole leakage, and improved handleability during surgery of the sealed fabric of the present invention can be achieved by adjustment of the fabric areal weight, the amount of the hydrogel coating, and the swelling (%) of the hydrogel. The sealed fabric of the present invention preferably satisfies the following relations:

$$50 \leq X \leq 75, 1.4 \leq Y \leq 6.0, \text{ and } 414 \leq Z \leq 1,028 \quad [F2]$$

where X represents the fabric areal weight (g/m$^2$), Y represents the amount of the hydrogel coating (mg/cm$^2$), and Z represents the swelling (%) of the hydrogel.

An amount of the hydrogel coating of less than 1.4 mg/cm$^2$ leads to insufficient water resistance, whereas an amount of the hydrogel coating of more than 6.0 mg/cm$^2$ may result in deformation of the sealed fabric. A swelling of the hydrogel of less than 414% leads to insufficient adhesion between the sealed fabric and a target to which the fabric is applied, e.g., a specific biological tissue), whereas a swelling of the hydrogel of more than 1,028% may result in removal of the sealing layer from the fabric.

More preferably, in the sealed fabric of the present invention, the values X, Y, and Z (which are as defined above) in an orthogonal coordinate system (X, Y, Z) are present on edges and in the inner space of a polyhedron having the following vertices: point A (50, 6, 700), point B (50, 6, 800), point C (50, 4, 800), point D (50, 4, 700), point E (70, 6.2, 459), point F (70, 6.2, 965), point G (70, 1.6, 965), point H (70, 1.6, 459), point I (72, 4.9, 826), point J (72, 4.9, 1028), point K (72, 1.7, 1028), and point L (72, 1.7, 826).

Still more preferably, in the sealed fabric of the present invention, the values X, Y, and Z in an orthogonal coordinate system (X, Y, Z) are present on edges and in the inner space of a polyhedron having the following vertices: point A (54, 5.3, 760), point B (70, 6.2, 459), point C (70, 4.4, 965), point D (70, 1.6, 552), point E (72, 1.7, 1028), point F (72, 3.6, 877), and point G (72, 4.9, 826).

The sealed fabric of the present invention can be used as a medical material, such as a restorative or a reinforcement for the damage of a biological tissue. Examples of the medical material include cardiovascular repair patches, stents, balloon catheters, stent grafts, vascular prostheses, cardiac valve prostheses, and annular prostheses. The use of the sealed fabric of the present invention as a medical material leads to successful replacement of the hydrogel with living tissue in a living organism, and the tissue replacement induces regeneration of collagen fiber, smooth muscle, and small vessels. In addition, the sealed fabric also reduces calcification caused by calcium deposition.

The sealed fabric of the present invention exhibits high water resistance, improved handleability, and reduced needle hole leakage as in the aforementioned sealed warp knitted fabric.

EXAMPLES

The present invention will now be described by way of examples, which should not be construed to limit the invention.

<Examples of Warp Knitted Fabric>
[Preparation of Warp Knitted Fabric]

For preparation of a warp knitted fabric, a yarn of poly(lactic acid) (33T12, manufactured by TEIJIN LIMITED) as a yarn of a bioabsorbable material and a yarn of poly(ethylene terephthalate) (33T12, type 262, manufactured by Toray Industries, Inc.) as a yarn of a non-bioabsorbable material, were wound around a beam of a warping machine. The number of yarns was determined in accordance with the width of a warp knitted fabric. The wound yarns were then applied to a knitting machine (tricot knitting machine, 32 gauges, 120 courses) and placed in guide bars (reeds) through a separator having a thread guide.

Four guide bars (GB1 to GB4) were used in the knitting machine, and the yarns were formed into a plain knitted fabric. The yarns were arranged in two guide bars (GB1 and GB2) to achieve a full set and in the remaining two guide bars (GB3 and GB4) to achieve a full set. The resultant knitted fabric was thermally set at 120° C. for one hour to have a density of 36 wales/inch and 117 courses/inch.

Figure 10:
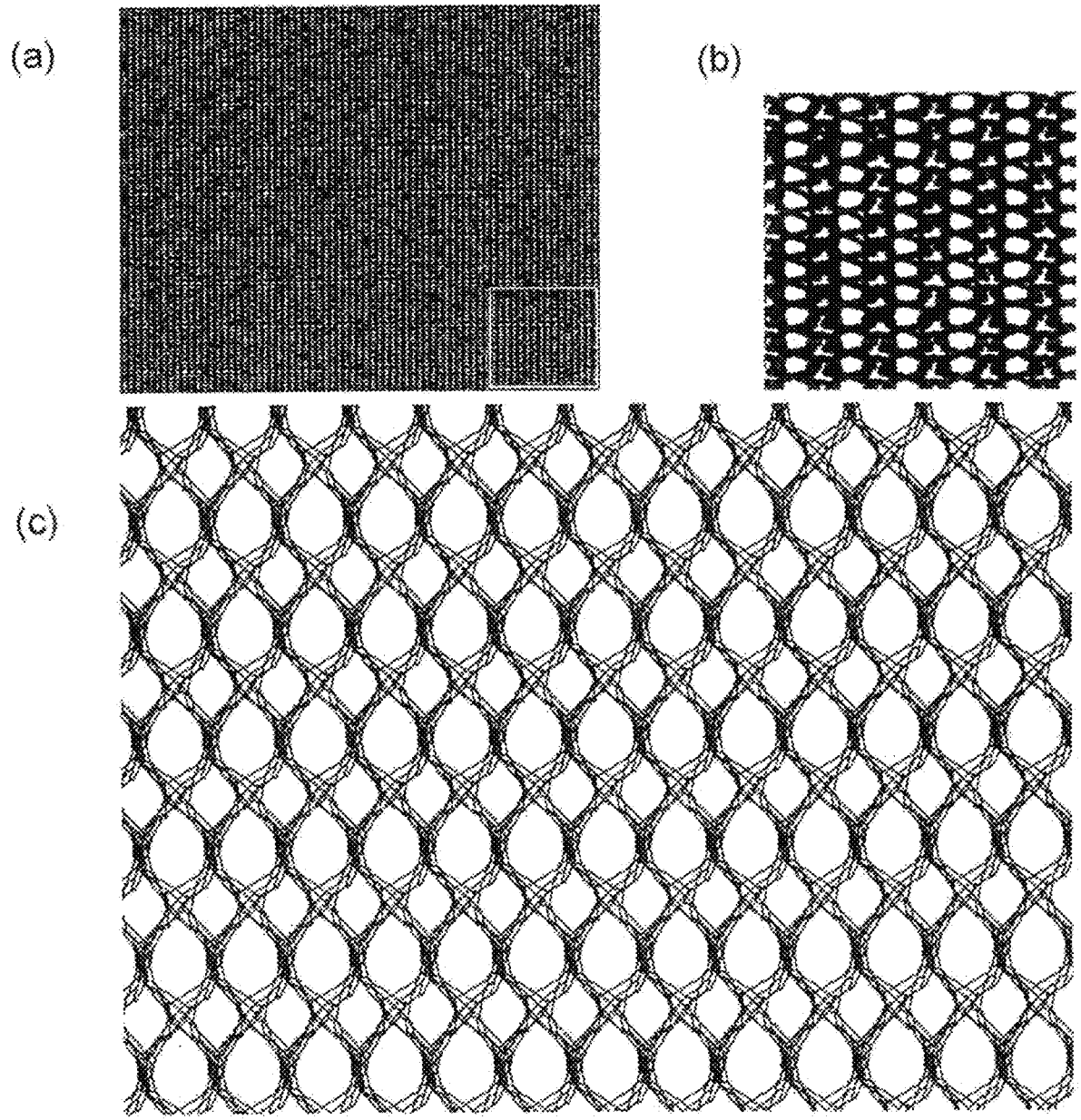
FIG. 10(a) illustrates a warp knitted fabric prepared in Example 1.
FIG. 10(b) is an enlarged view of the warp knitted fabric.
FIG. 10(c) illustrates the state of expansion of the warp knitted fabric prepared in Example 1 after decomposition and absorption of a yarn of a bioabsorbable material.

Table 2 illustrates the patterns and textures of prepared warp knitted fabrics (FIGS. 10 to 18), and Table 3 illustrates textures thereof. The yarn of polyethylene terephthalate) was placed in GB1 and GB3, and the yarn of polylactic acid) was placed in GB2 and GB4.

yarn composed of the bioabsorbable material was eliminated. FIGS. 10 to 18 illustrate warp knitted fabrics after elimination of the bioabsorbable material. FIG. 10(a) illustrates a warp knitted fabric, FIG. 10(b) is a partial enlarged view of the fabric, and FIG. 10(c) illustrates the state of expansion of the fabric in warp and weft directions after elimination of the yarn composed of the bioabsorbable material. FIGS. 11 to 18 each illustrate the state of expansion of a warp knitted fabric in warp and weft directions after elimination of the yarn composed of the bioabsorbable material.

<Comparative Example of Warp Knitted Fabric>

Comparative Example 1

A warp knitted fabric was prepared as in Example 1 except that the texture and the arrangement were modified as follows.

TABLE 4

Figure 19:
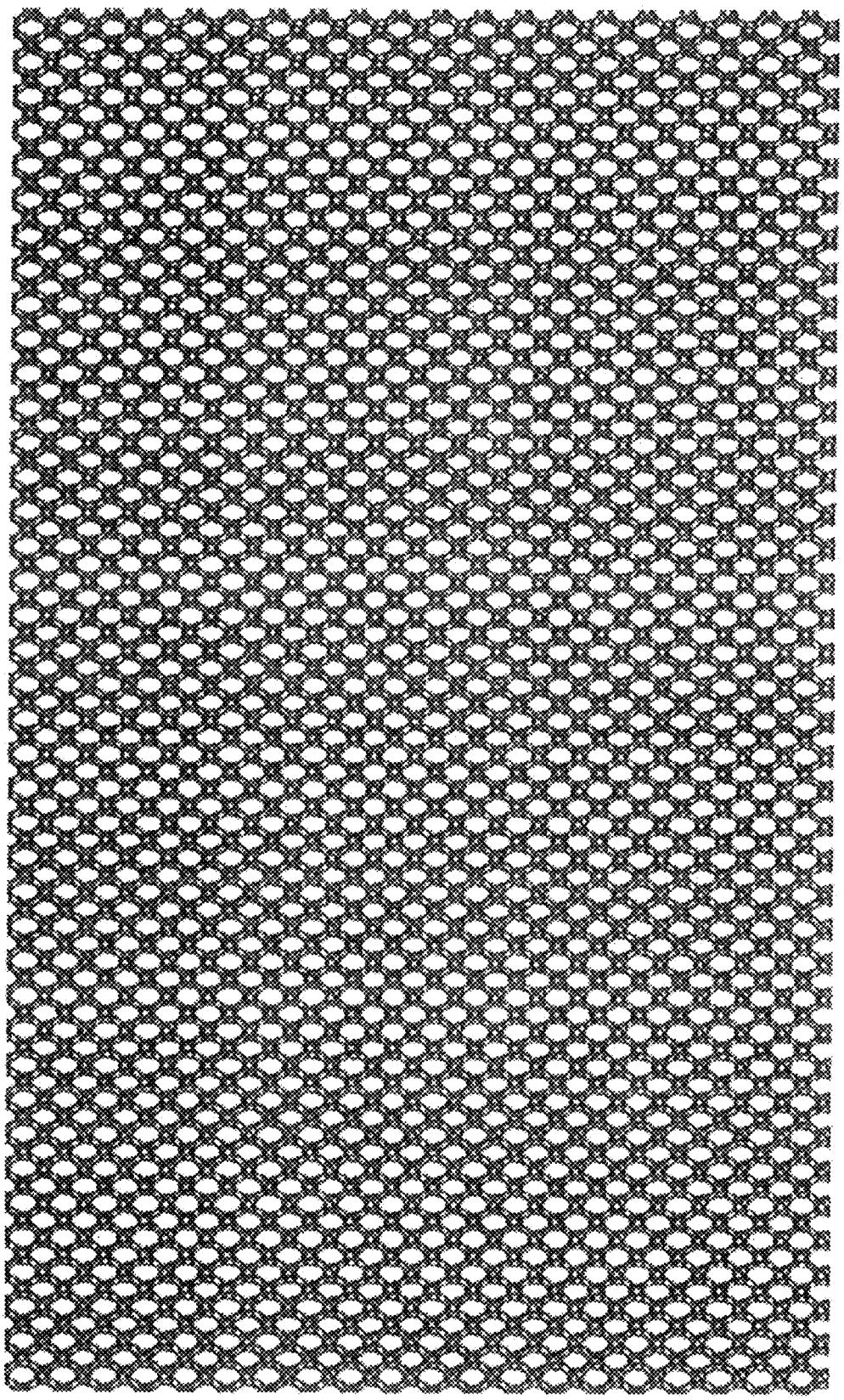
FIG. 19 illustrates the state of expansion of a warp knitted fabric prepared in Comparative Example 1 after decomposition and absorption of a yarn of a bioabsorbable material.
Figure 20A:
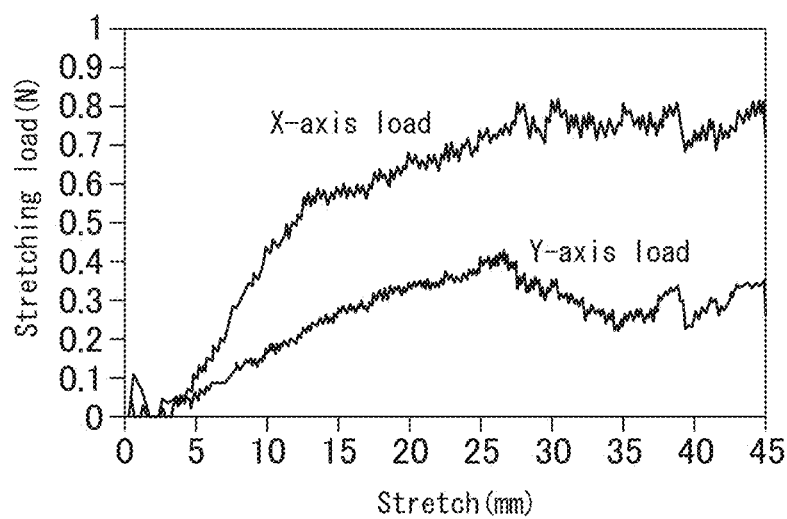
FIG. 20(a) is a graph illustrating the results of biaxial stretching of a warp knitted fabric (120 courses) prepared in Example 1 and warp knitted fabrics prepared with different courses (60 and 90 courses) (Examples 10 to 12).
Figure 20B:
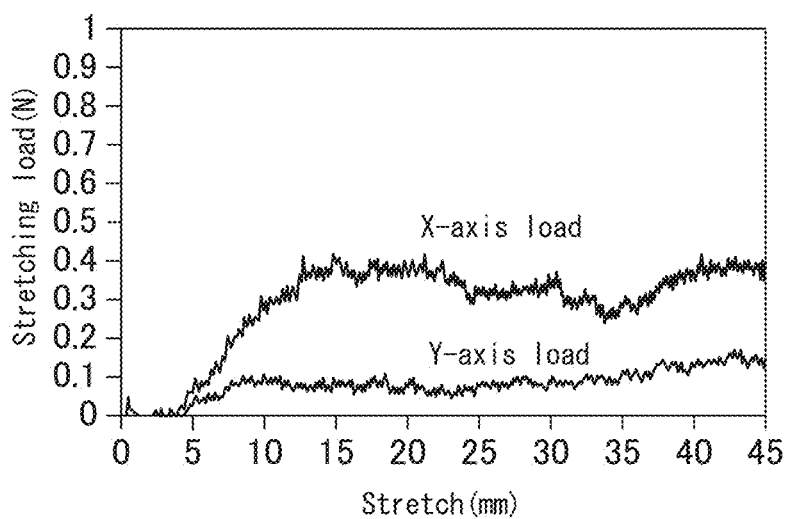
FIG. 20(b) is a graph illustrating the results of biaxial stretching of a warp knitted fabric (120 courses) prepared in Example 1 and warp knitted fabrics prepared with different courses (60 and 90 courses) (Examples 10 to 12).
Figure 20C:
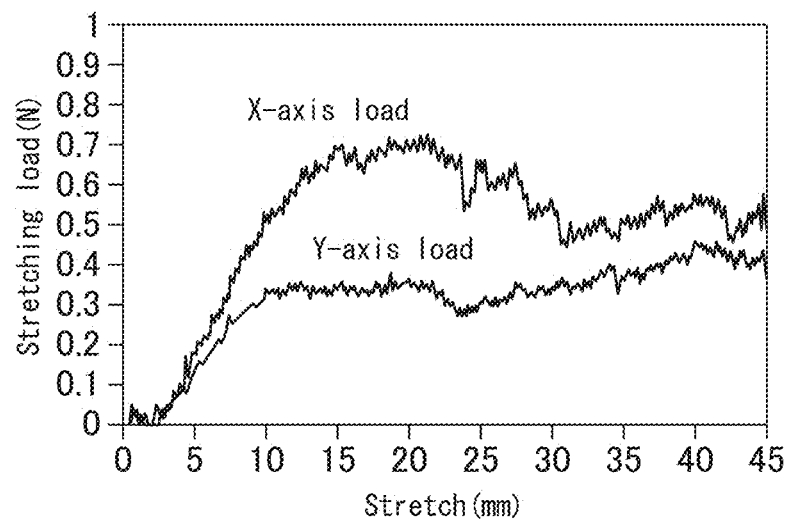
FIG. 20(c) is a graph illustrating the results of biaxial stretching of a warp knitted fabric (120 courses) prepared in Example 1 and warp knitted fabrics prepared with different courses (60 and 90 courses) (Examples 10 to 12).
Figure 20D:
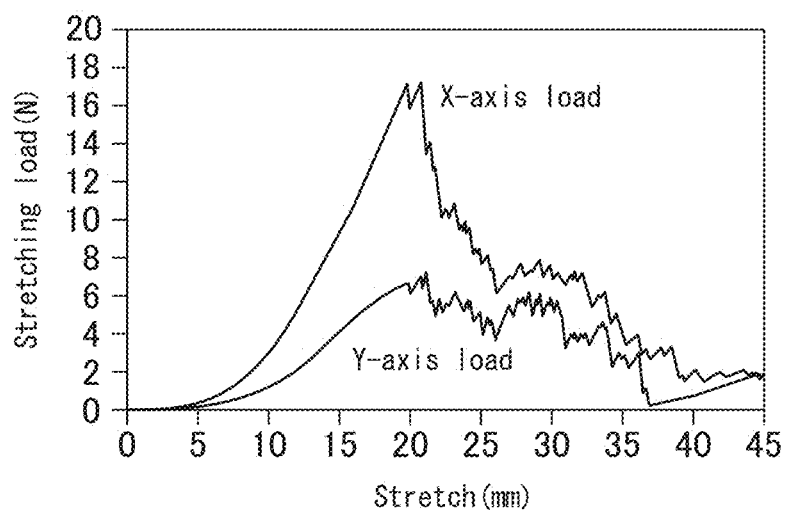
FIG. 20(d) is a graph illustrating the results of biaxial stretching of a warp knitted fabric prepared in Comparative Example 1 (Comparative Example 2).

| | Figure number | | Texture | Arrangement |
|---|---|---|---|---|
| Comparative Example 1 | FIG. 19 | GB1 | 10-12-23-21// | 1in, 1out |
| | | GB2 | 23-21-10-12// | |
| | | GB3 | 10-01// | |
| | | GB4 | 00-33// | |

[Biaxial Stretching of Warp Knitted Fabric After Decomposition of Poly(lactic Acid)]

Example 10

The warp knitted fabric prepared in Example 1 was cut into dimensions of 100 mm by 100 mm, and then immersed in 1M aqueous NaOH solution at 60° C. for two hours to decompose the PLA yarn in the warp knitted fabric. The resultant piece was washed with ultrapure water and dried to prepare a test sample. The test sample was then cut into dimensions of 60 mm by 60 mm and subjected to a constant-

TABLE 2

Figure 11:
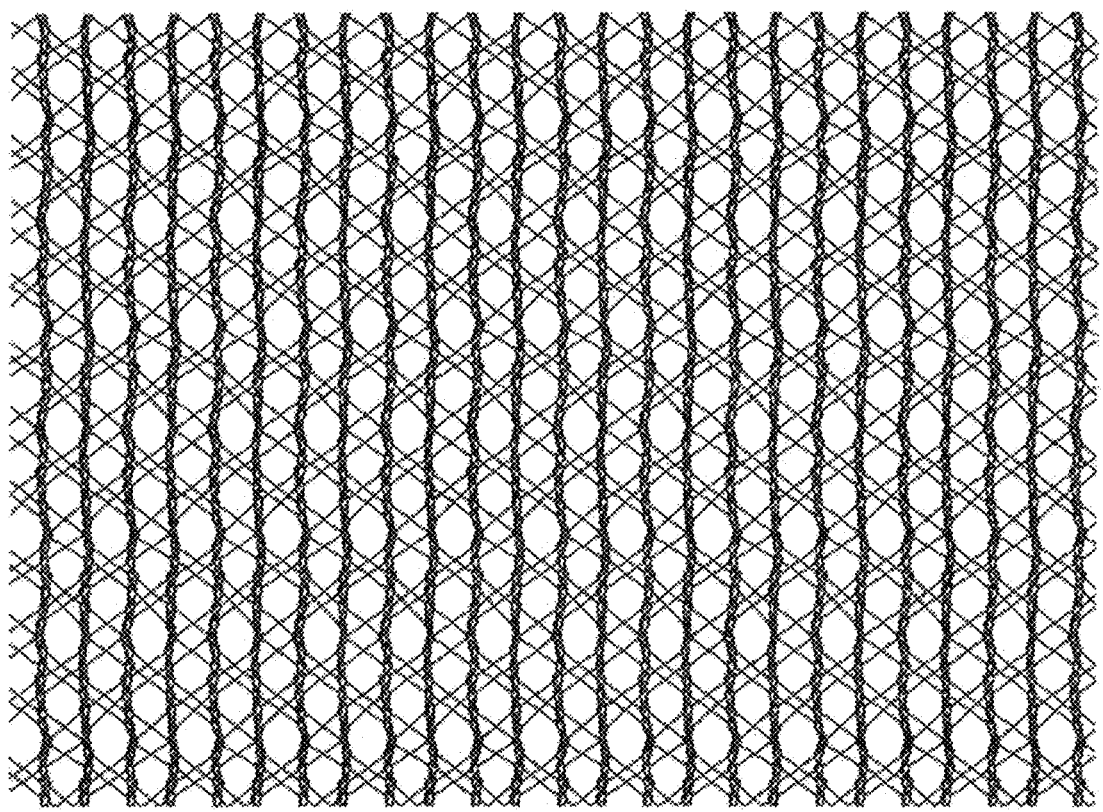
FIG. 11 illustrates the state of expansion of a warp knitted fabric prepared in Example 2 after decomposition and absorption of a yarn of a bioabsorbable material.
Figure 12:
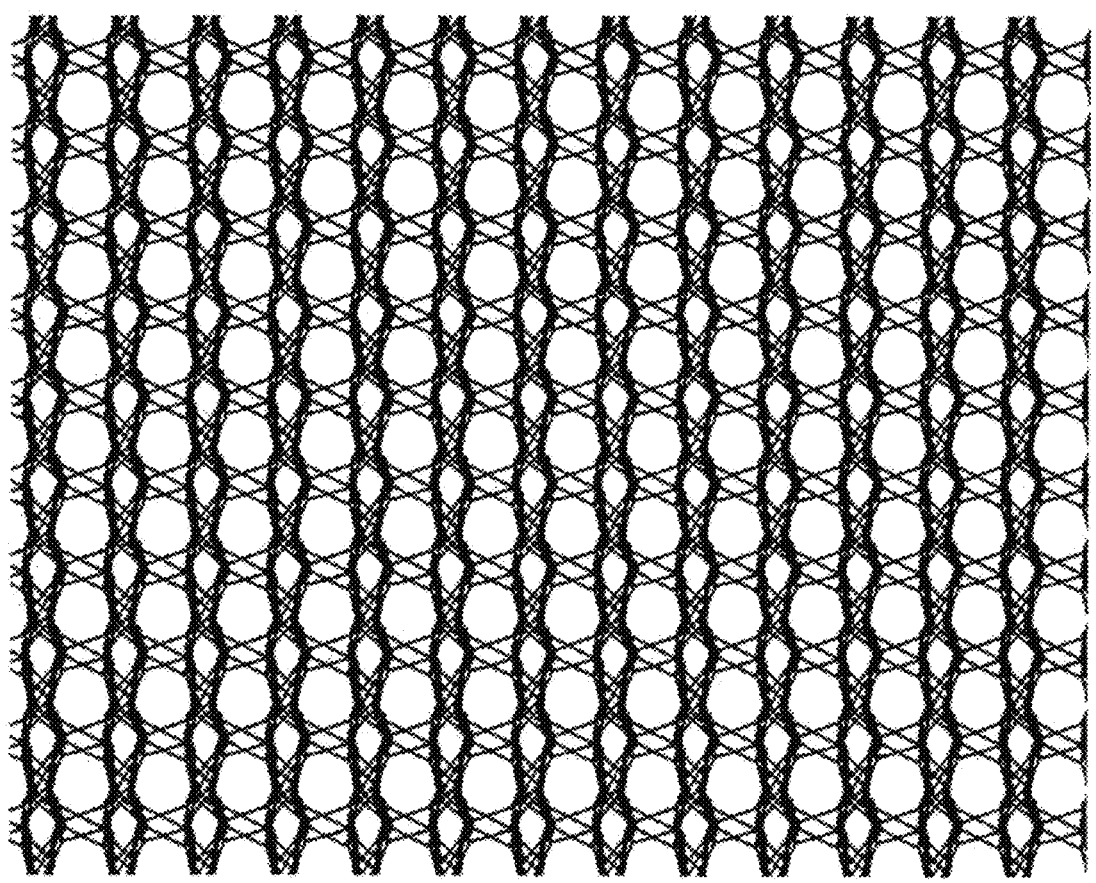
FIG. 12 illustrates the state of expansion of a warp knitted fabric prepared in Example 3 after decomposition and absorption of a yarn of a bioabsorbable material.
Figure 13:
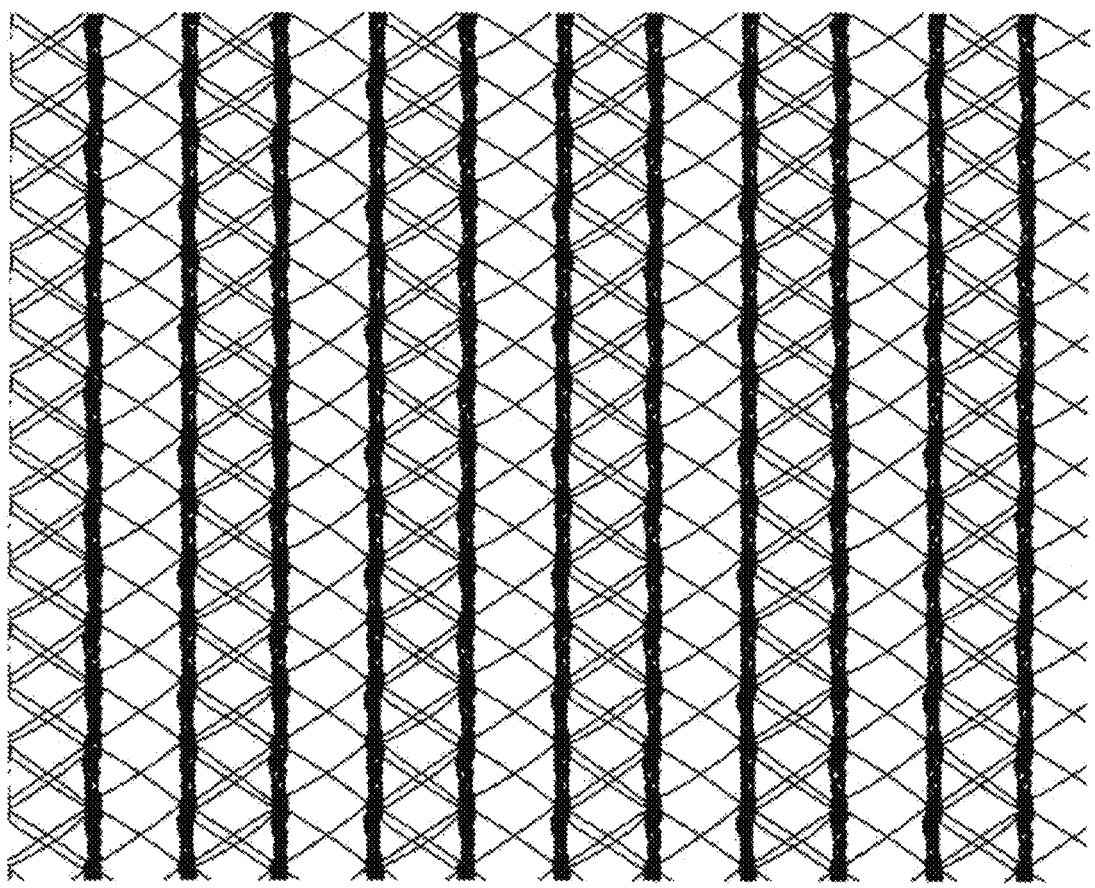
FIG. 13 illustrates the state of expansion of a warp knitted fabric prepared in Example 4 after decomposition and absorption of a yarn of a bioabsorbable material.
Figure 14:
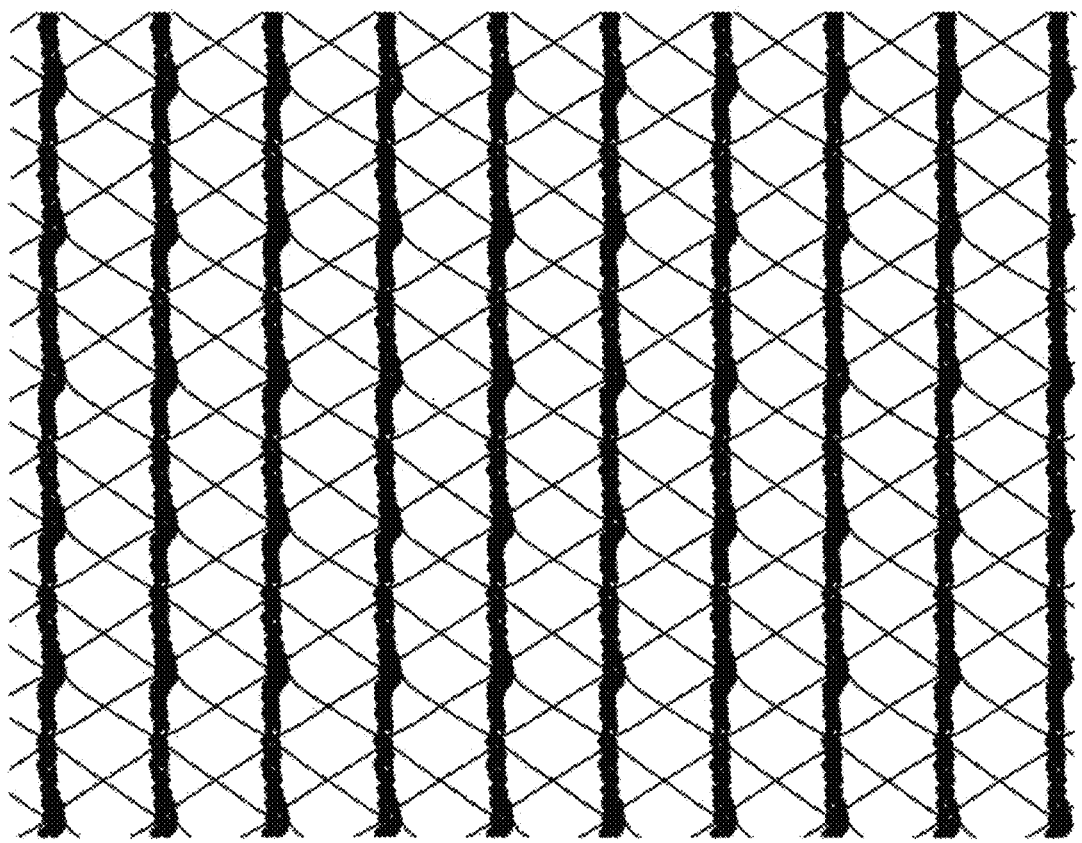
FIG. 14 illustrates the state of expansion of a warp knitted fabric prepared in Example 5 after decomposition and absorption of a yarn of a bioabsorbable material.
Figure 15:
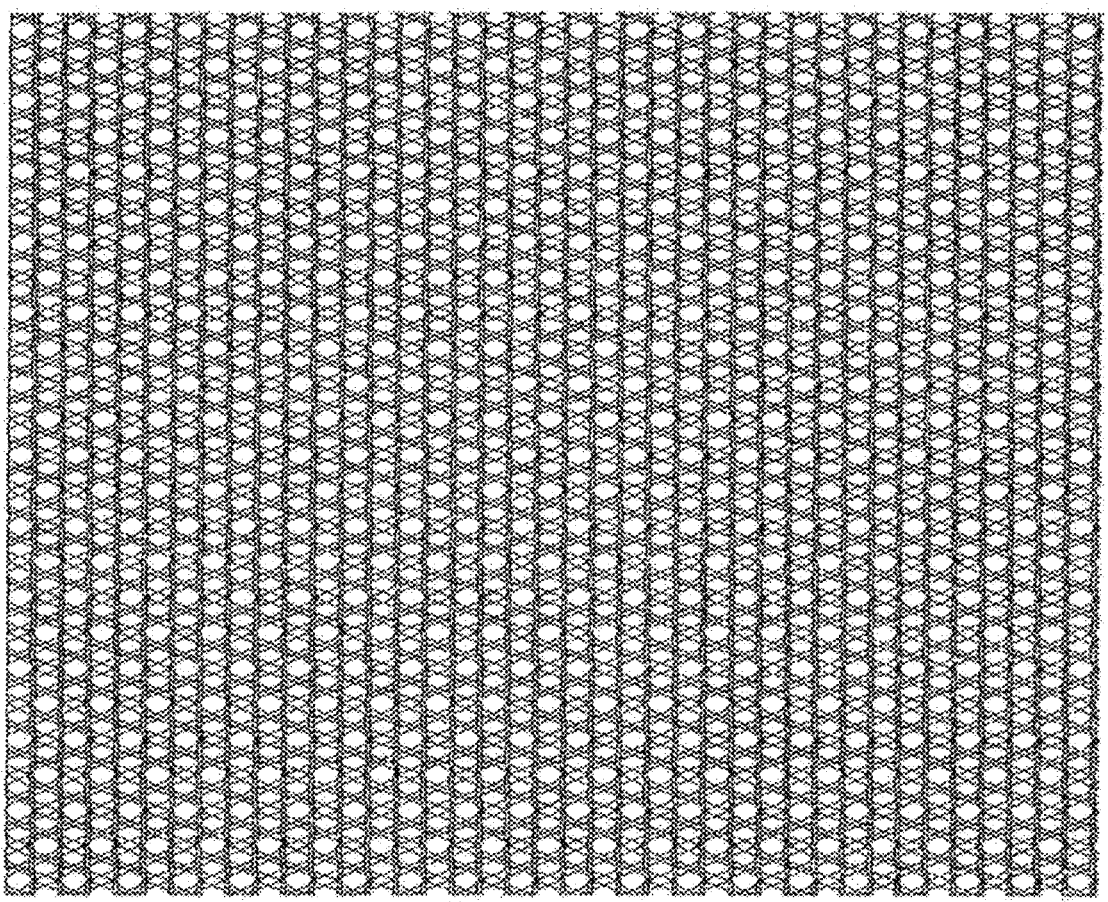
FIG. 15 illustrates the state of expansion of a warp knitted fabric prepared in Example 6 after decomposition and absorption of a yarn of a bioabsorbable material.
Figure 16:
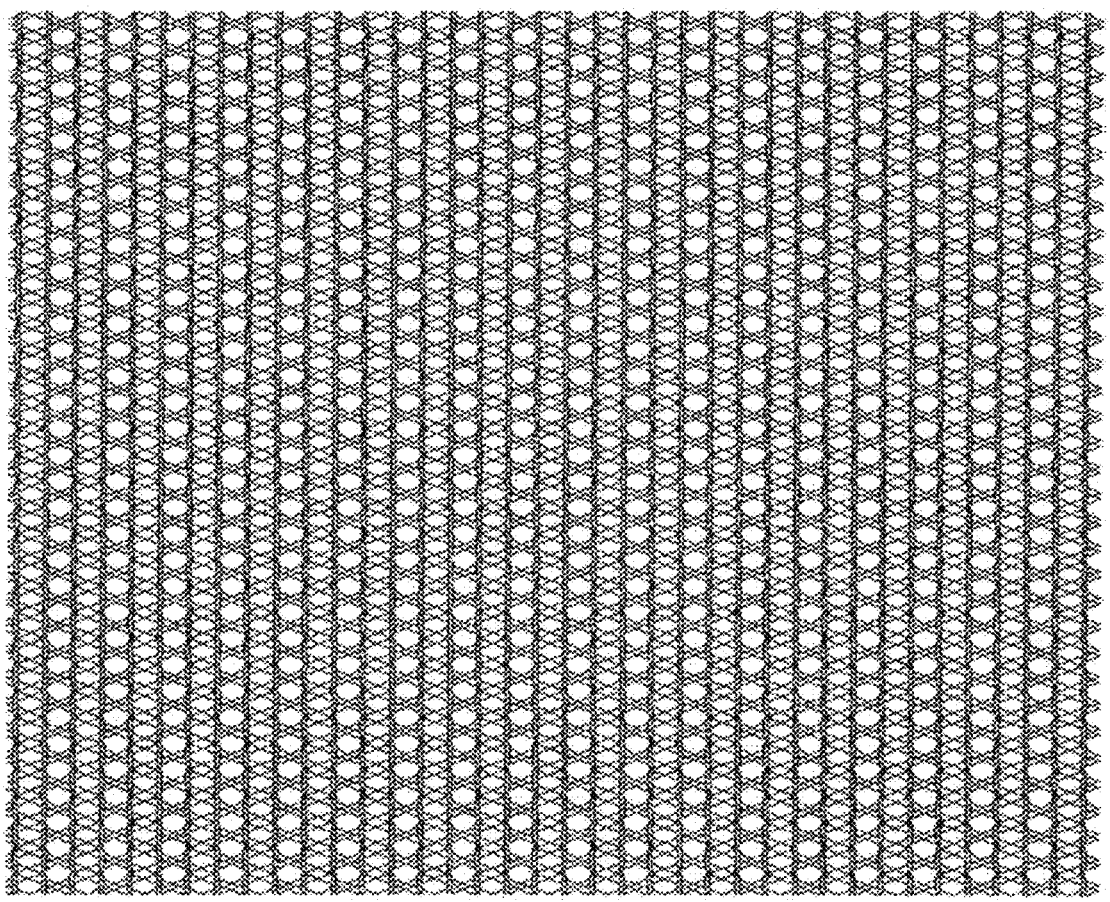
FIG. 16 illustrates the state of expansion of a warp knitted fabric prepared in Example 7 after decomposition and absorption of a yarn of a bioabsorbable material.
Figure 17:
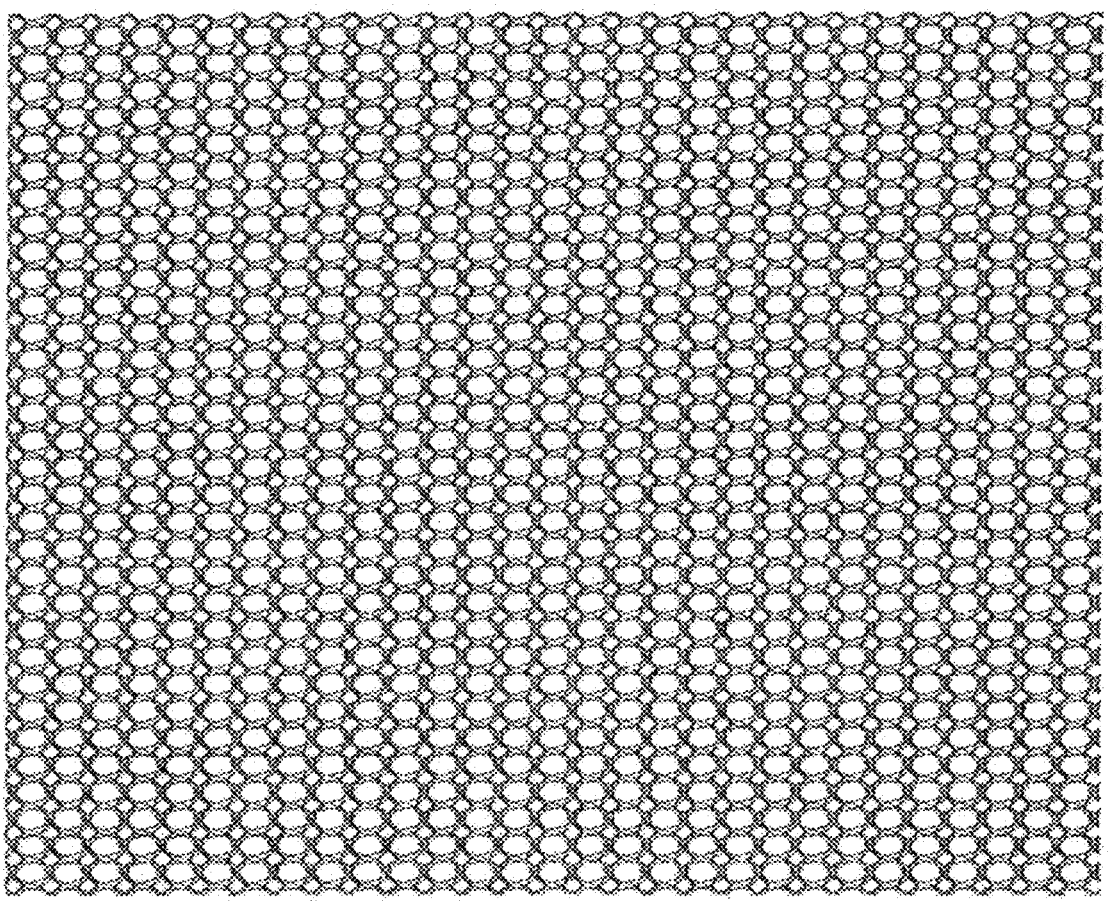
FIG. 17 illustrates the state of expansion of a warp knitted fabric prepared in Example 8 after decomposition and absorption of a yarn of a bioabsorbable material.
Figure 18:
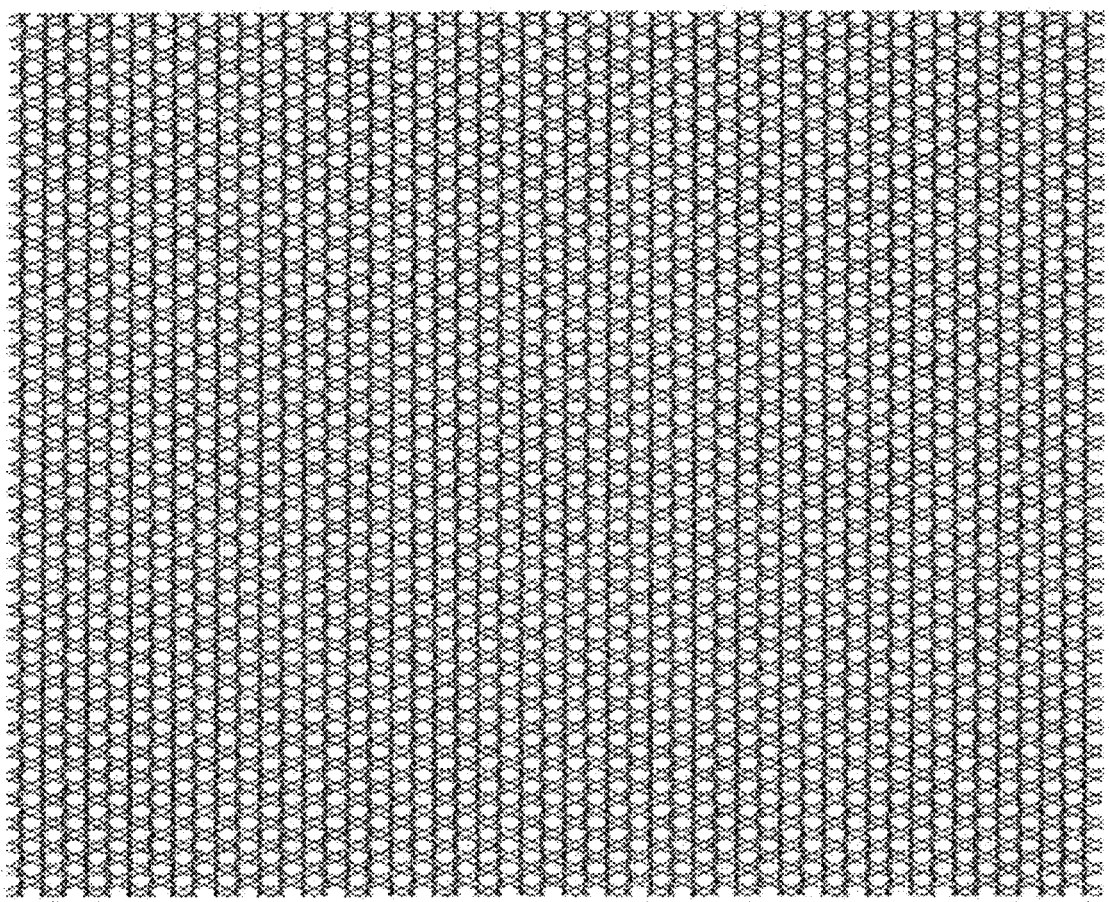
FIG. 18 illustrates the state of expansion of a warp knitted fabric prepared in Example 9 after decomposition and absorption of a yarn of a bioabsorbable material.

| | Figure number | Texture | Arrangement | 1st loop column:2nd loop column | Initial yarn arrangement (A = PET/B = PLA) | |
|---|---|---|---|---|---|---|
| | | | | | GB1(A)/GB2(B) | GB3(A)/GB4(B) |
| Ex. 1 | FIG. 10 | 14c atlas | 3in, 3out | 1:2 | A3/B3 | B2/A3/B3 |
| Ex. 2 | FIG. 11 | 14c atlas | 4in, 4out | 1:3 | A4/B4 | B4/A4 |
| Ex. 3 | FIG. 12 | 14c atlas | 4in, 4out | 1:3 | A4/B4 | B2/A4/B2 |
| Ex. 4 | FIG. 13 | 14c atlas | 5in, 5out | 1:4 | A5/B5 | A1/B5/A4 |
| Ex. 5 | FIG. 14 | 14c atlas | 6in, 6out | 1:5 | A6/B6 | B6/A6 |
| Ex. 6 | FIG. 15 | 14c atlas | 2in, 2out | 1:1 | A2/B2 | B2/A2 |
| Ex. 7 | FIG. 16 | 10c atlas | 2in, 2out | 1:1 | A2/B2 | B2/A2 |
| Ex. 8 | FIG. 17 | 8c atlas | 2in, 2out | 1:1 | A2/B2 | B1/A2/B1 |
| Ex. 9 | FIG. 18 | 6c atlas | 2in, 2out | 1:1 | A2/B2 | B2/A2 |

TABLE 3

| 14c atlas | GB1, GB2 | 10-12-23-34-45-56-67-78-76-65-54-43-32-21// |
|---|---|---|
| | GB3, GB4 | 78-76-65-54-43-32-21-10-12-23-34-45-56-67// |
| 10c atlas | GB1, GB2 | 10-12-23-34-45-56-54-43-32-21// |
| | GB3, GB4 | 56-54-43-32-21-10-12-23-34-45// |
| 8c atlas | GB1, GB2 | 10-12-23-34-45-43-32-21// |
| | GB3, GB4 | 45-43-32-21-10-12-23-34// |
| 6c atlas | GB1, GB2 | 10-12-23-34-32-21// |
| | GB3, GB4 | 34-32-21-10-12-23// |

The resultant warp knitted fabric was subjected to dissolution treatment with an aqueous NaOH solution until the rate simultaneous biaxial tensile test, i.e., stretched to double its initial length in a machine direction (MD) and a transverse direction (TD), with a biaxial stretching machine (manufactured by Toyo Seiki Seisaku-sho, Ltd.). Distance between chucks: 45 mm, rate: 50 mm/min, temperature: 37° C.

Example 11

A warp knitted fabric was prepared as in Example 1 except that the number of courses was changed to 60 in the knitting machine. A test sample was prepared from the warp knitted fabric and subjected to the constant-rate biaxial tensile test as in Example 10.

Example 12

A warp knitted fabric was prepared as in Example 1 except that the number of courses was changed to 90 in the knitting machine. A test sample was prepared from the warp knitted fabric and subjected to the constant-rate biaxial tensile test as in Example 10.

Comparative Example 2

A test sample was prepared from the warp knitted fabric of Comparative Example 1 and subjected to the constant-rate biaxial tensile test as in Example 10.

Table 5 and FIGS. 19(a) to 19(d) illustrate the results of evaluation of the test samples of Examples 10 to 12 and Comparative Example 2.

TABLE 5

| Maximum stretching load (N) | Example 10 | Example 11 | Example 12 | Comparative Example 2 |
|---|---|---|---|---|
| MD | 0.82 | 0.42 | 0.72 | 17.22 |
| TD | 0.43 | 0.17 | 0.46 | 7.18 |

The test results demonstrated that each of the warp knitted fabrics of Examples 10 to 12 was stretched to double its initial length by a force of less than 1 N. The warp knitted fabric of the present invention maintained an expanded mesh structure after being stretched to double its initial length. In contrast, the warp knitted fabric of Comparative Example 2 was broken after being stretched to about 1.4 times its initial length, due to application of a force of 10 N or more, i.e., the warp knitted fabric failed to be stretched to double its initial length.

Example (1) of Medical Material

[Preparation of Medical Material]

The warp knitted fabric of Example 1 prepared as described above was ultrasonically washed. The warp knitted fabric was cut into a circular shape (diameter: about 67 mm), and the circular warp knitted fabric was placed in an immersion container (flat petri dish, diameter: 68 mm, manufactured by Flat). A circular metal frame was placed on the warp knitted fabric to fix the fabric to the container. A predetermined amount of a 12% gelatin solution (MediGelatin, manufactured by Nippi, Incorporated) was added to the container, and the warp knitted fabric was immersed in the solution.

The container was cooled at 4° C. for 30 minutes to coat (seal) the warp knitted fabric with gelatin so as to prevent permeation of a fluid through the fabric. Separately, a 3% glutaraldehyde solution (50% glutaraldehyde solution, manufactured by Tokyo Chemical Industry Co., Ltd.) was cooled at 4° C. The cooled glutaraldehyde solution (4 mL) was added to the container, and reaction was allowed to proceed at 4° C. for one hour, to cross-link the gelatin. After completion of the reaction, the resultant product was washed with distilled water and dried under vacuum overnight. The dried product was immersed in 40% aqueous glycerin (Japanese Pharmacopoeia grade glycerin, manufactured by KENEI Pharmaceutical Co., Ltd.) (10 mL) for 20 minutes, to prepare a medical material composed of the gelatin-coated warp knitted fabric (hereinafter may be referred to as "sealed warp knitted fabric").

[Evaluation of Medical Material]
[Determination of the Amount of Hydrogel Coating]

The amount of hydrogel coating was determined on the basis of the difference between the weight of the warp knitted fabric before gelatin coating and that after gelatin coating.

[Determination of Thickness of Sealed Warp Knitted Fabric]

The thickness of a sealed warp knitted fabric sample was measured at five points with a micrometer (Quick Micro MDQ-30M, manufactured by Mitutoyo Corporation), and the measured values were averaged.

[Water Resistance Test]

Figure 21:
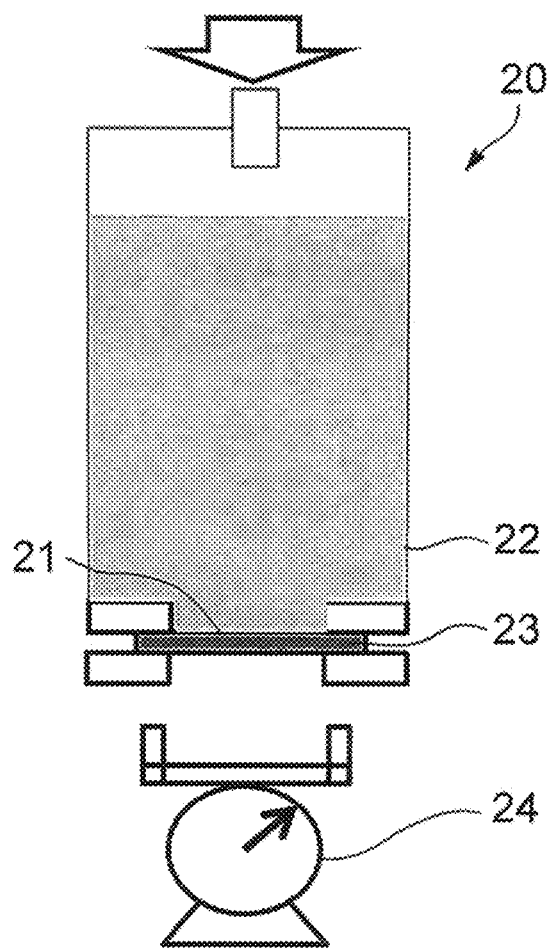
FIG. 21 is a schematic illustration of a leakage tester used for a water resistance test and a needle hole leakage test.
Figure 22:
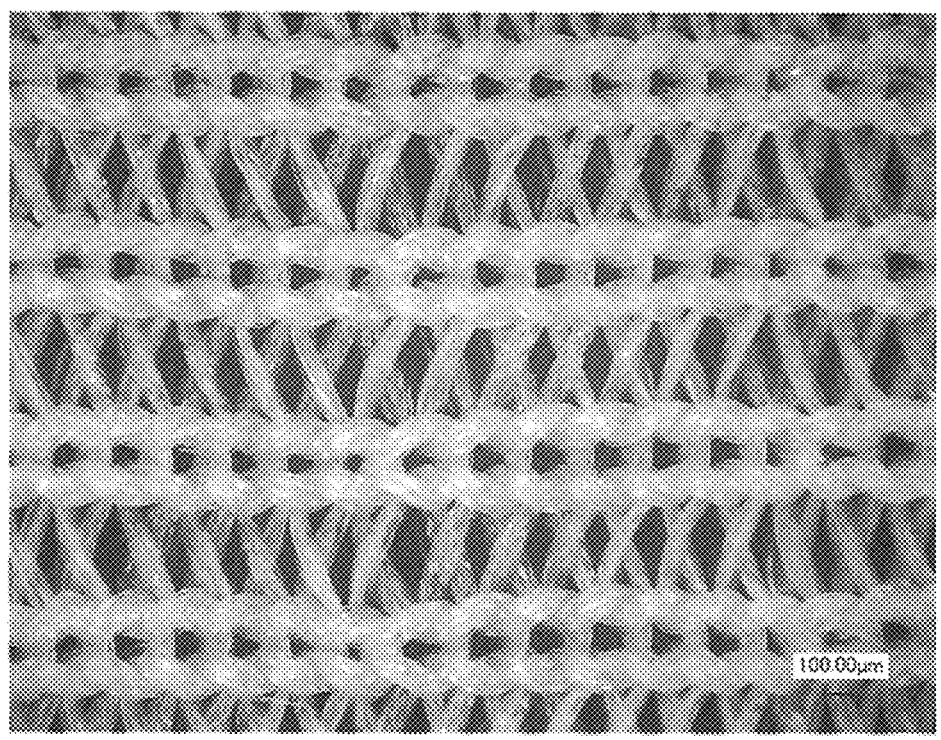
FIG. 22 is a micrograph of a warp knitted fabric before coating with gelatin.

Water resistance was evaluated with a leakage tester 20 illustrated in FIG. 21.

The peripheral surface of a sealed warp knitted fabric 23 was coated with a silicone adhesive sealing material (TSE392-W, manufactured by Momentive Performance Materials) so as to prevent leakage of water therethrough.

The sealed warp knitted fabric 23 was placed to come into contact with a bottom port 21 (diameter: 20 mm) at the bottom of a container 22 of the leakage tester 20. The container 22 was filled with distilled water, and a pressure of 150 mmHg (20 kPa) was applied to the water from above. Distilled water leaked from the bottom port 21 through the sealed warp knitted fabric 23 was recovered, and the amount of leaked water per minute was measured with an electronic balance 24. The test was performed three times, and the measured values were averaged.

[Needle Hole Leakage Test]

An artificial skin (Pro(S), manufactured by Nihon Light Service, Inc.) was five-needle sutured to the center of the sealed warp knitted fabric with a surgical suture (Prolene 6-0, manufactured by Ethicon), to prepare a test piece for testing needle hole leakage of a fluid. The test piece was placed in the leakage tester as in the water resistance test described above, and the container was filled with simulated blood (manufactured by Yamashina Seiki Co., Ltd.) at room temperature. A pressure of 150 mmHg (20 kPa) was applied to the simulated blood from above, and the amount of simulated blood leaked through the sealed warp knitted fabric 23 per minute was measured. The test was performed three times, and the measured values were averaged.

[Optical Micrograph of Sealed Warp Knitted Fabric]

The sealed warp knitted fabric was cut into a predetermined size and prefixed with 2.5% glutaraldehyde at 4° C. for two hours. The sealed warp knitted fabric was then washed with 0.1M phosphate buffer for two hours and postfixed with 1% osmium tetroxide at 4° C. for two hours. Subsequently, the sealed warp knitted fabric was sequentially subjected to dehydration with 50% ethanol for 10 minutes, 70% ethanol for 20 minutes, 80% ethanol for 20 minutes, 90% ethanol for 30 minutes, 95% ethanol for 30 minutes, and 100% ethanol for 30 minutes. Thereafter, the resultant sealed warp knitted fabric was sequentially subjected to contact with n-butyl glycidyl ether (QY-1, manufactured by Nisshin EM Co., Ltd.) for 30 minutes, a 1:1 mixture of QY-1 and epoxy resin (Epon812 resin) for 30 minutes, a 1:2 mixture of QY-1 and epoxy resin for 30 minutes, a 1:3 mixture of QY-1 and epoxy resin for 30 minutes, and epoxy resin overnight. The sealed warp knitted fabric was then cured at 60° C. The cured sample was sectioned with an ultramicrotome into a slice having a thickness of 1 μm. The slice was stained with toluidine blue, and the top surface and cross section of the stained slice were observed and photographed with a digital microscope (manufactured by KEYENCE CORPORATION).

Example 13

Figure 23:
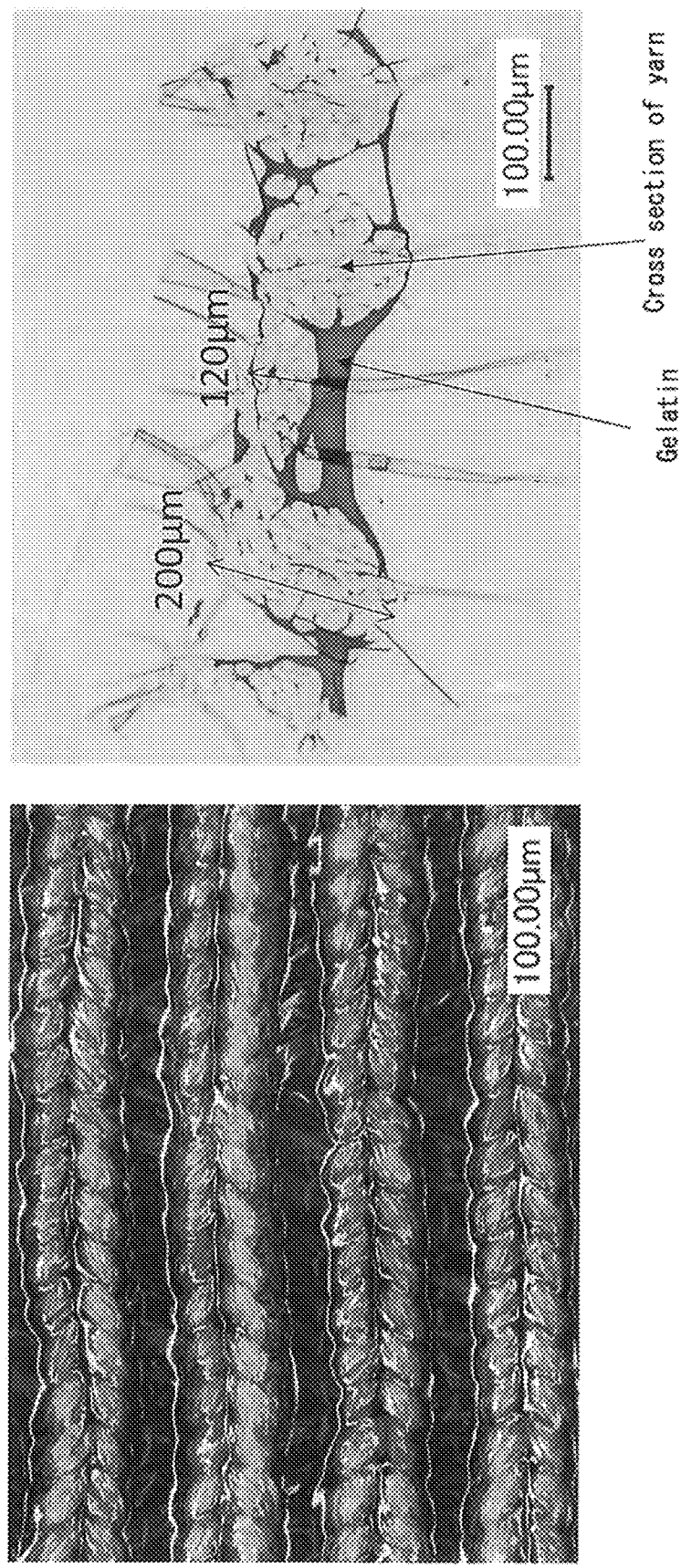
FIG. 23(a) is a micrograph of the top surface of a medical material prepared in Example 13.
FIG. 23(b) is a photograph of a cross section of the medical material.

A gelatin-sealed warp knitted fabric was prepared in the same manner as described above through addition of a 12% gelatin solution (1.0 mL). The resultant sealed warp knitted fabric had a gelatin coating of 3.59 mg/cm$^2$ and a thickness of 0.22 µm. The sealed warp knitted fabric was micrographed. As illustrated in FIG. 23, gelatin was deposited on the surfaces of yarns and between yarns. The water resistance test of the fabric showed no leakage of water (0 g/min), and the needle hole leakage test of the fabric showed a slight leakage of simulated blood (0.1 g/min). The results of evaluation demonstrated that the sealed warp knitted fabric exhibited superior properties.

Example 14

A gelatin-sealed warp knitted fabric was prepared in the same manner as described above through addition of a 12% gelatin solution (2.0 mL). The resultant sealed warp knitted fabric had a gelatin coating of 4.93 mg/cm$^2$ and a thickness of 0.24 µm. The sealed warp knitted fabric was micrographed. As illustrated in FIG. 24, gelatin was deposited on the surfaces of yarns and between yarns. The water resistance test of the fabric showed no leakage of water (0 g/min), and the needle hole leakage test of the fabric showed a leaked simulated blood (0.04 g/min). The results of evaluation demonstrated that the sealed warp knitted fabric exhibited superior properties.

Example 15

A gelatin-sealed warp knitted fabric was prepared in the same manner as described above through addition of a 12% gelatin solution (3.0 mL). The resultant sealed warp knitted fabric had a gelatin coating of 6.34 mg/cm$^2$ and a thickness of 0.35 µm. The sealed warp knitted fabric was micrographed. As illustrated in FIG. 25, gelatin was deposited on the surfaces of yarns and between yarns. The water resistance test of the fabric showed no leakage of water (0 g/min), and the needle hole leakage test of the fabric showed a leaked simulated blood (0.05 g/min). The results of evaluation demonstrated that the sealed warp knitted fabric exhibited superior properties.

Example 16

A gelatin-sealed warp knitted fabric was prepared in the same manner as described above through addition of a 12% gelatin solution (0.5 mL). The resultant sealed warp knitted fabric had a gelatin coating of 1.86 mg/cm$^2$ and a thickness of 0.20 µm. The water resistance test of the fabric showed a leakage of water (4.2 g/min), and the needle hole leakage test of the fabric showed a relatively large leakage of simulated blood (750 g/min or less).

<Comparative Example of Medical Material>

Comparative Example 3

A gelatin-uncoated warp knitted fabric was subjected to the water resistance test and the needle hole leakage test. The warp knitted fabric exhibited a leakage of water (1,000 g/min or more) and a leakage of simulated blood (1,000 g/min or more) within a short period of time.

Table 6 illustrates the results of evaluation of the aforementioned medical materials.

TABLE 6

|  | Example 13 | Example 14 | Example 15 | Example 16 | Comparative Example 3 |
|---|---|---|---|---|---|
| Coating amount (mg/cm$^2$) | 3.59 | 4.93 | 6.34 | 1.86 | 0 |
| Thickness after coating (µm) | 0.22 | 0.24 | 0.35 | 0.20 | 0.20 |
| Water resistance test (g/min) | 0 | 0 | 0 | 4.2 | 1000< |
| Needle hole leakage test (g/min) | 0.1 | 0.04 | 0.05 | 750> | 1000< |

<Example of Implantation in Dog>

A warp knitted fabric was implanted on the vascular walls of the inferior vena cava and descending aorta of a dog. The warp knitted fabric was evaluated as described below.

[Sealed Warp Knitted Fabric for Use in Implantation]

The sealed warp knitted fabric for implantation on the vascular wall of the inferior vena cava was prepared through the process described in Example 1 and the section [Preparation of medical material]. In detail, the sealed warp knitted fabric was prepared under the following conditions.

Yarn composed of bioabsorbable material: yarn of poly (lactic acid) (33T1, manufactured by TEIJIN LIMITED)

Yarn composed of non-bioabsorbable material: yarn of poly(ethylene terephthalate) (33T12, type 262, manufactured by Toray Industries, Inc.)

Knitting machine condition: 32 gauges, 130 courses

Density (after thermal setting): 35 wales/inch, 127 courses/inch

Texture: 14c atlas

Arrangement: 3in, 3out

Amount of added gelatin: 36.0 mL

Amount of gelatin coating: 3.3 mg/cm$^2$

The sealed warp knitted fabric for implantation on the vascular wall of the descending aorta was also prepared through the process described in Example 1 and the section [Preparation of medical material]. In detail, the sealed warp knitted fabric was prepared under the following conditions such that both surfaces of the fabric were evenly coated with gelatin.

Yarn composed of bioabsorbable material: yarn of poly (lactic acid) (33T12, manufactured by TEIJIN LIMITED)

Yarn composed of non-bioabsorbable material: yarn of poly(ethylene terephthalate) (33T12, type 262, manufactured by Toray Industries, Inc.)

Knitting machine condition: 32 gauges, 120 courses

Density (after thermal setting): 36 wales/inch, 117 courses/inch

Texture: 14c atlas

Arrangement: 3in, 3out

Amount of added gelatin: 1.2 mL

Amount of gelatin coating: 3.82 mg/cm$^2$

[Anesthesia]

Anesthesia of a test dog was induced with intravenous administration of thiamylal sodium (Isozol, manufactured by Nichi-Iko Pharmaceutical Co., Ltd.) (22.5 mg/kg: the dose was appropriately adjusted on the basis of the degree of anesthesia during administration). Saline was infused through the cephalic vein for prevention of dehydration. A tracheal catheter was inserted into the trachea, and the dog was subjected to mechanical ventilation with an animal ventilator (manufactured by ACOMA Co., Ltd.) (15 strokes/min, tidal volume: 20 mL/kg/stroke as a standard). Anesthesia was maintained by inhalation of a mixed gas (Air: $O_2$=3:0.2 as a standard) and 0.5 to 3% isoflurane (Forane inhalational anesthetic, manufactured by AbbVie) with an animal anesthesia apparatus (manufactured by ACOMA Co., Ltd.).

[Implantation in Vascular Wall of the Inferior Vena Cava]

A dog anesthetized as described above (beagle, four months old, body weight at implantation: 6.7 kg, available from Hamaguchi Laboratory Animals) was placed in the left decubitus position, the right lateral chest wall was shaved and disinfected with an iodine solution. Thereafter, the right thorax was entered through the fourth intercostal lateral wall. The inferior vena cava was longitudinally incised by 20 mm, and the sealed warp knitted fabric prepared as described above (elliptical shape with dimensions of 23 mm by 8 mm) was into implanted the incision made in the vessel by circumferential suture.

[Implantation on Vascular Wall of Descending Aorta]

A dog anesthetized as described above (beagle, 20 months old, body weight at implantation: 8.9 kg, available from Hamaguchi Laboratory Animals) was placed in the right decubitus position, the left lateral chest wall was shaved, and disinfected with an iodine solution. The left chest was then entered through the fourth intercostal lateral wall. Subsequently, the aortic arch was identified and the descending aorta was dissected. An implantation site in the descending aorta was determined, and heparin (400 IU/aminal) was intravenously administered for a bypass at the implantation site. The centers of purse-string sutures on proximal and distal to the implantation site were incised with a scalpel, and two cannulae were inserted into the two incised portions and then connected together to establish a bypass circuit. The descending aorta was then clamped at the proximal and distal to the implantation site. The descending aorta was incised longitudinally by 20 mm between these two clamps, and the vascular wall was resected with dimensions of 20 mm by 12 mm. The sealed warp knitted fabric prepared as described above (elliptical shape with dimensions of 20 mm by 12 mm) was implanted the wall defect by circumferential suture. Thereafter, the two vascular clamps applied proximal and distal to the implantation site were released, and protamine sulfate was intravenously administered at a dose of 4 mg/animal (0.4 mL/animal of a 10 mg/mL protamine sulfate solution). Blood leakage of blood through the implantation site was controlled by additional suture, compression with gauze, or application of a fibrin sealant (TachoSil, manufactured by CSL Behring). The cannulea for bypass were removed, followed by ligation on of the purse-string sutures. After confirmation of no blood leakage of at the implantation site and the purse-string suture, a chest tube was inserted into the left thoracic cavity, and the chest was closed. After thoracic cavity drainage, the chest tube was removed and the surgical incision was closed. After hemostasis, a drain was inserted and the thorax was closed. For postsurgical pain relief, butorphanol tartrate (Vetorphale, manufactured by Meiji Seika Pharma Co., Ltd.) was intramuscularly administered at a dose of 0.1 mg/kg after the surgery and before arousal.

[Tissue Extirpation and Sample Preparation]

After the elapse of a predetermined postsurgical period, the test dog was euthanized by excessive anesthesia. Subsequently, the vascular tissue at the site of implantation of the sealed warp knitted fabric was removed and longitudinally incised at the opposite of the fabric. The vascular specimen was fixated with a 4% paraformaldehyde solution and then refrigerated. The resultant tissue section was dehydrated with ethyl alcohol and then impregnated with paraffin (via xylene serving as an intermediate agent), to prepare a paraffin-embedded block. The block was sliced into thin samples with a thickness of about 4 to 5 µm. The slices were stained with hematoxylin and eosin (HE) and alizarin red (AR), and immunostained for von Willebrand factor (vWF) and α-smooth muscle actin (αSMA).

[Immunostaining]

Anti-vWF rabbit polyclonal antibody (DAKO Cytomation A/S, Glostrup, Denmark) (diluted at 1:2500) or anti-SMA mouse monoclonal antibody (clone 1A4, DAKO) (diluted at 1:500) were used as primary antibodies for immunostaining. Each of the primary antibodies was reacted with the slices at 4° C. overnight. HRP-labeled anti-rabbit IgG goat polyclonal antibody (Nichirei, Tokyo, Japan) or HRP-labeled anti-mouse IgG goat polyclonal antibody (Nichirei, Tokyo, Japan) were used as secondary antibodies for vWF or SMA, respectively. Each of the secondary antibodies was reacted with each primary antibodies, and the resultant antigen-antibody reaction product was visualized through dark brown coloration by 3,3'-diaminobenzidine (DAB), followed by counterstaining with hematoxylin.

[Imaging]

Microscopic images were captured with a fluorescent microscope (BX53, manufactured by Olympus Corporation) and a microscopic digital camera (DP73, manufactured by Olympus Corporation).

Example 17

Implantation into the Vascular Wall of the Inferior Vena Cava

A sealed warp knitted fabric prepared as described above was implanted into the vascular wall of the inferior vena cava of a test dog through the aforementioned process. Neither blood leakage of nor rupture was observed at a implantation site of the sealed warp knitted fabric.

Figure 26:
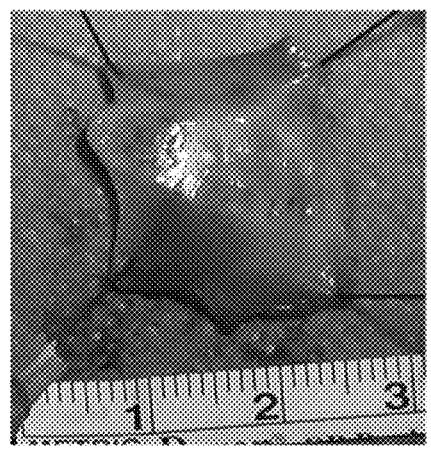
FIG. 26 is a photograph of the appearance of the intima of the inferior vena cava six months after implantation of a medical material prepared in Example 17.
Figure 27:
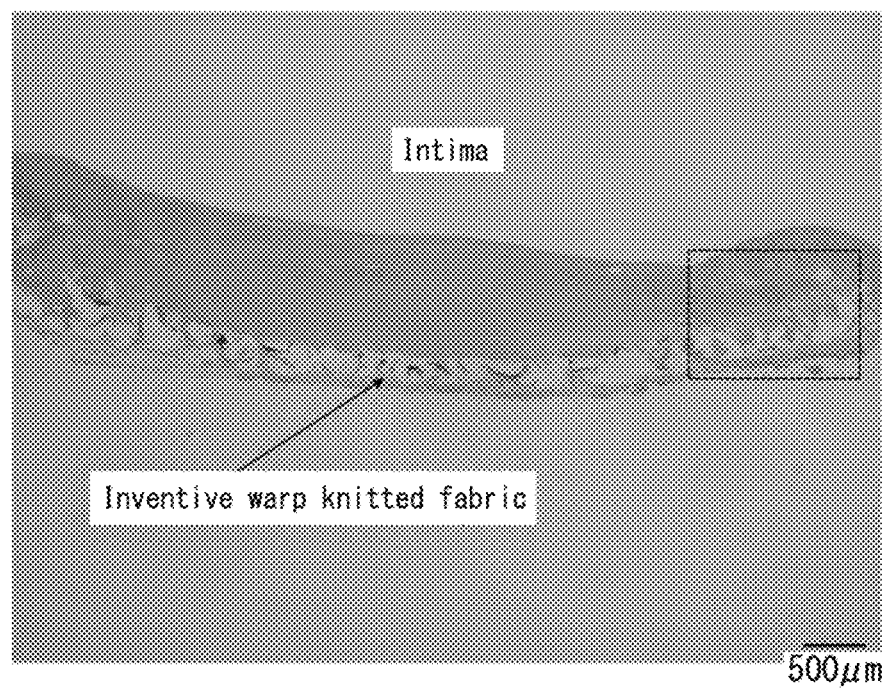
FIG. 27 is a photograph of the HE-stained vascular wall of the inferior vena cava six months after implantation of the medical material prepared in Example 17 (Bar=500 µm).
Figure 28:
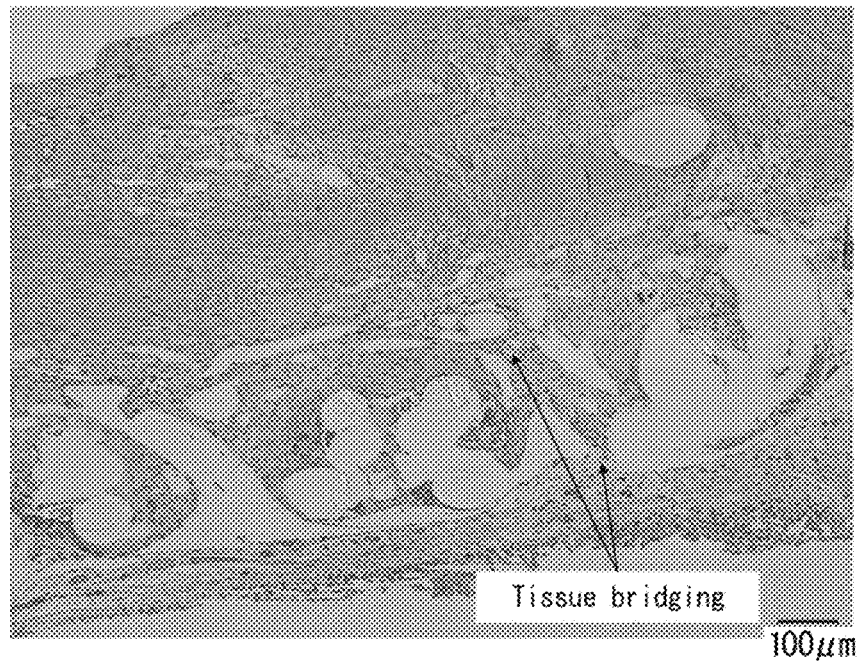
FIG. 28 is an enlarged photograph of a portion enclosed by a dotted line illustrated in FIG. 27 (Bar=100 µm).

The test dog was euthanized six months after the surgery, and the vascular tissue at the site of implantation of the sealed warp knitted fabric was prepared into a sample by the aforementioned process. FIG. 26 is a photograph of the sample. FIGS. 27 and 28 illustrate a tissue section in the vicinity of the suture, the section being stained with hematoxylin and eosin (HE) by the aforementioned process. FIG.

Figure 30:
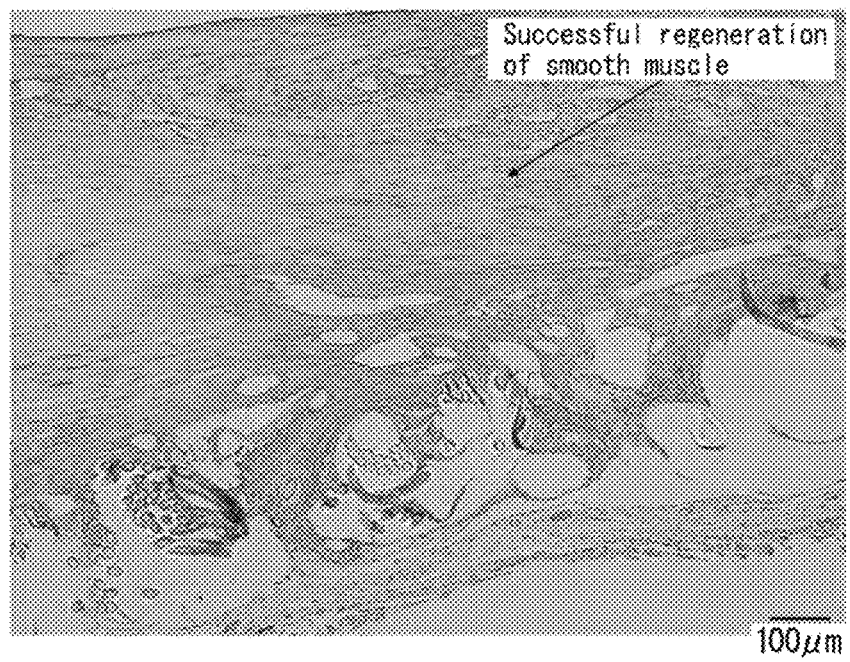
FIG. 30 is a photograph of the αSMA-stained vascular wall of the inferior vena cava six months after implantation of the medical material prepared in Example 17 (Bar=100 µm).
Figure 31:
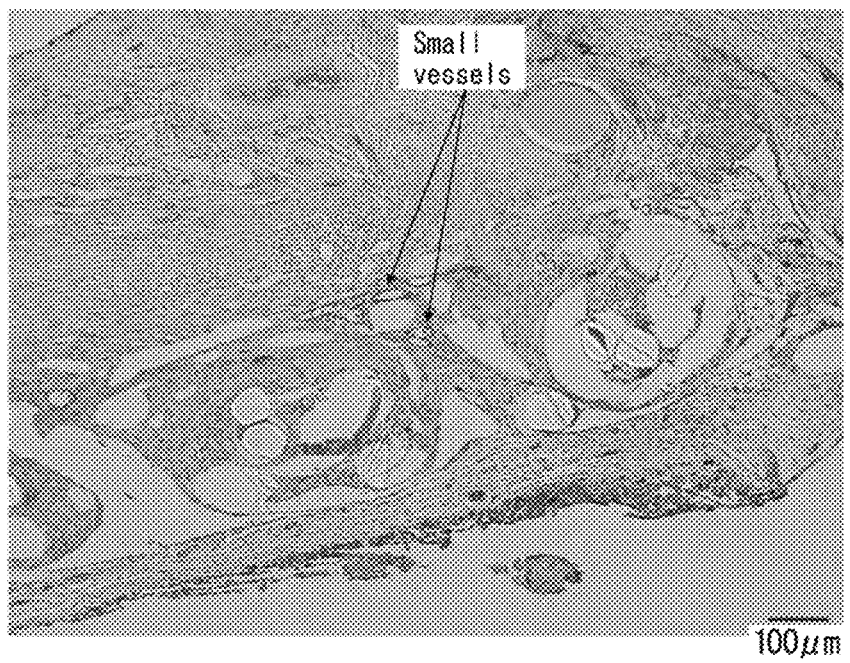
FIG. 31 is a photograph of the vWF-stained vascular wall of the inferior vena cava six months after implantation of the medical material prepared in Example 17 (Bar=100 µm).

29 is a microscopic photograph of the tissue section stained with alizarin red (AR). FIG. 30 is a microscopic photograph of the tissue section stained for α-smooth muscle actin (αSMA), and FIG. 31 is a microscopic photograph of the tissue section stained for von Willebrand factor (vWF).

Figure 29:
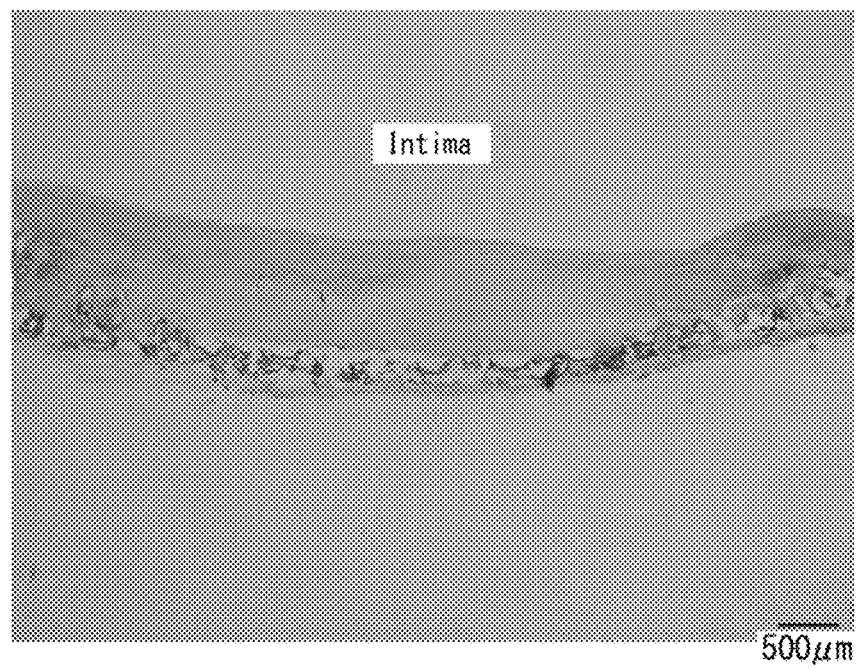
FIG. 29 is a photograph of the alizarin red-stained vascular wall of the inferior vena cava six months after implantation of the medical material prepared in Example 17 (Bar=500 µm).

FIG. 26 illustrates that the border of the site of implantation of the sealed warp knitted fabric was unclear six months after the surgery, which indicates successful regeneration of the intimal layer. FIGS. 27 and 28 demonstrate disappearance of the gelatin in the sealed warp knitted fabric at the implantation site, replacement of the gelatin with regenerated autologous tissue, and bridging tissue across both surfaces of the warp knitted fabric. FIG. 29 illustrates no calcium deposition due to cell death. This suggests that the sealed warp knitted fabric of the present invention has biocompatibility because it does not cause foreign-body reaction to the medical material often resulting in calcification. FIG. 30 illustrates the presence of smooth muscle actin fiber in the tissue of the implantation site, which demonstrates successful tissue regeneration. FIG. 31 illustrates the presence of vascular tissues in the regenerated tissue among filaments of the warp knitted fabric, which suggests long-term engraftment of the newly developed tissue, without exfoliation, seen in pseudointima.

Example 18

Implantation into the Vascular Wall of the Descending Aorta

A sealed warp knitted fabric prepared as described above was implanted into the vascular wall of the descending aorta of a test dog through the aforementioned process. Neither blood leakage nor rupture was observed at the implantation site of the sealed warp knitted fabric.

Figure 32:
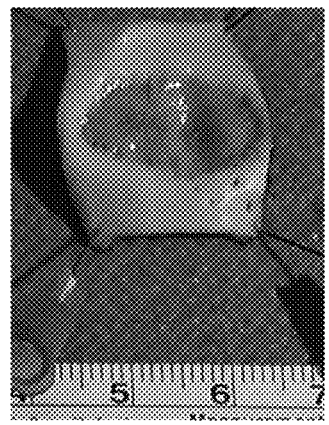
FIG. 32 is a photograph of the appearance of the intima of the inferior vena cava three months after implantation of a medical material prepared in Example 18.
Figure 33:
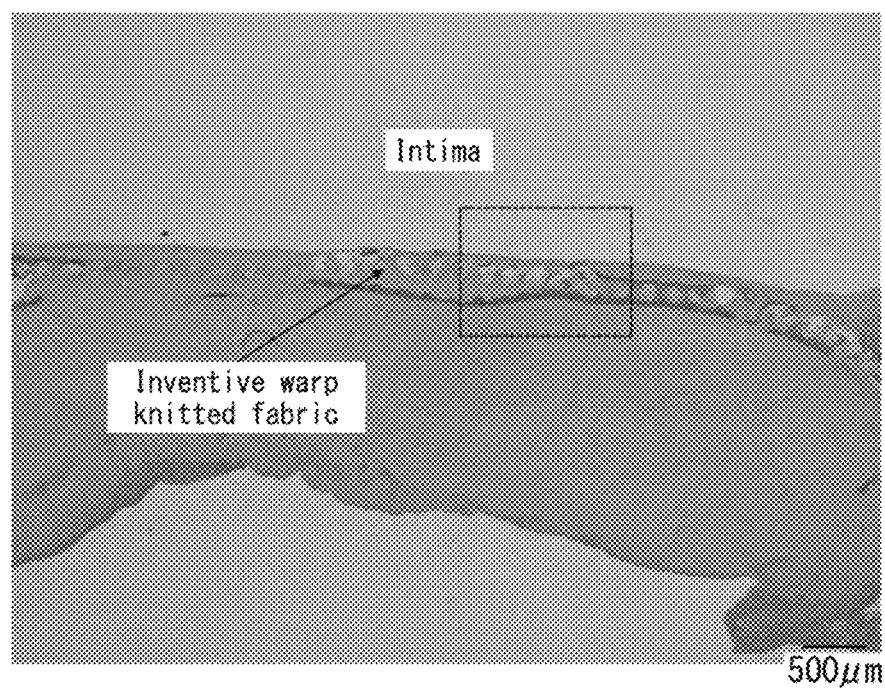
FIG. 33 is a photograph of the HE-stained vascular wall of the inferior vena cava three months after implantation of the medical material prepared in Example 18 (Bar=500 µm).
Figure 34:
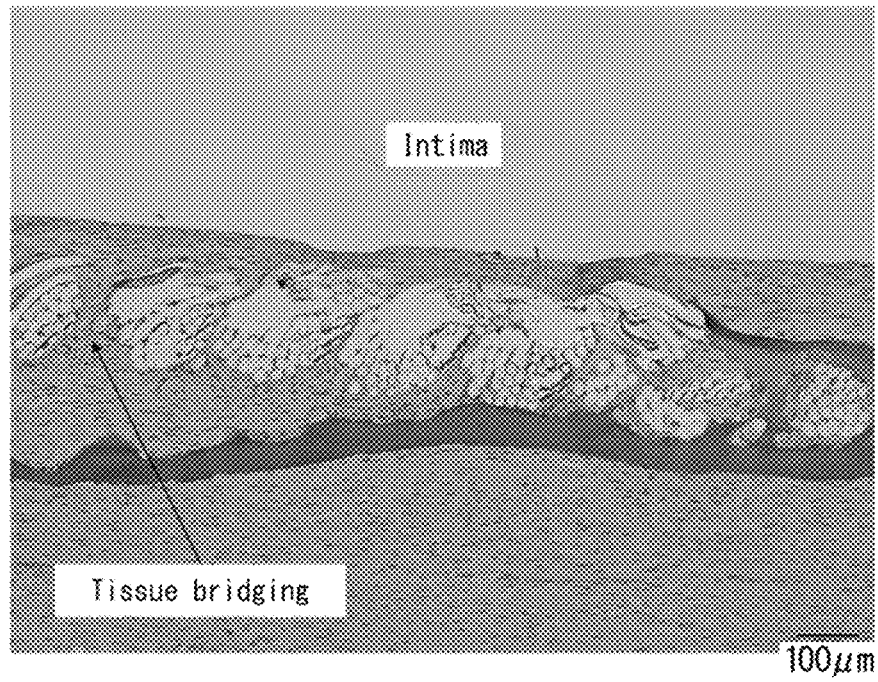
FIG. 34 is an enlarged photograph of a portion enclosed by a dotted line illustrated in FIG. 33 (Bar=100 µm).
Figure 35:
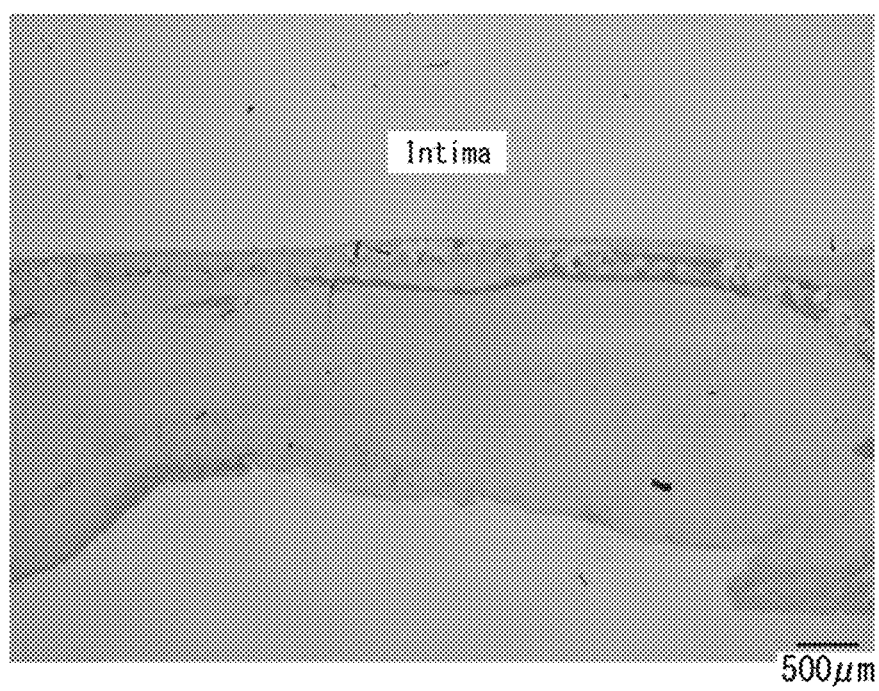
FIG. 35 is a photograph of the alizarin red-stained vascular wall of the interior vena cava three months after implantation of the medical material prepared in Example 18 (Bar=500 µm).
Figure 36:
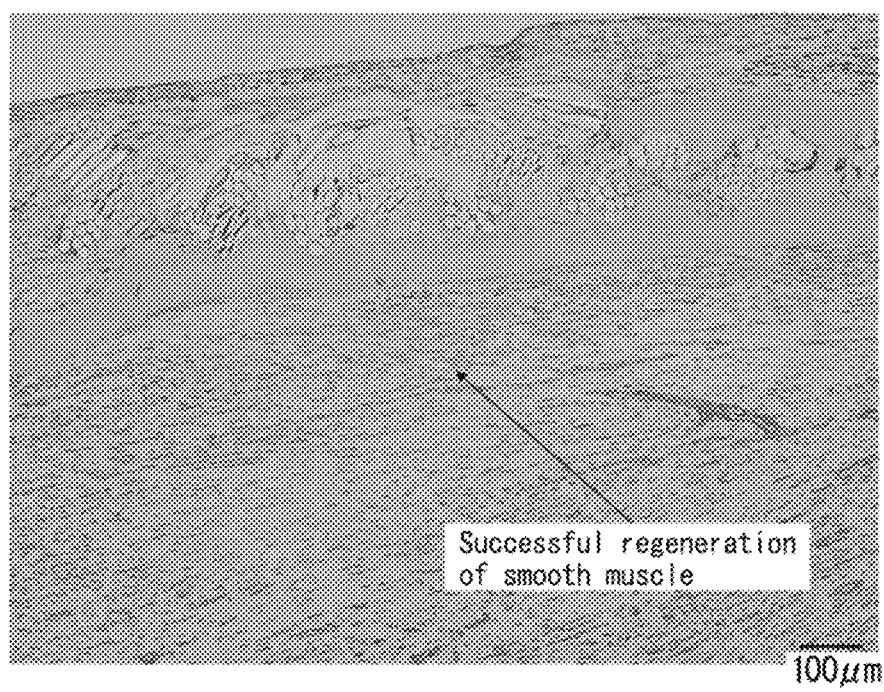
FIG. 36 is a photograph of the αSMA-stained vascular wall of the inferior vena cava three months after implantation of the medical material prepared in Example 18 (Bar=100 µm).

The test dog was euthanized three months after the surgery, and the vascular tissue at the site of implantation of the sealed warp knitted fabric was prepared into a sample by the aforementioned process. FIG. 32 is a photograph of the sample. FIGS. 33 and 34 are microscopic photograph of a tissue section in the vicinity of the suture, the section being stained with hematoxylin and eosin (HE) by the aforementioned process. FIG. 35 is a microscopic photograph of the tissue section stained with alizarin red (AR). FIG. 36 is a micrograph of the tissue section stained with α-smooth muscle actin (αSMA).

FIG. 32 demonstrates successful regeneration of the intima at the site of implantation of the sealed warp knitted fabric three months after the surgery. FIGS. 33 and 34 demonstrate regeneration of autologous tissue and tissue bridging tissue across the fabric at the implantation site. FIG. 35 illustrates no calcium deposition, which suggests that the sealed warp knitted fabric of the present invention serves as a medical material having biocompatibility enough not to cause calcification by foreign-body reaction to the medical material or cell death in the material. FIG. 36 illustrates the presence of smooth muscle actin fiber in the tissue, which suggests successful tissue regeneration. Another test dog was euthanized six months after the surgery, and the state of the tissue at the site of implantation was observed. No vascular stenosis occurred, and successful tissue regeneration and maintenance were observed as in the case of the dog three months after the surgery.
<Comparative Example of Implantation in Dog>

A bovine pericardial membrane patch was implanted into the vascular wall of the inferior vena cava of a dog. Evaluation of the bovine pericardial membrane patch was performed as described below. The anesthesia, sample preparation, immunostaining, and imaging processes, other than the implantation process, were performed as in Example 18.
[Implantation of Bovine Pericardial Membrane Patch into the Vascular Wall of the Inferior Vena Cava]

An elliptical portion (major axis length: 2 cm, minor axis length: 1.5 cm) of the inferior vena cava was excised using a dog (beagle, body weight during implantation: 10.7 kg, available from Hamaguchi Laboratory Animals). A commercial bovine pericardial membrane patch (elliptical shape having dimensions of 25 mm by 15 mm, serial number: 4700, manufactured by Edwards Lifesciences Corporation) was implanted into the elliptical portion of the inferior vena cava.

Comparative Example 4

As described above, the bovine pericardial membrane patch was implanted into the vascular wall of the inferior vena cava of the dog. Neither blood leakage nor rupture was observed at a site of implantation of the bovine pericardial membrane patch.

Figure 37:
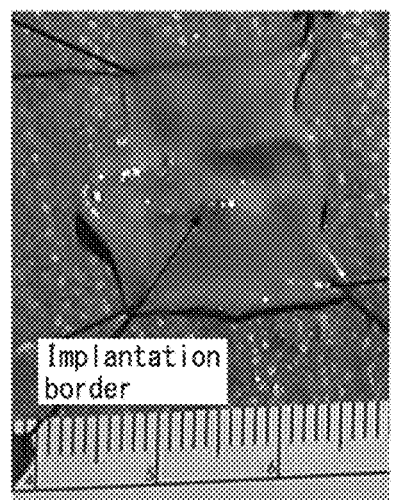
FIG. 37 is a photograph of the appearance of the intima of the inferior vena cava six months after implantation of a bovine pericardial membrane.
Figure 38:
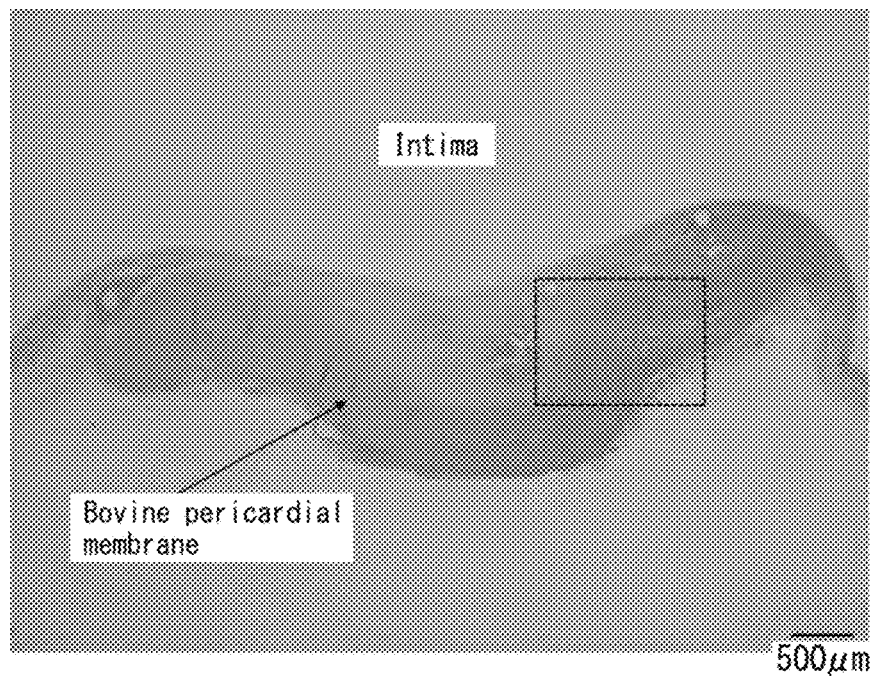
FIG. 38 is a photograph of the HE-stained vascular wall of the inferior vena cava six months after implantation of a bovine pericardial membrane (Bar=500 μm).
Figure 39:
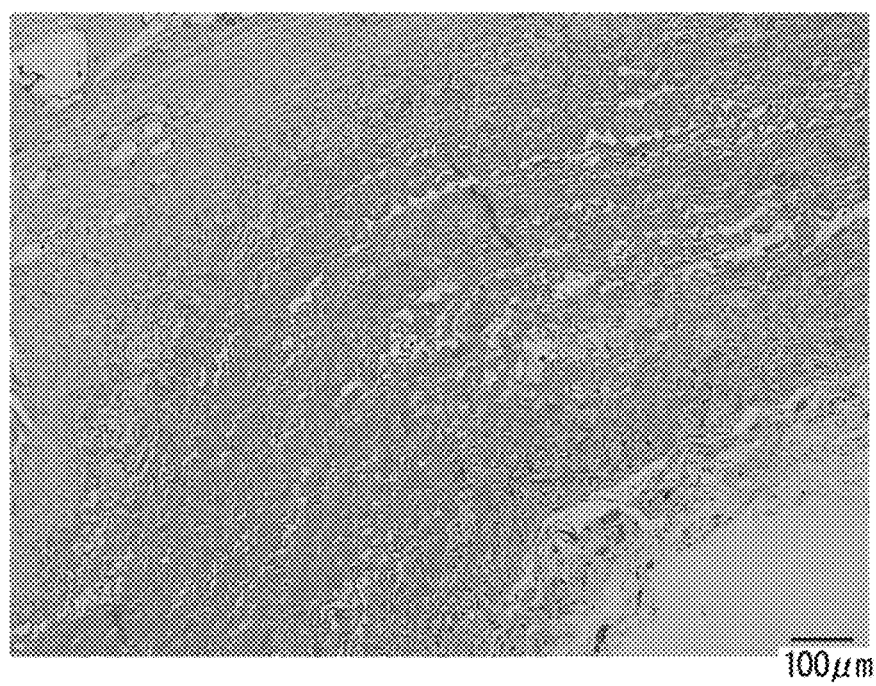
FIG. 39 is an enlarged photograph of a portion enclosed by a dotted line illustrated in FIG. 38 (Bar=100 μm).
Figure 40:
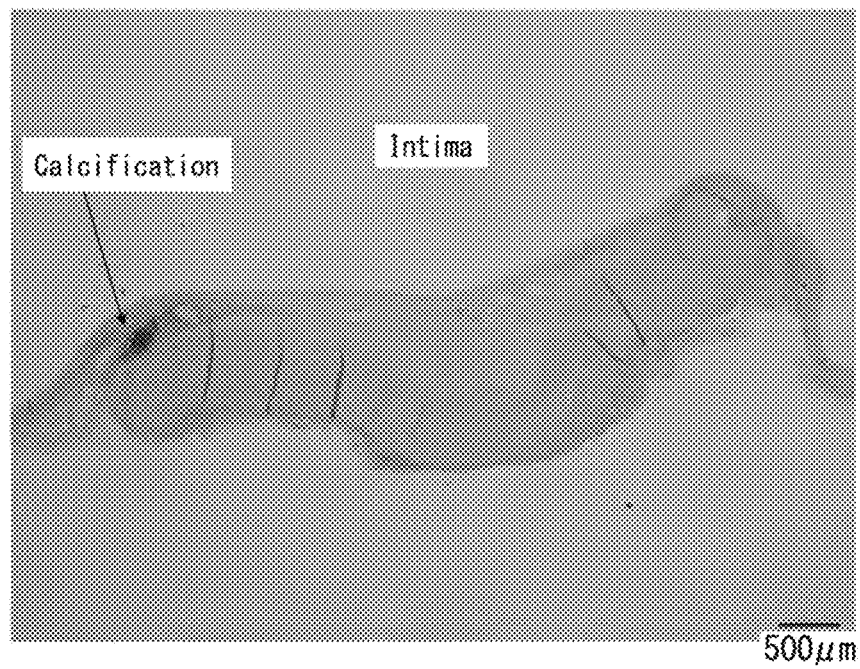
FIG. 40 is a photograph of the alizarin red-stained vascular wall of the inferior vena cava six months after implantation of a bovine pericardial membrane (Bar=500 μm).
Figure 41:
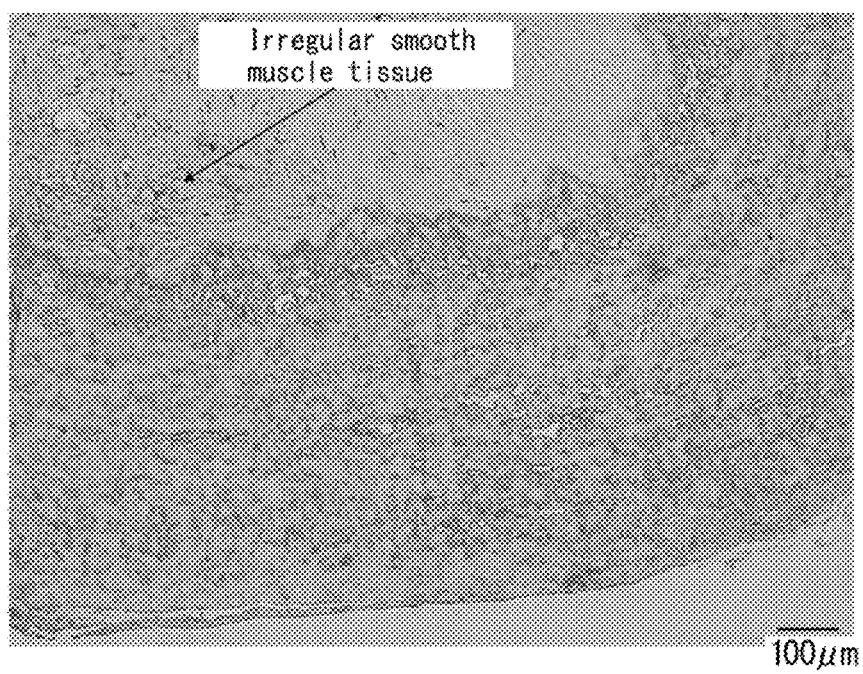
FIG. 41 is a photograph of the αSMA-stained vascular wall of the inferior vena cava six months after implantation of a bovine pericardial membrane (Bar=100 μm).
Figure 42:
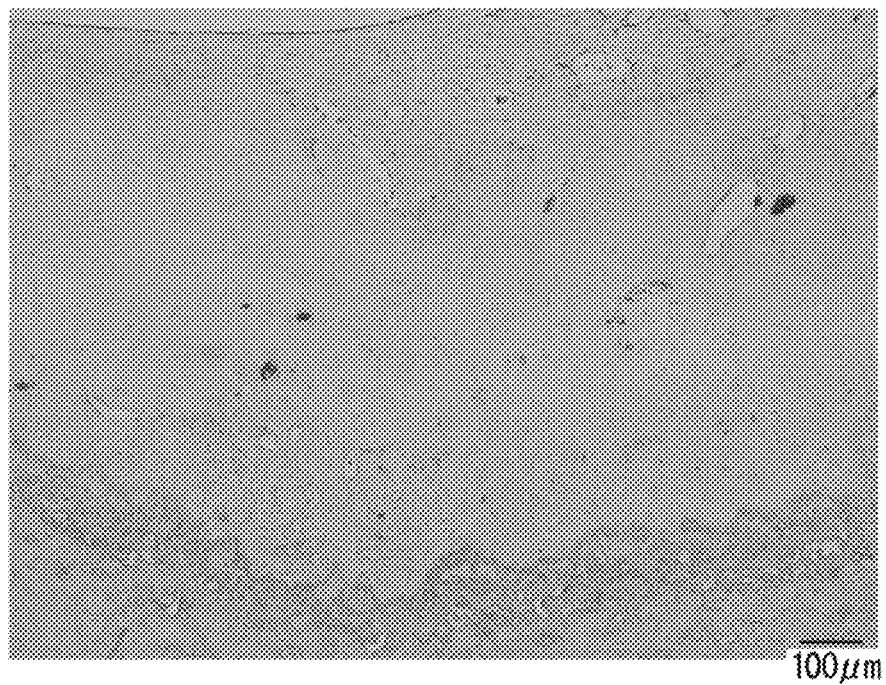
FIG. 42 is a photograph of the vWF-stained vascular wall of the inferior vena cava six months after implantation of a bovine pericardial membrane (Bar=100 μm).

The dog was euthanized six months after the surgery. A vascular tissue at the site of implatation of the bovine pericardial membrane was removed by the aforementioned process. FIG. 37 is a photograph of the longitudinally incised tissue at the site of implatation of the bovine pericardial membrane. The tissue section was stained by the aforementioned process. FIGS. 38 and 39 are microscopic photographs of the tissue section in the vicinity of the suture, the section being stained with hematoxylin and eosin (HE). FIG. 40 is a microscopic photograph of the tissue section stained with alizarin red (AR). FIG. 41 is a microscopic photograph of the tissue section stained with α-smooth muscle actin (αSMA). FIG. 42 is a microscopic photograph of the tissue section stained with von Willebrand factor (vWF).

FIG. 37 illustrates that the border of the implanted bovine pericardial membrane patch was clearly identified six months after the surgery, which suggests insufficient regeneration of the intimal tissue. FIG. 38 illustrates the intimal tissue on the implantation site thickened as compared with that of the native wall. Thickening of the vascular intima may lead to vascular stenosis, resulting in distal blood flow disturbance. FIG. 39 illustrates no new tissue formed inside in the bovine pericardial membrane. FIG. 40 illustrates calcium deposition in the vicinity of the implantation border, which suggests the occurrence of foreign-body reaction. FIG. 41 illustrates that newly developed collagen fiber and myofibril are in an irregular, non-laminar, form. FIG. 42 illustrates no vascular tissue between filaments of the warp knitted fabric. These findings demonstrate that the bovine pericardial membrane is inferior to the sealed warp knitted fabrics of Examples 17 and 18.

Example (2) of Medical Material

[Preparation of Medical Material]
A gelatin-coated warp knitted fabric was prepared as in the Examples described above.
[Evaluation of Medical Material]
[Swelling]
The sealed warp knitted fabric was thoroughly dried and cut into a sample having dimensions of 30 mm by 30 mm. The initial weight (M1 (mg)) of the sample was measured. The warp knitted fabric sample was placed in a bottle, and ultrapure water (100 mL) was added to the bottle. The sample was immersed in the water for 24 hours. Thereafter, the sample was removed from the bottle, and moisture on the surface of the sample was eliminated with Kimwipes, followed by measurement of the weight (M2 (mg)) of the sample.

The swelling (%) of the hydrogel was calculated by Formula (I):

$$\text{Swelling (\%)} = [(M2-M1)/\text{amount of coating (mg)}] \times 100 \quad \text{(I)} \quad [F3]$$

(M1: the weight (mg) of sample before immersion, M2: the weight (mg) of sample after immersion)

[Needle Hole Leakage Test]

The sealed warp knitted fabric having a surgical suture (Prolene 6-0, manufactured by Ethicon) (single stitch) passing through the center of the fabric was attached to a leakage tester, and the amount of water permeating through the sample per minute was measured under application of pressure. The test was performed three times, and the measured values were averaged.

[Deflection]

The sample was placed on a sample holder in accordance with "JIS L1096:2010 Method of testing woven fabric and knitted fabric, 8.21 Measurement of bending resistance." The gravitational deflection ($\delta$) of the sample from the horizontal plane was then measured.

[Mechanical Properties]

The elastic modulus, tensile strength, and elongation of the sample were determined by a tensile test with a small table tester (EZ-SX, manufactured by Shimadzu Corporation).

The amount of hydrogel coating and the thickness and water resistance of the sealed warp knitted fabric were determined using the aforementioned processes.

Example 19

The warp knitted fabric prepared in Example 1 was ultrasonically washed. The warp knitted fabric was cut into a shape adaptable to an immersion container (rectangular dish, manufactured by Grainer, 120 mm by 120 mm) and then placed in the container. A circular metal frame was placed on the warp knitted fabric to fix the fabric to the container. A 10% gelatin solution (MediGelatin, manufactured by Nippi, Incorporated) (5.4 mL) was added to the container, and the warp knitted fabric was immersed in the solution.

The container was allowed to stand at room temperature for two hours to coat (seal) the warp knitted fabric with gelatin so as to prevent permeation of a fluid through the fabric. Separately, a 0.4% glutaraldehyde solution (50% glutaraldehyde solution, manufactured by Tokyo Chemical Industry Co., Ltd.) was cooled at 4° C. The cooled glutaraldehyde solution (6.4 mL) was added to the container, and reaction was allowed to proceed at room temperature for one hour, to cross-link the gelatin. After completion of the reaction, the resultant product was washed with distilled water and dried under vacuum overnight. The dried product was immersed in 40% aqueous glycerin (Japanese Pharmacopoeia grade glycerin, manufactured by KENEI Pharmaceutical Co., Ltd.) (15 mL) for 30 minutes, to prepare a medical material composed of the gelatin-coated warp knitted fabric.

Example 20

A sample was prepared as in Example 19 except that the amount of the 10% gelatin solution was adjusted to 4.3 mL for varying the amount of gelatin coating.

Example 21

A sample was prepared as in Example 19 except that the amount of the 10% gelatin solution was adjusted to 2.9 mL for varying the amount of gelatin coating.

Example 22

A sample was prepared as in Example 19 except that the amount of the 10% gelatin solution was adjusted to 7.2 mL for varying the amount of gelatin coating.

Example 23

A sample was prepared as in Example 19 except that a 13% gelatin solution was added in an amount of 3.3 mL.

Example 24

A sample was prepared as in Example 19 except that the 10% gelatin solution was used and the concentration of the glutaraldehyde solution was varied to 0.1%.

Example 25

A sample was prepared as in Example 19 except that the amount of the 10% gelatin solution was adjusted to 5.4 mL for varying the amount of gelatin coating and the concentration of the glutaraldehyde solution was varied to 10%.

Example 26

A sample was prepared as in Example 19 except that the amount of the 10% gelatin solution was adjusted to 7.2 mL for varying the amount of gelatin coating and the concentration of the glutaraldehyde solution was varied to 0.1%.

Example 27

A sample was prepared as in Example 19 except that the amount of the 10% gelatin solution was adjusted to 7.2 mL for varying the amount of gelatin coating and the concentration of the glutaraldehyde solution was varied to 10%.

Example 28

A sample was prepared as in Example 19 except that a warp knitted fabric was prepared under different conditions (32 gauges, 100 courses) and the amount of the 10% gelatin solution was varied to 2.9 mL.

Example 29

A sample was prepared as in Example 28 except that the amount of the 10% gelatin solution was adjusted to 5.4 mL for varying the amount of gelatin coating.

Example 30

A sample was prepared as in Example 28 except that the amount of the 10% gelatin solution was adjusted to 7.2 mL for varying the amount of gelatin coating.

Example 31

A sample was prepared as in Example 28 except that a warp knitted fabric was prepared under different conditions (32 gauges, 60 courses) and the amount of the 10% gelatin solution was varied to 7.2 mL.

Example 32

A sample was prepared as in Example 19 except that the amount of the 10% gelatin solution was adjusted to 1.8 mL for varying the amount of gelatin coating. The needle hole leakage test of the sample showed a slightly large leakage of 3.0 g/min.

Example 33

A sample was prepared as in Example 19 except that the amount of the 10% gelatin solution was adjusted to 9.0 mL for varying the amount of gelatin coating. The water resistance test and the needle hole leakage test of the sample showed no leakage of fluid. The sample was significantly deformed after absorption of water. Such significant deformation during surgery leads to difficulty in suturing.

Example 34

A sample was prepared as in Example 19 except that the amount of the 10% gelatin solution was adjusted to 1.0 mL for varying the amount of gelatin coating and the concentration of the glutaraldehyde solution was varied to 0.05%. The immersion of the sample in ultrapure water at 37° C. resulted in swelling of a gelatin coating layer and exfoliation of a portion of the layer from the warp knitted fabric.

Example 35

A sample was prepared as in Example 31 except that the 10% gelatin solution was replaced with a 13% gelatin solution, the amount of the 13% gelatin solution was adjusted to 7.2 mL, and the concentration of the glutaraldehyde solution was varied to 3.0%. The needle hole leakage test of the sample showed a slightly large leakage of 2.0 g/min.

Example 36

A sample was prepared as in Example 28 except that a warp knitted fabric was prepared under different conditions (32 gauges, 60 courses) and the amount of the 10% gelatin solution was varied to 2.9 mL. The sample was slightly inferior to other samples in terms of water resistance and needle hole leakage.

Example 37

A sample was prepared as in Example 28 except that a warp knitted fabric was prepared under different conditions (32 gauges, 60 courses) and the amount of the 10% gelatin solution was varied to 10.8 mL. The needle hole leakage test of the sample showed a slightly large leakage of 2.4 g/min. The sample was deformed after absorption of water.

Example 38

A sample was prepared as in Example 37 except that a warp knitted fabric was prepared under different conditions (32 gauges, 100 courses) and the amount of the 10% gelatin solution was varied to 1.45 mL. The needle hole leakage test of the sample showed a slightly large leakage of 5.3 g/min.

Example 39

A sample was prepared as in Example 37 except that a warp knitted fabric was prepared under different conditions (32 gauges, 100 courses) and the amount of the 10% gelatin solution was adjusted to 10.8 mL for varying the amount of gelatin sealing. The sample was deformed after absorption of water as in the sample of Example 32.

Example 40

A sample was prepared as in Example 19 except that the amount of the 10% gelatin solution was adjusted to 5.4 mL for varying the amount of gelatin coating and the concentration of the glutaraldehyde solution was varied to 50%. The sample exhibited high degree of cross-linkage and thus poor tissue adhesion, and showed needle hole leakage.

Example 41

The bending resistance of the warp knitted fabric (36 gauges, 120 courses) was measured in accordance with "JIS L1096:2010 Method of testing woven fabric and knitted fabric, 8.21 Measurement of bending resistance." The warp knitted fabric exhibited a bending resistance in MD of 3.6 (mN/cm) and was harder than the warp knitted fabric (32 gauges, 90 courses) (bending resistance: 0.7 (mN/cm)) used in Example 16.

Example 42

The elastic modulus of the warp knitted fabric (32 gauges, 120 courses) was measured in MD and TD as in Example 40. The warp knitted fabric exhibited an MD elastic modulus of 5.1 N/mm$^2$ and a TD elastic modulus of 20.9 N/mm$^2$; i.e., slightly large anisotropy.

The results are illustrated in Table 7, The symbols "○" and "Δ" are used for "comprehensive evaluation" in Table 7. A sample marked with "○" is superior in terms of water resistance, needle hole leakage, and handleability. A sample marked with "Δ" is inferior to a sample marked with "○" in terms of, for example, handleability. The symbol "-" refers to no data acquisition.

TABLE 7

|  |  |  | Ex. 19 | Ex. 20 | Ex. 21 | Ex. 22 | Ex. 23 | Ex. 24 | Ex. 25 |
|---|---|---|---|---|---|---|---|---|---|
| Fabric | Gauges/Courses | | | | | 32G/90C | | | |
|  | Fabric areal weight | g/m$^2$ | 70 | 70 | 70 | 70 | 70 | 70 | 70 |
| Properties after gelatin impregnation | Amount of gelatin coating | mg/cm$^2$ | 3.2 | 2.8 | 1.6 | 4.9 | 3.2 | 4.0 | 4.9 |
|  | Concentration of crosslinking agent (glutaraldehyde) | % | 0.4 | 0.4 | 0.4 | 0.4 | 0.4 | 0.1 | 10.0 |

TABLE 7-continued

|  |  |  | | | | | | | |
|---|---|---|---|---|---|---|---|---|---|
| | Swelling | % | 624 | 588 | 552 | 593 | 656 | 898 | 485 |
| | Thickness after sealing | mm | 0.25 | 0.24 | 0.22 | 0.29 | 0.24 | 0.27 | 0.25 |
| | Deflection | cm | 3.5 | 3.4 | 3.59 | 3.64 | 3.8 | 3.6 | 3.61 |
| | Elastic modulus | N/mm$^2$ | 5.4 | 7.2 | 8.3 | 3.4 | 14.1 | 6.9 | 2.5 |
| | Tensile strength | Mpa | 13.9 | 14.3 | 14.1 | 11.3 | 92.0 | 14.4 | 15.8 |
| | Elongation | % | 87 | 93 | 78 | 98 | 96 | 99 | 100 |
| | Water resistance test | g/min | 0 | 0 | 0 | 0 | 0 | 0 | 0 |
| | Needle hole leakage test | g/min | 0.10 | 0.07 | 0.45 | 0.22 | 0.14 | 0.07 | 0.68 |
| | Handleability | | Good | Good | Good | Good | Good | Good | Good |
| | Comprehensive evaluation | | ○ | ○ | ○ | ○ | ○ | ○ | ○ |

| | | | Ex. 26 | Ex. 27 | Ex. 28 | Ex. 29 | Ex. 30 | Ex. 31 |
|---|---|---|---|---|---|---|---|---|
| Fabric | Gauges/Courses | | 32G/90C | 32G/90C | 32G/100C | 32G/100C | 32G/100C | 32G/60C |
| | Fabric areal weight | g/m$^2$ | 70 | 70 | 72 | 72 | 72 | 54 |
| Properties after gelatin impregnation | Amount of gelatin coating | mg/cm$^2$ | 4.8 | 6.0 | 1.7 | 3.6 | 4.9 | 5.3 |
| | Concentration of crosslinking agent (glutaraldehyde) | % | 0.1 | 10 | 0.4 | 0.4 | 0.4 | 0.4 |
| | Swelling | % | 858 | 517 | 1028 | 877 | 826 | 760 |
| | Thickness after sealing | mm | 0.29 | 0.28 | 0.21 | 0.25 | 0.27 | 0.26 |
| | Deflection | cm | 3.64 | 3.625 | 3.63 | 3.63 | 3.72 | 3.77 |
| | Elastic modulus | N/mm$^2$ | 5.2 | 2.0 | 4.0 | 3.1 | 2.3 | 1.4 |
| | Tensile strength | Mpa | 12.7 | 13.3 | 11.0 | 10.9 | 10.0 | 9.1 |
| | Elongation | % | 103 | 105 | 88 | 94 | 97 | 118 |
| | Water resistance test | g/min | 0 | 0 | 0 | 0 | 0 | 0 |
| | Needle hole leakage test | g/min | 0.67 | 0.13 | 1.34 | 0.58 | 0.57 | 0.09 |
| | Handleability | | Good | Good | Good | Good | Good | Good |
| | Comprehensive evaluation | | ○ | ○ | ○ | ○ | ○ | ○ |

| | | | Ex. 32 | Ex. 33 | Ex. 34 | Ex. 35 | Ex. 36 | Ex. 37 |
|---|---|---|---|---|---|---|---|---|
| Fabric | Gauges/Courses | | 32G/90C | 32G/90C | 32G/90C | 32G/60C | 32G/60C | 32G/60C |
| | Weight of fabric per unit area | g/m$^2$ | 70 | 70 | 70 | 54 | 54 | 54 |
| Properties after gelatin impregnation | Amount of gelatin coating | mg/cm$^2$ | 1.3 | 6.9 | 3.2 | 7.5 | 2.2 | 8.1 |
| | Concentration of crosslinking agent (glutaraldehyde) | % | 0.4 | 0.4 | 0.05 | 3 | 0.4 | 0.4 |
| | Swelling | % | 531 | 620 | — | 470 | 864 | 705 |
| | Thickness after sealing | mm | 0.21 | 0.30 | — | 0.29 | 0.20 | 0.30 |
| | Deflection | cm | 3.3 | 3.6 | — | 3.69 | 3.67 | 3.67 |
| | Elastic modulus | N/mm$^2$ | 8.0 | 1.9 | — | 1.5 | 2.3 | 1.2 |
| | Tensile strength | Mpa | 15.2 | 10.0 | — | 13.6 | 12.2 | 8.1 |
| | Elongation | % | 86 | 104 | — | 77 | 106 | 120 |
| | Water resistance test | g/min | 0.56 | 0 | — | 0 | 1.6 | 0 |
| | Needle hole leakage test | g/min | 2.99 | 0 | — | 2.03 | 2.00 | 2.40 |
| | Handleability | | Good | Deformed sample slice | Exfoliated gelatin coating layer | Good | Good | Deformed sample slice |
| | Comprehensive evaluation | | Δ | Δ | Δ | Δ | Δ | Δ |

| | | | Ex. 38 | Ex. 39 | Ex. 40 | Ex. 41 | Ex. 42 |
|---|---|---|---|---|---|---|---|
| Fabric | Gauges/Courses | | 32G/100C | 32G/100C | 32G/90C | 36G/120C | 32G/120C |
| | Weight of fabric per unit area | g/m$^2$ | 72 | 72 | 70 | 80 | 80 |

TABLE 7-continued

| Properties after gelatin impregnation | Amount of gelatin coating | mg/cm² | 0.9 | 7.2 | 4.2 | — | — |
|---|---|---|---|---|---|---|---|
| | Concentration of crosslinking agent (glutaraldehyde) | % | 0.4 | 0.4 | 50 | — | — |
| | Swelling | % | 1098 | 731 | 413 | — | — |
| | Thickness after sealing | mm | 0.21 | 0.31 | 0.24 | — | — |
| | Deflection | cm | 3.64 | 3.61 | 3.59 | — | — |
| | Elastic modulus | N/mm² | 4.4 | 1.9 | 2.8 | — | — |
| | Tensile strength | Mpa | 12.3 | 9.9 | 15.3 | — | — |
| | Elongation | % | 86 | 104 | 93 | — | — |
| | Water resistance test | g/min | 0.5 | 0 | 0 | — | — |
| | Needle hole leakage test | g/min | 5.30 | 0.21 | 0.55 | — | — |
| | Handleability | | Good | Deformed sample slice | Low tissue adhesion | No appropriate deflection and low tissue adhesion | No appropriate deflection and low tissue adhesion |
| | Comprehensive evaluation | | Δ | Δ | Δ | Δ | Δ |

Figure 43:
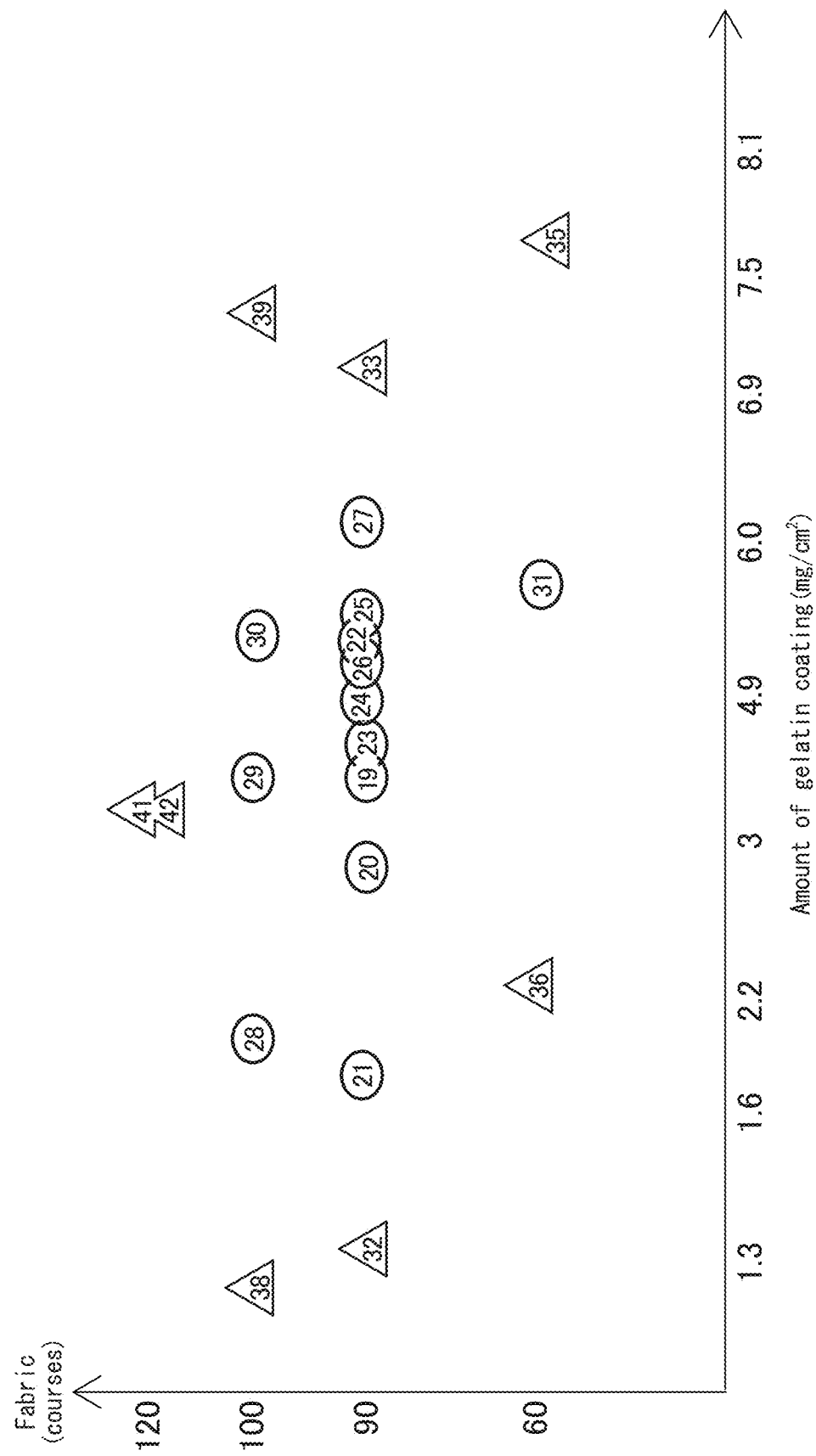
FIG. 43 illustrates plots of sealing conditions (the amount of gelatin coating and the weight of a fabric per unit area) in Examples 19 to 42. Numbers in open circles and open triangles correspond to Examples.

FIG. 43 illustrates plots of sealing conditions (the fabric areal weight and the amount of gelatin coating) in the Examples.

Figure 44:
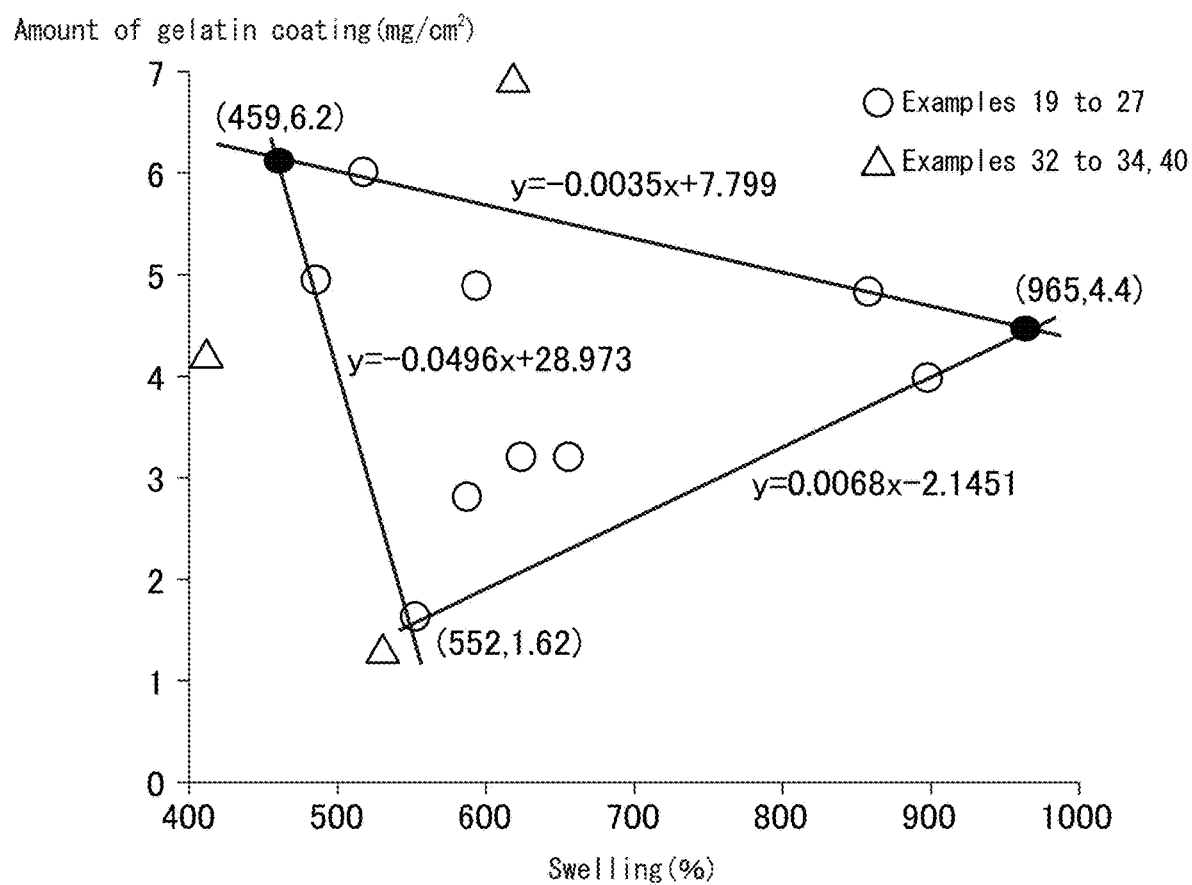
FIG. 44 illustrates plots of sealing conditions (90 courses, the weight of a fabric per unit area (70 g/m$^2$), the amount of gelatin coating, and swelling (%)) in Examples 19 to 27, 32 to 34, and 40.

FIG. 44 illustrates plots of sealing conditions (the amount of gelatin coating and swelling (%) in the case of 90 courses and a fabric areal weight of 70 g/m²) in Examples 19 to 27, 32 to 34, and 40. In FIG. 44, coordinate point (459 (swelling), 6.2 (amount of gelatin coating)) is an extrapolation value obtained by the equation y=−0.0035x+7.799 of a straight line connecting coordinate point (858 (swelling), 4.8 (amount of gelatin coating)) in Example 26 and coordinate point (517 (swelling), 6.0 (amount of gelatin coating)) in Example 27 and the equation y=−0.0496x+28.973 of a straight line connecting coordinate point (552 (swelling), 1.6 (amount of gelatin coating)) in Example 21 and coordinate point (485 (swelling), 4.9 (amount of gelatin coating)) in Example 25. In FIG. 44, coordinate point (965 (swelling), 4.4 (amount of gelatin coating)) is an extrapolation value obtained by the y=−0.0035x+7.799 and the equation y=0.0068x−2.1451 of a straight line connecting coordinate point (552 (swelling), 1.6 (amount of gelatin coating)) in Example 21 and coordinate point (898 (swelling), 3.98 (amount of gelatin coating)) in Example 24.

Figure 45:
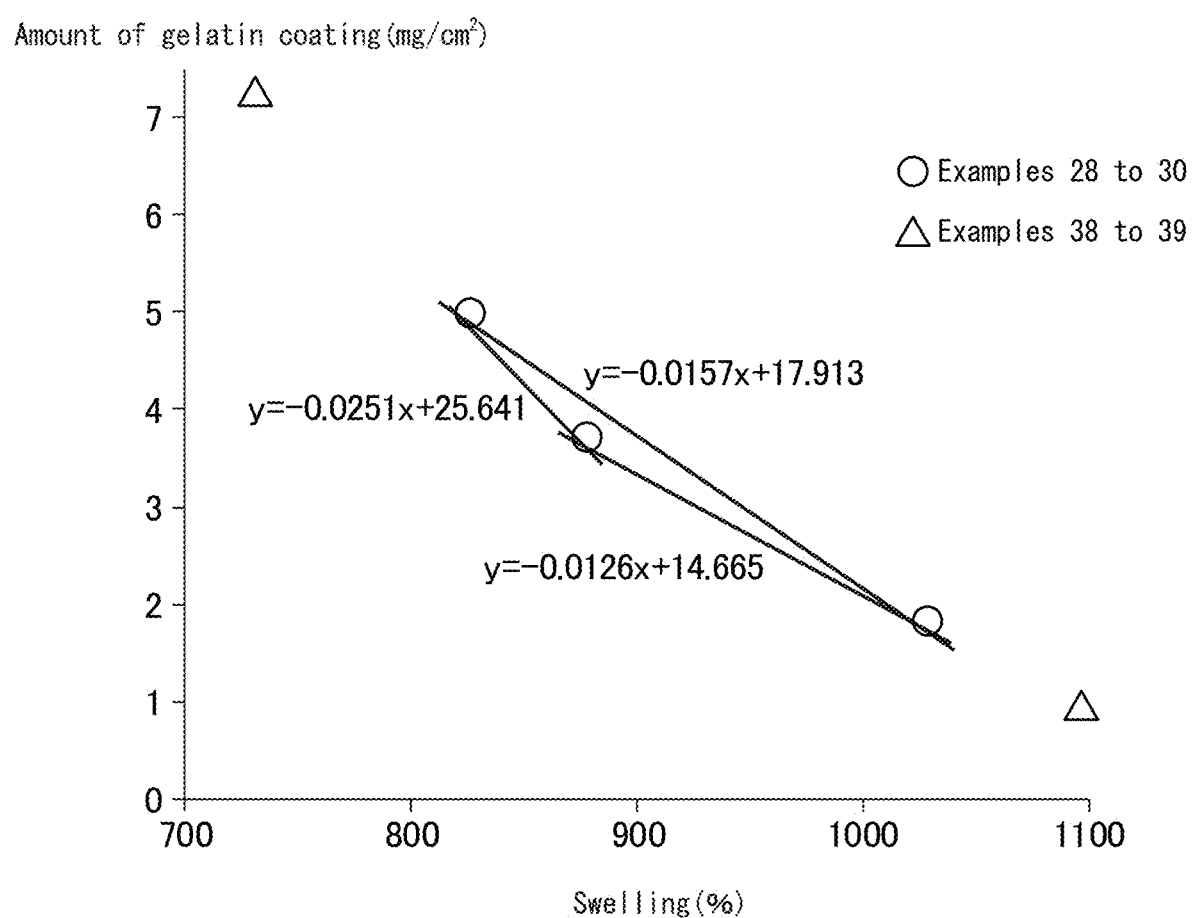
FIG. 45 illustrates plots of sealing conditions (100 courses, the weight of a fabric per unit area (72 g/m$^2$), the amount of gelatin coating, and swelling (%)) in Examples 28 to 30 and 38 to 39.

FIG. 45 illustrates plots of sealing conditions (the amount of gelatin coating and swelling (%) in the case of 100 courses and a fabric areal weight of 72 g/m²) in Examples 28 to 30 and Examples 38 and 39.

INDUSTRIAL APPLICABILITY

The warp knitted fabric of the present invention is suitable for use in, for example, a restorative or a reinforcement for the damage, defect, or stenosis of a biological tissue, such as blood vessel, cardiac valve, pericardium, dura mater, cartilage, skin, mucosa, ligament, tendon, muscle, trachea, and peritoneum. In particular, the warp knitted fabric is suitable for use as a cardiac patch for repairing a cardiovascular tissue in the surgery for a congenital cardiac disease, such as ventricular septal defect, tetralogy of Fallot, pulmonary artery stenosis, or single ventricle.

REFERENCE SIGNS LIST 1a, 1b, 1c: first loop column
2, 2a, 2a1, 2a2, 2b, 2c: second loop column
10, 11, 12, 13: warp knitted fabric
20: leakage tester
21: bottom port
22: container
23: sealed warp knitted fabric
24: electronic balance

The invention claimed is:

1. A warp knitted fabric consisting of:
 a plurality of first loop columns, each consisting of a group of consecutive loops in a warp direction, wherein each loop consists of a first yarn and a second yarn; and
 a plurality of second loop columns, each consisting of a group of consecutive loops in a warp direction, wherein consecutive one to five second loop columns are disposed between the first loop columns, and
 wherein each second loop column consists of
 (p) one or more loops of only the second yarn, and
 (q) one or more loops consisting of (q-i) the first yarn or (q-ii) the first yarn and the second yarn,
 and wherein said (p) and said (q) are alternately disposed;
 any two adjacent loop columns of the first and/or second loop columns are linked together;
 any three first loop columns which are consecutive through one to five second loop columns positioned between the first loop columns are linked together with said first yarn that interlaces and constitutes a part of said first loop columns and said second loop columns therebetween and said three first loop columns are linked together also with said second yarn that interlaces and constitutes the remaining part of said first loop columns and said second loop columns therebetween; and
 both the first yarn and the second yarn form an identical atlas pattern solely, and
 the first yarn has a bioabsorption rate lower than that of the second yarn.

2. The warp knitted fabric according to claim 1, wherein the first yarn is composed of a non-bioabsorbable material and the second yarn is composed of a bioabsorbable material.

3. The warp knitted fabric according to claim 1, wherein the first and/or second yarn is a multifilament yarn.

4. The warp knitted fabric according to claim 1, for use in a medical material.

5. A medical material comprising the warp knitted fabric according to claim 1, wherein at least one surface of the warp knitted fabric is coated with a hydrogel, or a space between yarns of the warp knitted fabric is filled with the hydrogel.

6. The medical material according to claim 5, wherein the hydrogel is gelatin and/or collagen.

7. The medical material according to claim 6, wherein the hydrogel is gelatin.

* * * * *